(12) United States Patent
Qian et al.

(10) Patent No.: US 8,691,820 B2
(45) Date of Patent: Apr. 8, 2014

(54) CDK INHIBITORS

(75) Inventors: Changgeng Qian, Wayland, MA (US); Xiong Cai, Bedford, MA (US); Haixiao Zhai, Bedford, MA (US)

(73) Assignee: Curis, Inc., Lexington, MA (US)

( * ) Notice: Subject to any disclaimer, the term of this patent is extended or adjusted under 35 U.S.C. 154(b) by 0 days.

(21) Appl. No.: 13/167,208

(22) Filed: Jun. 23, 2011

(65) Prior Publication Data

US 2012/0165335 A1   Jun. 28, 2012

Related U.S. Application Data

(63) Continuation of application No. PCT/US2009/069462, filed on Dec. 23, 2009.

(60) Provisional application No. 61/140,493, filed on Dec. 23, 2008.

(51) Int. Cl.
*A61K 31/427* (2006.01)
*C07D 417/14* (2006.01)
*A61K 31/4439* (2006.01)
*A61K 31/498* (2006.01)
*A61P 31/14* (2006.01)
*A61P 35/02* (2006.01)
*A61P 31/18* (2006.01)
*A61P 31/20* (2006.01)
*A61P 31/22* (2006.01)
*C07D 417/12* (2006.01)
*A61P 35/00* (2006.01)

(52) U.S. Cl.
USPC ........... 514/249; 514/342; 514/369; 544/354; 546/270.7; 548/181; 548/185

(58) Field of Classification Search
None
See application file for complete search history.

(56) References Cited

U.S. PATENT DOCUMENTS

| 6,413,974 B1 | 7/2002 | Dumont et al. |
| 2001/0006976 A1 | 7/2001 | Chen et al. |
| 2002/0061915 A1 | 5/2002 | Kimball et al. |
| 2002/0137778 A1 | 9/2002 | Kim et al. |
| 2005/0234033 A1 | 10/2005 | Anandan et al. |
| 2008/0221132 A1 | 9/2008 | Cai et al. |
| 2009/0093507 A1 | 4/2009 | Qian et al. |
| 2011/0178095 A1* | 7/2011 | Cai et al. ................ 514/252.19 |

FOREIGN PATENT DOCUMENTS

| FR | 2865207 A1 | 7/2005 |
| WO | 0144217 A1 | 6/2001 |
| WO | 0210162 A1 | 2/2002 |
| WO | 2005073202 A1 | 8/2005 |
| WO | 2007022258 A1 | 2/2007 |
| WO | 2009002534 A1 | 12/2008 |
| WO | 2010009139 A2 | 1/2010 |
| WO | 2010009155 A2 | 1/2010 |

OTHER PUBLICATIONS

Lohani, S. (2006) Understanding nucleation process in the crystallization of polymorphs. (Doctoral dissertataion). Retrieved from ProQuest Dissertataions and Thesis. (Assession Order No. AAT3234930).*
Morissette, S. L., Almarsson, O., Peterson, M. L., Remenar, J. F., Read, M. J., Lemmo, A. V., Ellis, S., Cima, M. J., Gardner, C. R. High-throughput crystallization: polymorphs, salts, co-crystals, and solvates of pharmaceutical solids. Advanced Drug Delivery Reviews. Feb. 2004, 56, 275-300.*
Kim, K.S., et. al., "Discovery of Aminothiazole Inhibitors of Cyclin-Dependent Kinase 2: Synthesis, X-ray Crystallographic Analysis, and Biological Activities," J. Med. Chem., 45: 3905-3927 (2002).
Fischer, P.M., "Cyclin-dependent kinase inhibitors: discovery, development and target rationale for different therapeutic applications," Drugs of the Future, 30(9): 911-929 (2005).
Misra, Raj N., et. al., "N-(Cycloalkylamino)acyl-2-aminothiazole Inhibitors of Cyclin-Dependent Kinase 2. N-[5-[[[5-(1,1-Dimethylethyl)-2-oxazolyl]methyl]thio]-2-thiazolyl]-4-piperidinecarboxamide (BMS-387032), a Highly Efficacious and Selective Antitumor Agent," J. Med. Chem., 47: 1719-1728 (2004).
Garcia-Sosa, A.T., et. al., "The effect of a tightly bound water molecule on scaffold diversity in the computer-aided de novo ligand design of CDK2 inhibitors," J. Mol. Model., 12: 422-431 (2006).
Hurd, Charles D., et. al., "The 2-Aminothiazoles," J. Am. Chem. Soc., 71: 4007-4010 (1949).

* cited by examiner

*Primary Examiner* — Michael Barker
*Assistant Examiner* — Po-Chih Chen
(74) *Attorney, Agent, or Firm* — Elmore Patent Law Group, P.C.; Edgar W. Harlan; Carolyn S. Elmore, Esq.

(57) ABSTRACT

The present invention relates to CDK inhibitors and their use in the treatment of cell proliferative diseases such as cancer.

17 Claims, No Drawings

CDK INHIBITORS

RELATED APPLICATIONS

This application is a continuation of International Application No. PCT/US09/69462, which designated the United States and was filed on Dec. 23, 2009, published in English, which claims the benefit of U.S. Provisional Application No. 61/140,493, filed on Dec. 23, 2008. The entire teachings of the above applications are incorporated herein by reference.

BACKGROUND OF THE INVENTION

Cyclin-dependent kinases (CDKs) are a family of serine/threonine kinases that regulate key cellular processes including cell cycle progression and RNA transcription (Shapiro G I. *J Clin Oncol.* 2006 Apr. 10; 24(11):1770-83). Heterodimerized with regulatory cyclin units, CDKs can be generally divided into two groups based on their functions. The first group consists of core cell cycle components and governs the cell cycle transition and cell division: cyclin D-dependent kinases 4/6 and cyclin E-dependent kinase 2, which control the G1→S transition; cyclin A-dependent kinases 1/2, a critical regulator of S-phase progression; cyclin B-dependent CDK1, required for the G2→M transition; and cyclin H/CDK7, the CDK-activating kinase. The second group, so called transcriptional CDKs, includes cyclin H/CDK7 and cyclin T/CDK9 which phosphorylate the C-terminal domain (CTD) of RNA polymerase II and promote transcriptional initiation and elongation.

The deregulation of the CDK activity is detected in virtually all forms of human cancer, most frequently due to the overexpression of cyclins and loss of expression of CDK inhibitors (de Cárcer G et al., *Curr Med. Chem.* 2007; 14(9): 969-85). CDK4/6 inhibition has been shown to induce potent G1 arrest in vitro and tumor regression in vivo (Lukas J et al., *Nature.* 1995 Jun. 8; 375(6531):503-6; Schreiber M et al., *Oncogene.* 1999 Mar. 4; 18(9):1663-76; Fry D W et al., *Mol Cancer Ther.* 2004 November; 3(11):1427-38). Various approaches aimed at targeting CDK2/1 have been reported to induce S and G2 arrest followed by apoptosis (Chen Y N et al., *Proc Natl Acad Sci USA.* 1999 Apr. 13; 96(8):4325-9; Chen W et al., *Cancer Res.* 2004 Jun. 1; 64(11):3949-57; Mendoza N et al., *Cancer Res.* 2003 Mar. 1; 63(5):1020-4). Inhibition of the transcriptional CDKs 7 and 9 can affect the accumulation of transcripts encoding anti-apoptosis family members, cell cycle regulators, as well as p53 and NF-κB-responsive gene targets (Lam L T et al., *Genome Biol.* 2001; 2(10): RESEARCH0041). All these effects contribute to the induction of apoptosis and also potentiation of cytotoxicity mediated by disruption of a variety of pathways in many cancer cell types (Chen R et al., *Blood.* 2005 Oct. 1; 106(7):2513-9; Pepper C et al., *Leuk Lymphoma.* 2003 February; 44(2):337-42). CDKs are therefore recognized as an attractive target for the design and development of compounds that can specifically bind and inhibit the cyclin-dependent kinase activity and its signal transduction pathway in cancer cells, and thus can serve as either diagnostic or therapeutic agents. For example, the potent and highly selective CDK2/1 inhibitor, SNS-032 (BMS-387032), and the CDK4/6 inhibitor, PD 332991, are currently in clinical trials for treatment of cancer.

Numerous reports have indicated that CDK inhibitors may be therapeutically effective in several other disease indications than cancer, including polycystic kidney disease (Ibraghimov-Beskrovnaya O, Cell Cycle. 2007, 6:776-9), mesangial proliferative glomerulonephritis, crescentic glomerulonephritis, proliferative lupus nephritis, collapsing glomerulopathy, IgA nephropathy (Soos T J et al., Drug News Perspect. 2006, 19:325-8) and Alzheimer's disease (Monaco E A & Vallano M L. Front Biosci. 2005, 10:143-59). CDKs are required for replication of many viruses such as human cytomegalovirus, herpes simplex virus type 1 and HIV-1. Specific pharmacological CDK inhibitors have demonstrated broad antiviral activities (Schang L M et al., *Antivir Chem. Chemother.* 2006; 17(6):293-320; Pumfery A et al., *Curr Pharm Des.* 2006; 12(16):1949-61). Given the mounting evidence for the role of CDK activity in a variety of disease states, there is a need for new inhibitors of CDK activity.

SUMMARY OF THE INVENTION

The present invention relates to CDK inhibitors containing zinc-binding moiety based derivatives that have enhanced and unexpected properties as inhibitors of CDK and their use in the treatment of CDK related diseases and disorders such as cancer.

Accordingly, the present invention provides a compound having a general formula I:

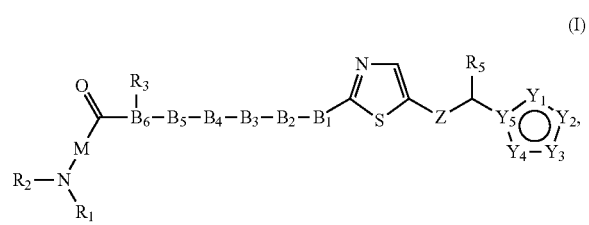

(I)

or a geometric isomer, enantiomer, diastereomer, racemate, pharmaceutically acceptable salt, prodrug or solvate thereof, wherein $Y_1$-$Y_4$ are independently O, S, N, $NR_8$ or $CR_{21}$, where $R_{21}$ is independently selected from hydrogen, hydroxy, substituted hydroxy, amino, substituted amino, halogen, substituted or unsubstituted alkoxy, substituted or unsubstituted alkylamino, substituted or unsubstituted dialkylamino, substituted or unsubstituted thiol, $CF_3$, CN, $NO_2$, $N_3$, substituted carbonyl, sulfonyl, acyl, aliphatic, and substituted aliphatic; $Y_5$ is C or N; M is absent or O; $B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl; $B_2$ is absent, O, S, SO, $SO_2$, $N(R_8)$ or CO; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; Z is O, S, S(O), $SO_2$, $SO_2NH$, $NR_8$, $C_1$-$C_6$ alkyl, $C_2$-$C_6$ alkenyl, $C_2$-$C_6$ alkynyl, C(O) or $C(O)NH_2$, $R_8$ is hydrogen, acyl, aliphatic or substituted aliphatic. $R_1$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocyclic, substituted or unsubstituted aryl, substituted or unsubstituted aryl-$C_1$-$C_6$-alkyl, substituted or unsubstituted heterocyclic-$C_1$-$C_6$-alkyl; $R_2$ is hydrogen or —$OR_4$, where $R_4$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocyclic, substituted or unsubstituted aryl, substituted or unsubstituted aryl-$C_1$-$C_6$-alkyl, substituted or unsubstituted heterocyclic-$C_1$-$C_6$-alkyl; or $R_1$ and $R_2$, together with the nitrogen atom to which they are attached, form a substituted or unsubstituted heterocyclic or heteroaryl group which is optionally fused with a cycloalkyl, aryl or heterocyclic group; preferably, when $R_1$ is H, $R_2$ is not H or —OH. $R_3$ is absent, or $R_3$ and $R_2$, or $R_3$ and $R_1$, together with the intervening atoms, form a heterocyclic group which is optionally fused with a cycloalkyl, aryl or heterocyclic group. $R_5$ is aliphatic or substituted aliphatic, preferably hydrogen or methyl.

In one example, $Y_1$-$Y_4$ are independently O, S, N, $NR_8$ or $CR_{21}$, where $R_{21}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic; $Y_5$ is C or N; $B_1$ is absent, $N(R_8)$, CO, $C_1$-$C_6$ alkyl, $C_2$-$C_6$ alkenyl, $C_2$-$C_6$ alkynyl, cycloalkyl, heterocyclic or aryl; $B_2$ is absent, O, S, SO, $SO_2$, $N(R_8)$ or CO; $B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_6$ is absent, $C_1$-$C_6$ alkyl, $C_2$-$C_6$ alkenyl, $C_2$-$C_6$ alkynyl, cycloalkyl, heterocyclic, aryl, or heteroaryl; $R_1$ is hydrogen, substituted or unsubstituted $C_1$-$C_6$ alkyl, substituted or unsubstituted heterocyclic, or substituted or substituted aryl; $R_2$ is hydrogen or —$OR_4$, where $R_4$ is hydrogen, substituted or unsubstituted $C_1$-$C_6$ alkyl, substituted or unsubstituted cycloalkyl, substituted or unsubstituted heterocyclic, substituted or unsubstituted aryl, substituted or unsubstituted aryl-$C_1$-$C_6$-alkyl, substituted or unsubstituted heterocyclic-$C_1$-$C_6$-alkyl; or $R_1$ and $R_2$, together with the nitrogen atom to which they are attached, form a heterocyclic group which is optionally fused with a cycloalkyl, aryl or heterocyclic group. Preferably, when $R_1$ is H, $R_2$ is not H or —OH.

DETAILED DESCRIPTION OF THE INVENTION

In a first embodiment of the compounds of the present invention are compounds represented by formula (I) as illustrated above, or the geometric isomers, enantiomers, diastereomers, racemates, pharmaceutically acceptable salts, prodrugs and solvates thereof.

In one embodiment of the compounds of the present invention are compounds represented by formula (II) as illustrated below, or the geometric isomers, enantiomers, diastereomers, racemates, pharmaceutically acceptable salts, prodrugs and solvates thereof:

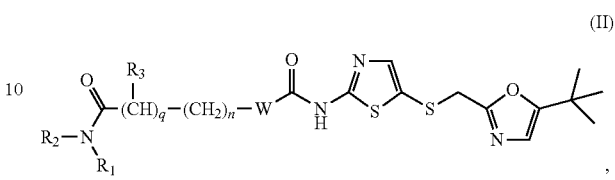

(II)

where n is an integer from 0 to 8, q is 0 or 1, W is a direct bond, O or $N(R_8)$ and $R_1$, $R_2$, $R_3$ and $R_8$ have the definitions given for these variables in Formula I.

In one embodiment of the compounds of the present invention are compounds represented by formula (III) as illustrated below, or its geometric isomers, enantiomers, diastereomers, racemates, pharmaceutically acceptable salts, prodrugs and solvates thereof:

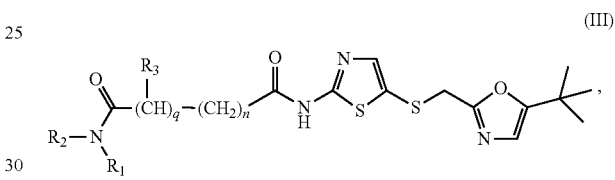

(III)

where n is an integer from 0 to 8, q is 0 or 1, and $R_1$, $R_2$ and $R_3$ have the definitions given for these variables in Formula I.

In another embodiment, the compounds of the present invention are compounds represented by formula (IV) as illustrated below, or geometric isomers, enantiomers, diastereomers, racemates, pharmaceutically acceptable salts, prodrugs and solvates thereof:

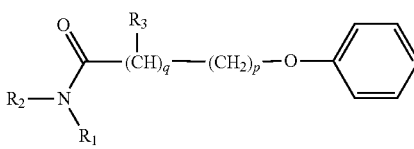

(IV)

where m and p are each independently an integer from 0 to 6, q is 0 or 1, W is a direct bond, O or $N(R_8)$ and $R_1$, $R_2$, $R_3$ and $R_8$ have the definitions given for these variables in Formula I.

In another embodiment, the compounds of the present invention are compounds represented by formula (V) or (VI) as illustrated below, or geometric isomers, enantiomers, diastereomers, racemates, pharmaceutically acceptable salts, prodrugs or solvates thereof:

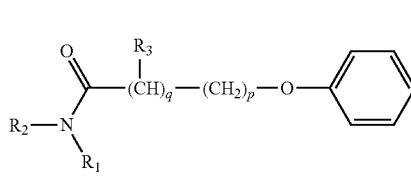

(V)

-continued

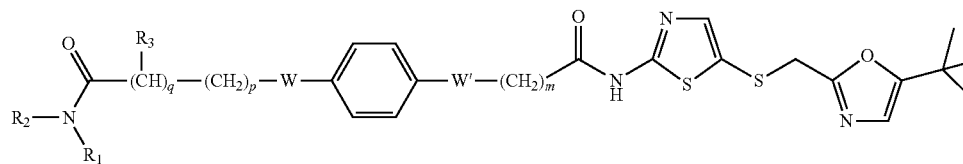
(VI)

where m and p are each independently an integer from 0 to 6, q is 0 or 1, W and W' are each independently a direct bond, O or $N(R_8)$ and $R_1$, $R_2$, $R_3$, and $R_8$ have the definitions given for these variables in Formula I.

In one preferred embodiment of the compounds of formulas I, II, III, IV, V and VI, $R_1$ is hydrogen and $R_2$ is —$OR_4$, where $R_4$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heterocyclic, substituted or unsubstituted aryl, substituted or unsubstituted aryl-$C_1$-$C_6$-alkyl, or substituted or unsubstituted heterocyclic-$C_1$-$C_6$-alkyl. In more preferred embodiments, $R_4$ is $C_1$-$C_6$-alkyl, hydroxy-$C_1$-$C_6$-alkyl, benzyl, or heterocycloalkyl.

In one preferred embodiment of the compounds of Formulas I-VI, $R_1$ is substituted or unsubstituted aryl or substituted or unsubstituted heterocyclic and $R_2$ is H. In a particularly preferred embodiment, $R_1$ is substituted or unsubstituted phenyl, substituted or unsubstituted pyridyl, substituted or unsubstituted pyrazolyl, substituted or unsubstituted imidazolyl, substituted or unsubstituted benzimidazolyl, substituted or unsubstituted pyrrolyl, substituted or unsubstituted benzopyrrolyl or substituted or unsubstituted benzopyrazolyl. In one embodiment $R_1$ is 2-aminophenyl or substituted 2-aminophenyl. In another embodiment, $R_1$ is substituted phenyl, but is not 2-aminophenyl or substituted 2-aminophenyl. In one embodiment, $R_1$ is selected from the groups set below.

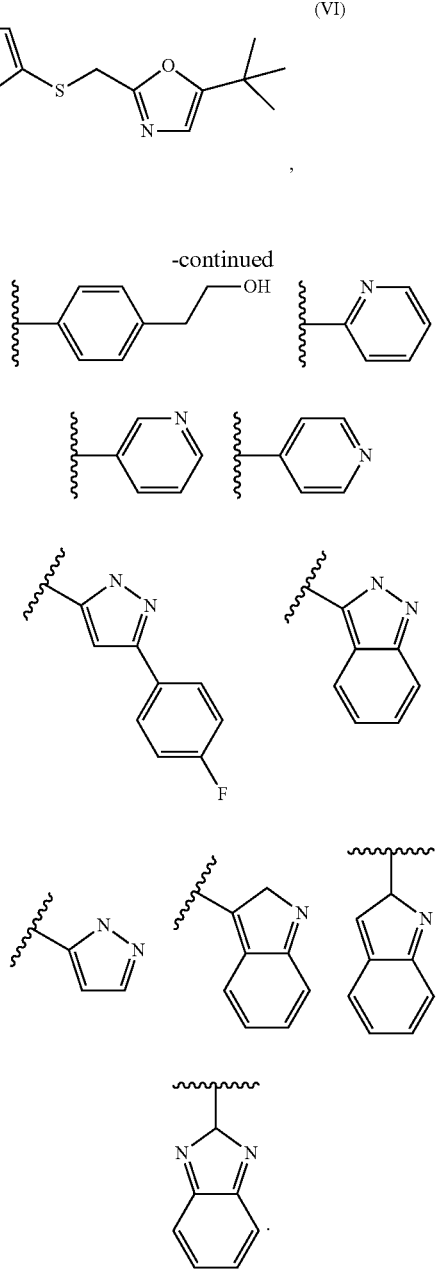

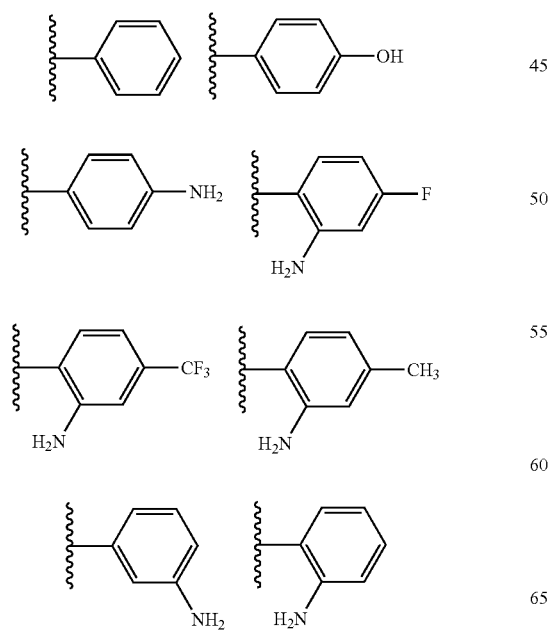

In another embodiment, $R_1$ is selected from the groups set forth below.

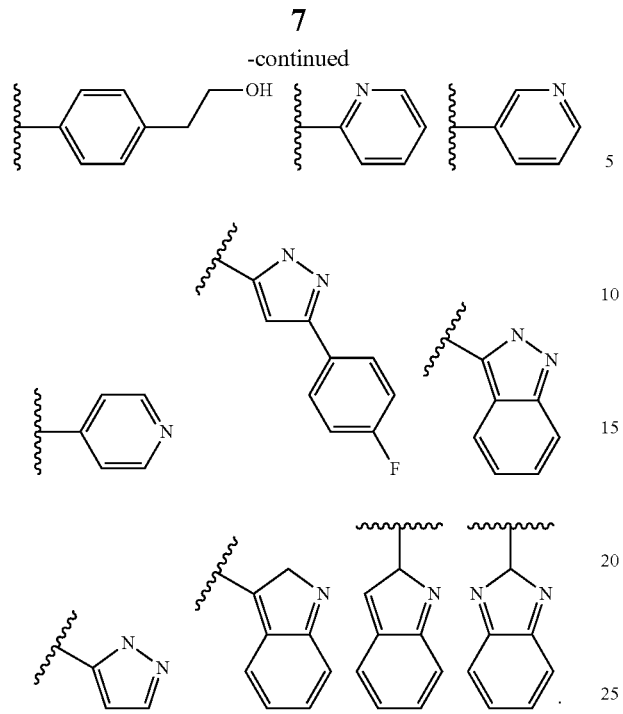
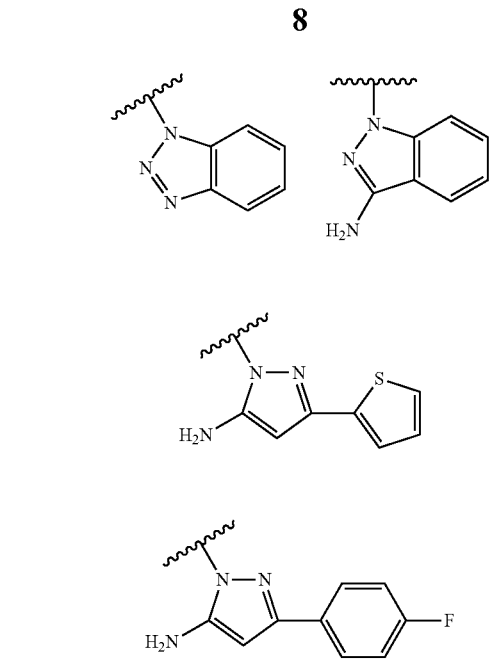

In yet another embodiment, $R_1$ is a 2-aminophenyl group selected from the groups set forth below.

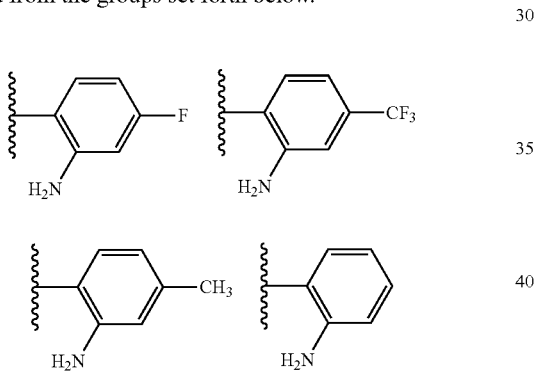

In another preferred embodiment of the compounds of Formulas I-VI, $R_1$ and $R_2$, together with the nitrogen atom to which they are attached, form a heterocyclic group. Preferably, the heterocyclic group is a heteroaromatic group, such as substituted or unsubstituted pyrazolyl, substituted or unsubstituted benzopyrazolyl, substituted or unsubstituted benzotriazolyl. Suitable examples of heteroaromatic groups include, but are not limited to, those shown below.

In another embodiment of the compounds of the invention, $R_3$ and $R_2$, together with the intervening atoms, form a heterocyclic group having the structure

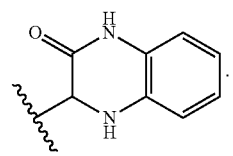 [SMILES: *C1Nc2ccccc2NC1=O]

Another embodiment of the invention includes compounds of Formula I wherein M is O and $R_2$ and $R_3$, together with the intervening atoms, form a group having the structure

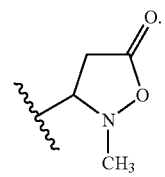 [SMILES: *C1CC(=O)ON1C]

Representative compounds according to the invention are those selected from Table A below or geometric isomers, enantiomers, diastereomers, racemates, pharmaceutically acceptable salts, prodrugs or solvates thereof:

TABLE A

| Compound | Structure |
| --- | --- |
| 1 | ![structure] |

TABLE A-continued

| Compound | Structure |
|---|---|
| 2 | 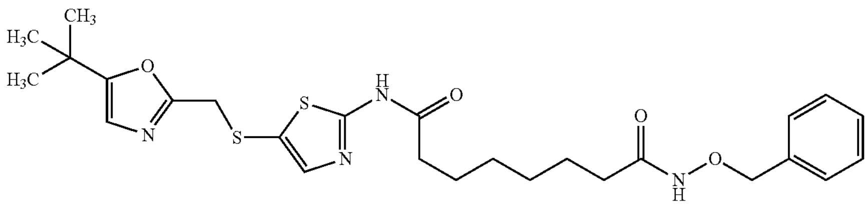 [SMILES: CC(C)(C)c1cnc(CSc2cnc(NC(=O)CCCCCCC(=O)NOCc3ccccc3)s2)o1] |
| 3 | 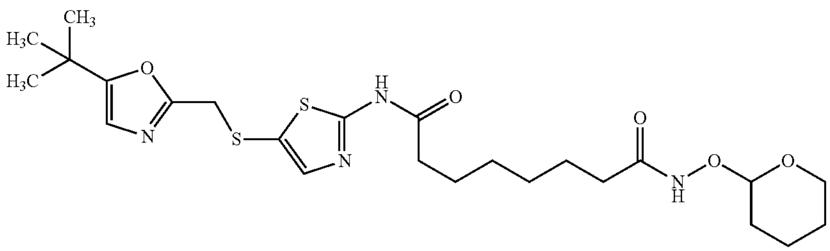 [SMILES: CC(C)(C)c1cnc(CSc2cnc(NC(=O)CCCCCCC(=O)NOC3CCCCO3)s2)o1] |
| 4 | 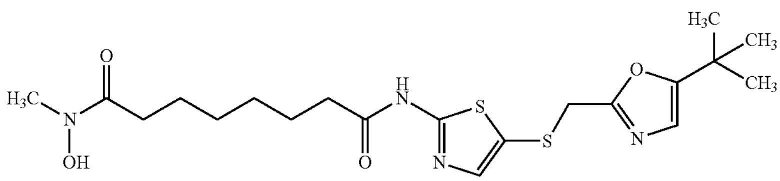 [SMILES: CN(O)C(=O)CCCCCCC(=O)Nc1ncc(SCc2ncc(C(C)(C)C)o2)s1] |
| 5 | 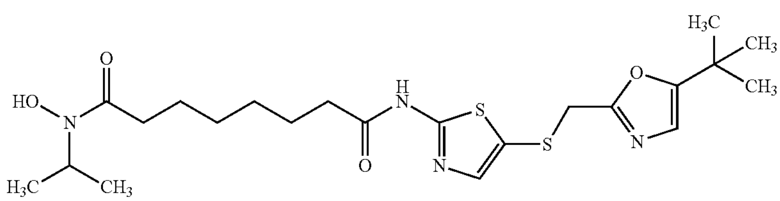 [SMILES: CC(C)N(O)C(=O)CCCCCCC(=O)Nc1ncc(SCc2ncc(C(C)(C)C)o2)s1] |
| 6 | 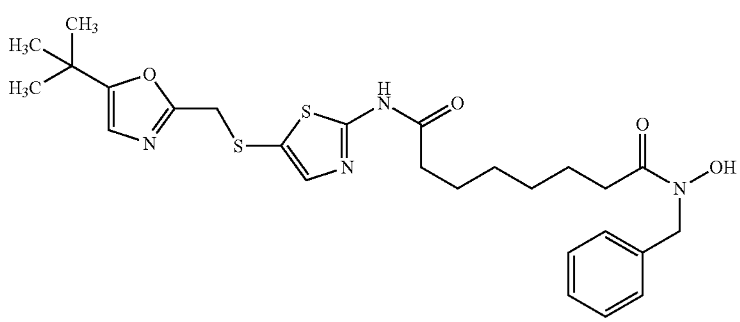 [SMILES: CC(C)(C)c1cnc(CSc2cnc(NC(=O)CCCCCCC(=O)N(O)Cc3ccccc3)s2)o1] |
| 7 | 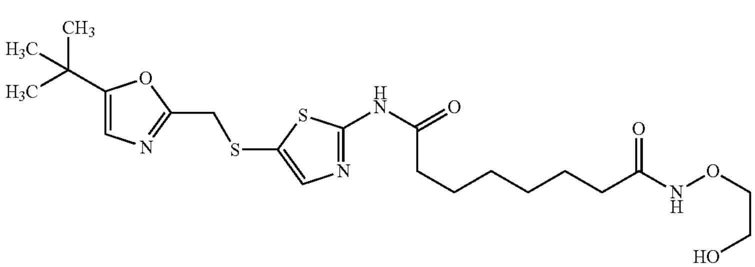 [SMILES: CC(C)(C)c1cnc(CSc2cnc(NC(=O)CCCCCCC(=O)NOCCO)s2)o1] |

TABLE A-continued

| Compound | Structure |
|---|---|
| 8 | 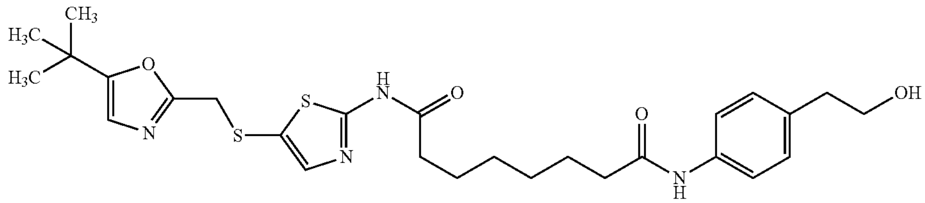 [SMILES: CC(C)(C)c1cnc(CSc2cnc(NC(=O)CCCCCCC(=O)Nc3ccc(CCO)cc3)s2)o1] |
| 9 | 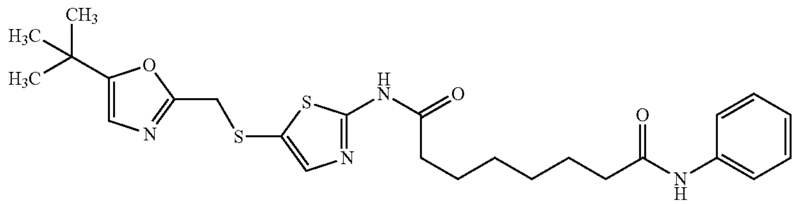 [SMILES: CC(C)(C)c1cnc(CSc2cnc(NC(=O)CCCCCCC(=O)Nc3ccccc3)s2)o1] |
| 10 | 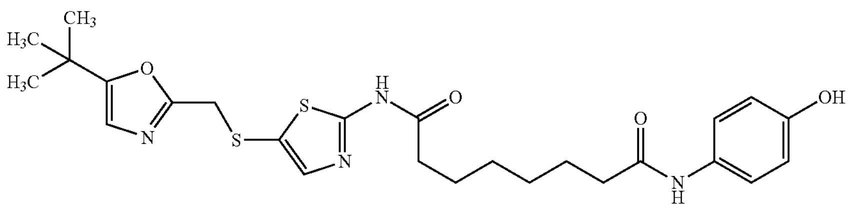 [SMILES: CC(C)(C)c1cnc(CSc2cnc(NC(=O)CCCCCCC(=O)Nc3ccc(O)cc3)s2)o1] |
| 11 | 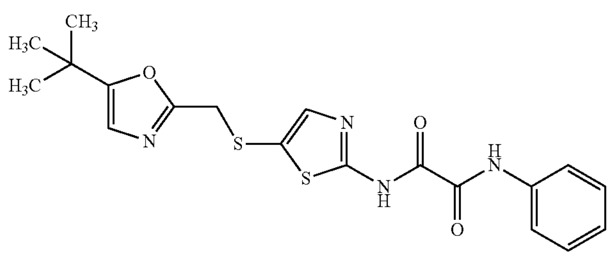 [SMILES: CC(C)(C)c1cnc(CSc2cnc(NC(=O)C(=O)Nc3ccccc3)s2)o1] |
| 12 | 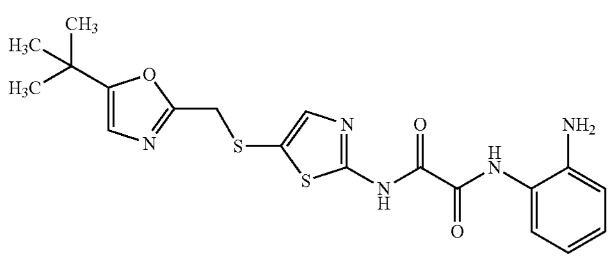 [SMILES: CC(C)(C)c1cnc(CSc2cnc(NC(=O)C(=O)Nc3ccccc3N)s2)o1] |
| 13 | 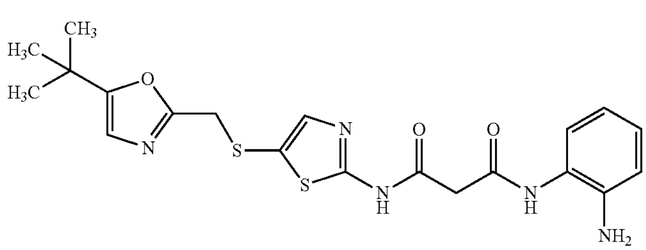 [SMILES: CC(C)(C)c1cnc(CSc2cnc(NC(=O)CC(=O)Nc3ccccc3N)s2)o1] |

TABLE A-continued

| Compound | Structure |
|---|---|
| 14 | 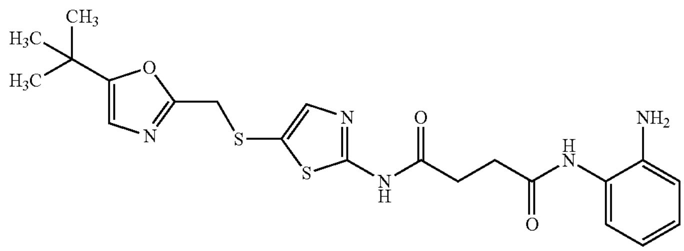 [SMILES: CC(C)(C)c1cnc(CSc2cnc(NC(=O)CCC(=O)Nc3ccccc3N)s2)o1] |
| 15 | 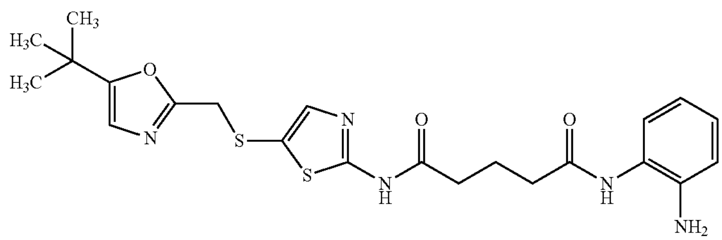 [SMILES: CC(C)(C)c1cnc(CSc2cnc(NC(=O)CCCC(=O)Nc3ccccc3N)s2)o1] |
| 16 | 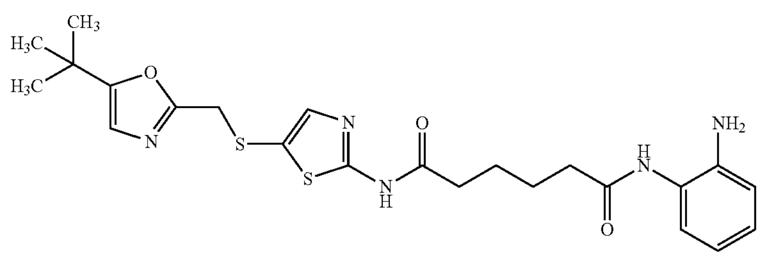 [SMILES: CC(C)(C)c1cnc(CSc2cnc(NC(=O)CCCCC(=O)Nc3ccccc3N)s2)o1] |
| 17 | 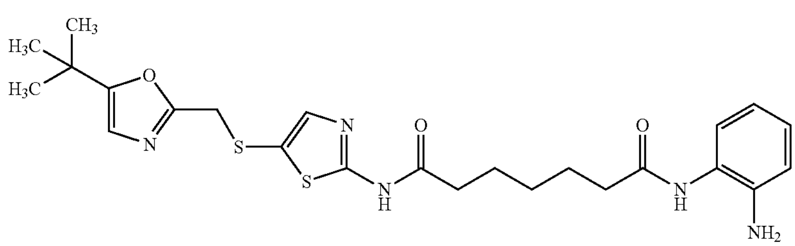 [SMILES: CC(C)(C)c1cnc(CSc2cnc(NC(=O)CCCCCC(=O)Nc3ccccc3N)s2)o1] |
| 18 | 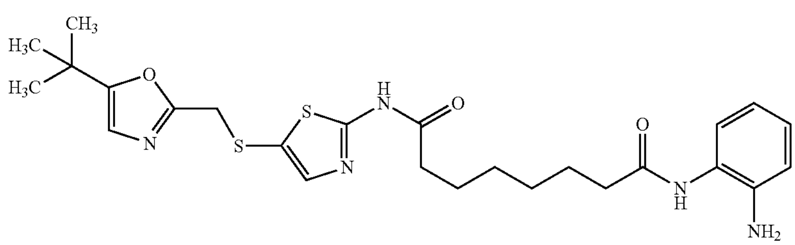 [SMILES: CC(C)(C)c1cnc(CSc2cnc(NC(=O)CCCCCCC(=O)Nc3ccccc3N)s2)o1] |
| 19 | 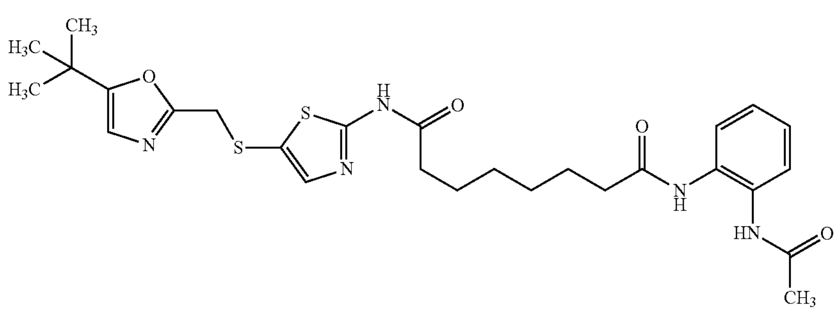 [SMILES: CC(=O)Nc1ccccc1NC(=O)CCCCCCC(=O)Nc1ncc(SCc2ncc(C(C)(C)C)o2)s1] |

TABLE A-continued

| Compound | Structure |
|---|---|
| 20 | 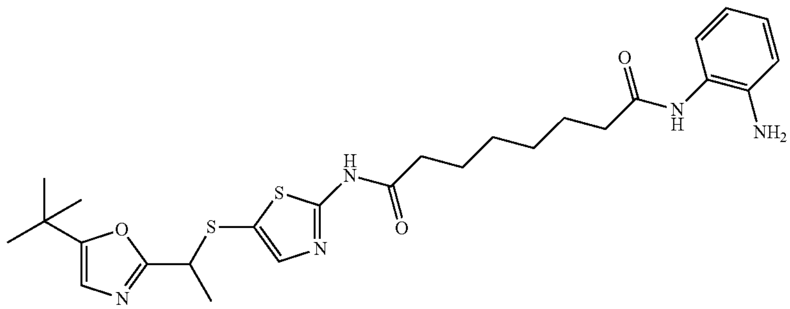 [SMILES: CC(Sc1cnc(NC(=O)CCCCCCC(=O)Nc2ccccc2N)s1)c1ncc(C(C)(C)C)o1] |
| 21 | 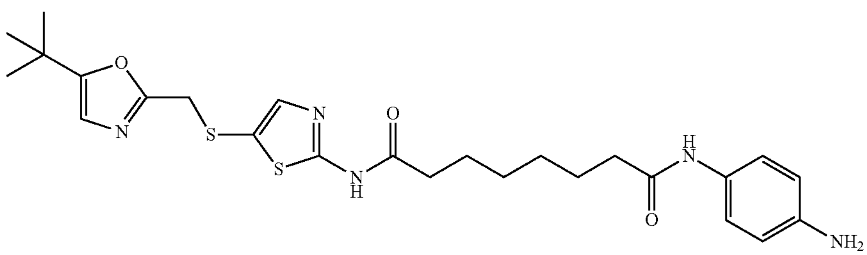 [SMILES: CC(C)(C)c1cnc(CSc2cnc(NC(=O)CCCCCCC(=O)Nc3ccc(N)cc3)s2)o1] |
| 22 | 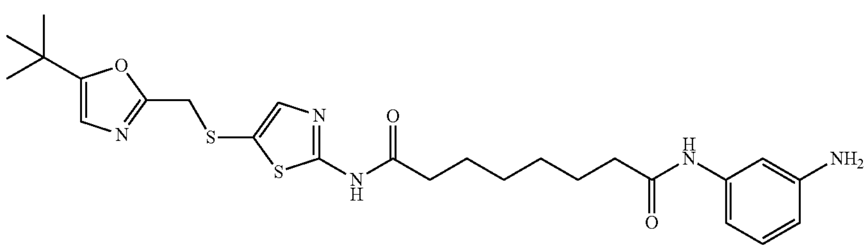 [SMILES: CC(C)(C)c1cnc(CSc2cnc(NC(=O)CCCCCCC(=O)Nc3cccc(N)c3)s2)o1] |
| 23 | 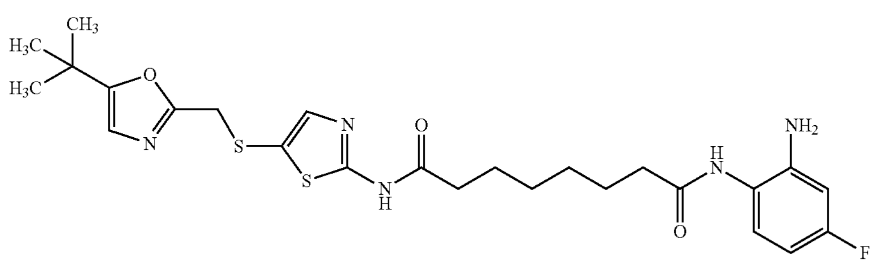 [SMILES: CC(C)(C)c1cnc(CSc2cnc(NC(=O)CCCCCCC(=O)Nc3ccc(F)cc3N)s2)o1] |
| 24 | 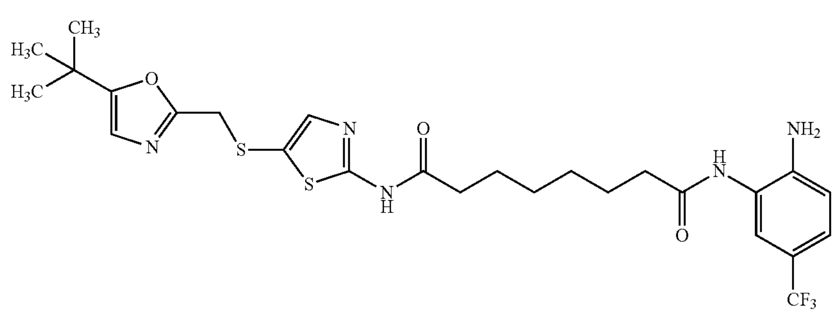 [SMILES: CC(C)(C)c1cnc(CSc2cnc(NC(=O)CCCCCCC(=O)Nc3cc(C(F)(F)F)ccc3N)s2)o1] |

US 8,691,820 B2
17 18
TABLE A-continued
| Compound | Structure |
|---|---|
| 25 | 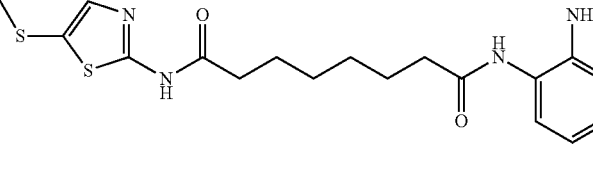 |
| 26 | 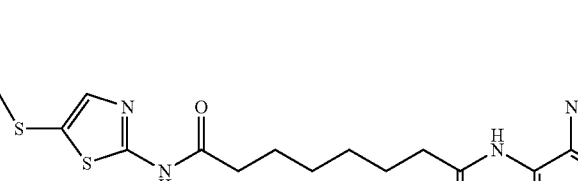 |
| 27 | 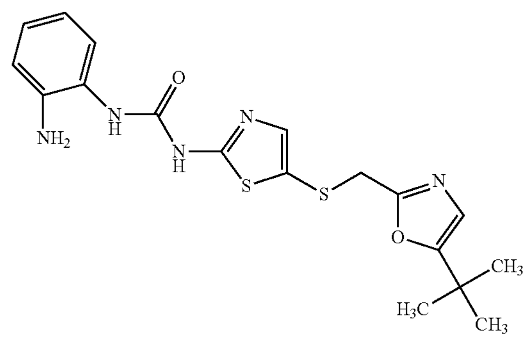 [SMILES: CC(C)(C)c1cnc(CSc2cnc(NC(=O)Nc3ccccc3N)s2)o1] |
| 28 | 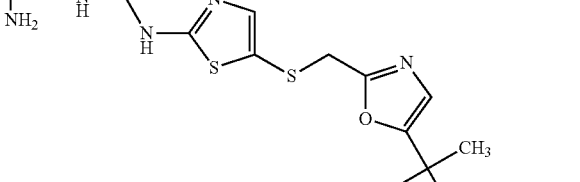 |
| 29 | 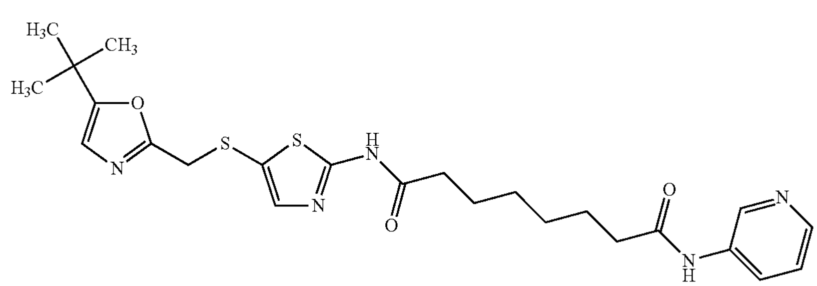 [SMILES: CC(C)(C)c1cnc(CSc2cnc(NC(=O)CCCCCCC(=O)Nc3cccnc3)s2)o1] |

TABLE A-continued

| Compound | Structure |
|---|---|
| 30 | 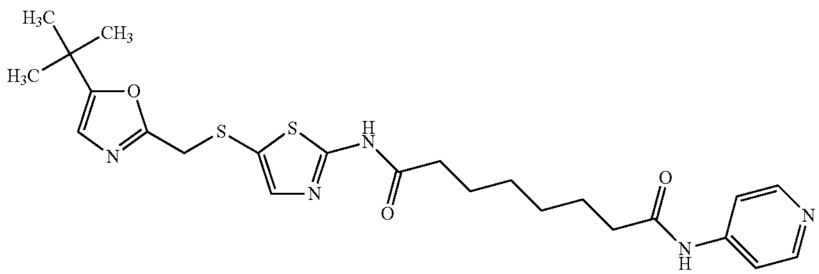 [SMILES: CC(C)(C)c1cnc(CSc2cnc(NC(=O)CCCCCCC(=O)Nc3ccncc3)s2)o1] |
| 31 | 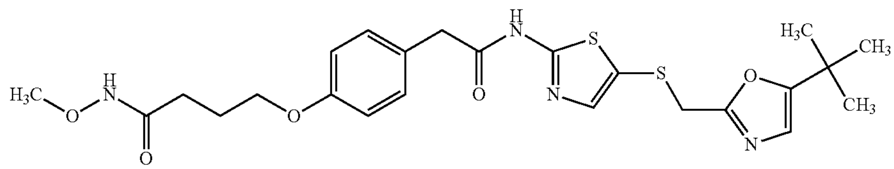 [SMILES: CONC(=O)CCCOc1ccc(CC(=O)Nc2ncc(SCc3ncc(C(C)(C)C)o3)s2)cc1] |
| 32 | 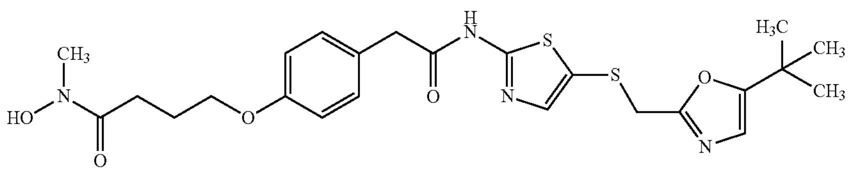 [SMILES: CN(O)C(=O)CCCOc1ccc(CC(=O)Nc2ncc(SCc3ncc(C(C)(C)C)o3)s2)cc1] |
| 33 | 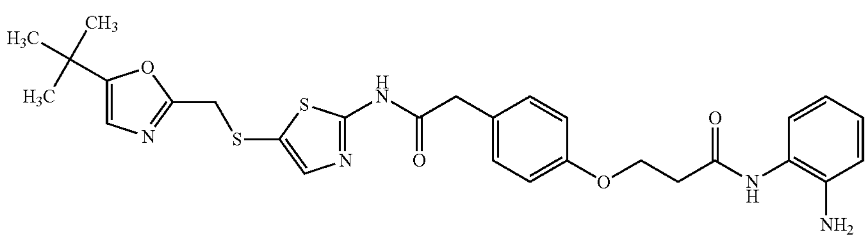 [SMILES: CC(C)(C)c1cnc(CSc2cnc(NC(=O)Cc3ccc(OCCC(=O)Nc4ccccc4N)cc3)s2)o1] |
| 34 | 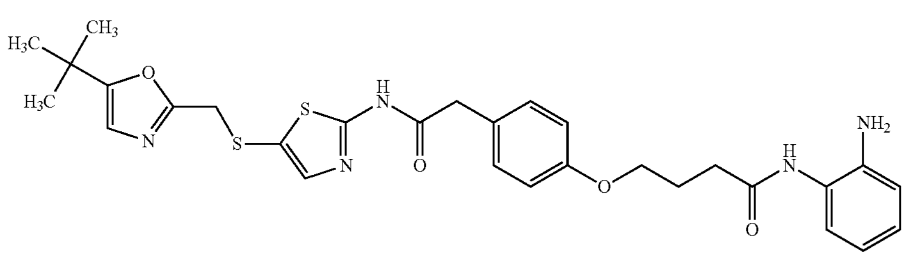 [SMILES: CC(C)(C)c1cnc(CSc2cnc(NC(=O)Cc3ccc(OCCCC(=O)Nc4ccccc4N)cc3)s2)o1] |
| 35 | 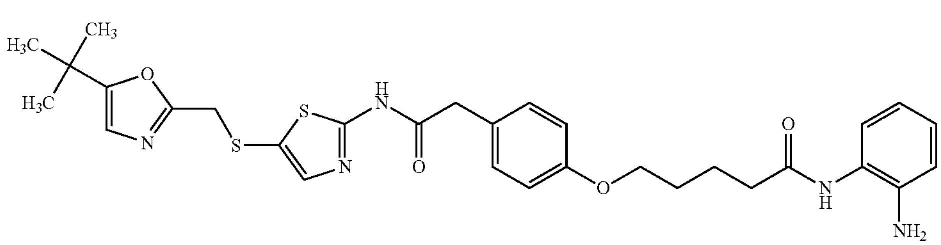 [SMILES: CC(C)(C)c1cnc(CSc2cnc(NC(=O)Cc3ccc(OCCCCC(=O)Nc4ccccc4N)cc3)s2)o1] |

TABLE A-continued
| Compound | Structure |
|---|---|
| 36 | 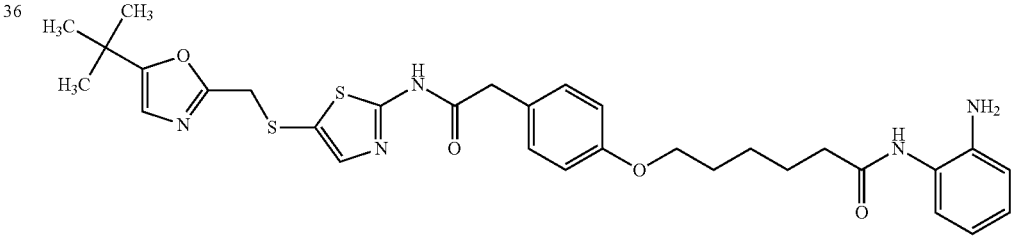 |
| 37 | 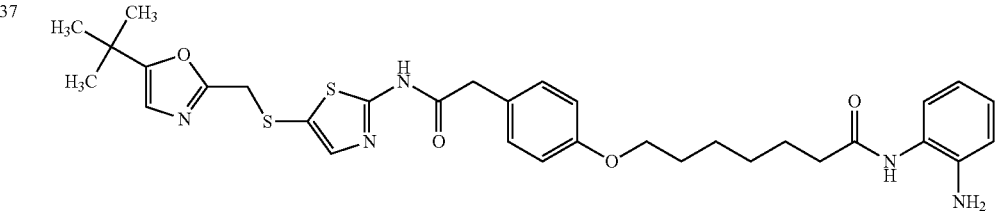 |
| 38 | 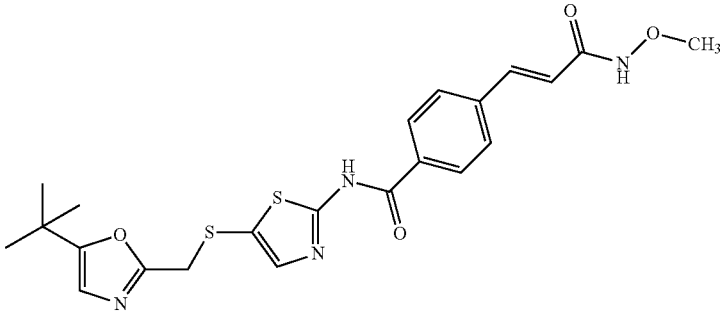 [SMILES: CONC(=O)/C=C/c1ccc(C(=O)Nc2ncc(SCc3ncc(C(C)(C)C)o3)s2)cc1] |
| 39 | 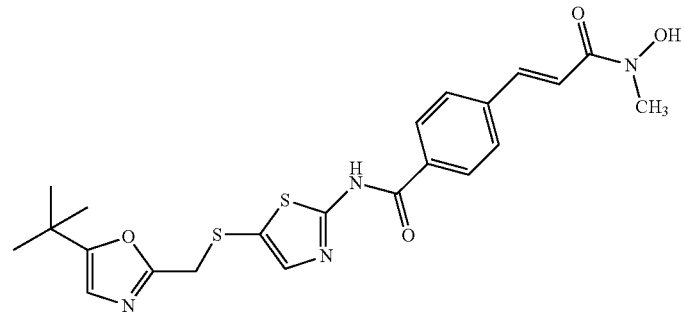 [SMILES: CN(O)C(=O)/C=C/c1ccc(C(=O)Nc2ncc(SCc3ncc(C(C)(C)C)o3)s2)cc1] |
| 40 | 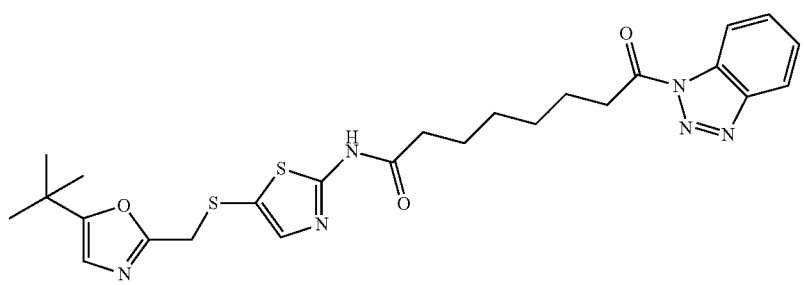 [SMILES: CC(C)(C)c1cnc(CSc2cnc(NC(=O)CCCCCCC(=O)n3nnc4ccccc43)s2)o1] |

TABLE A-continued
| Compound | Structure |
|---|---|
| 41 | 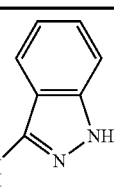 |
| 42 | 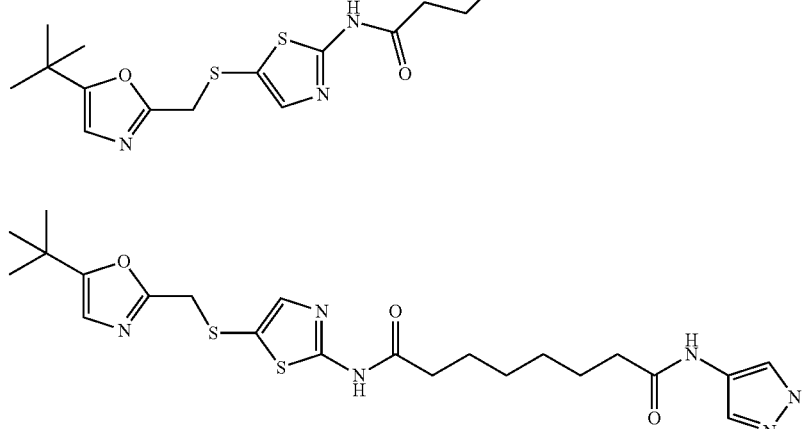 |
| 43 | 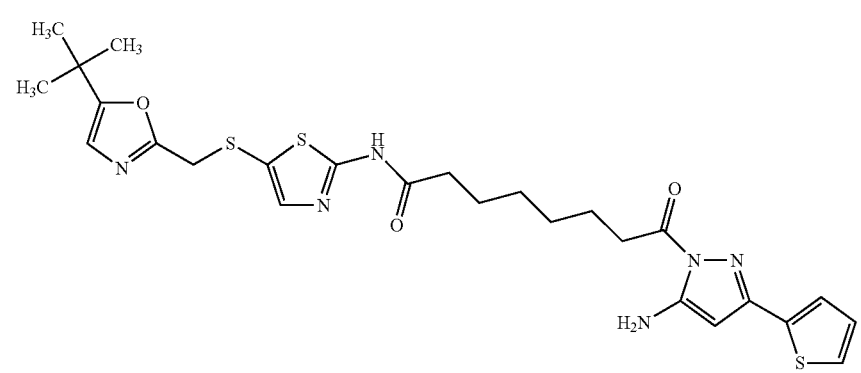 [SMILES: CC(C)(C)c1cnc(CSc2cnc(NC(=O)CCCCCCC(=O)n3nc(-c4cccs4)cc3N)s2)o1] |
| 44 | 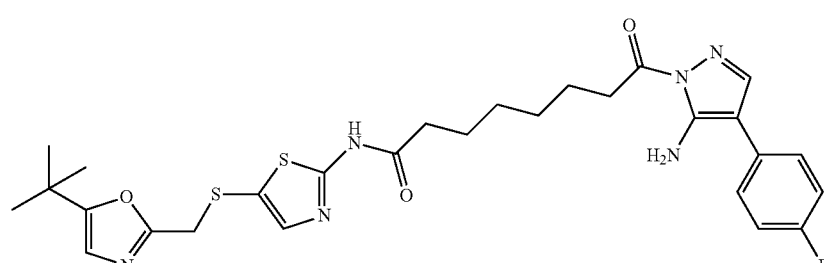 |
| 45 | 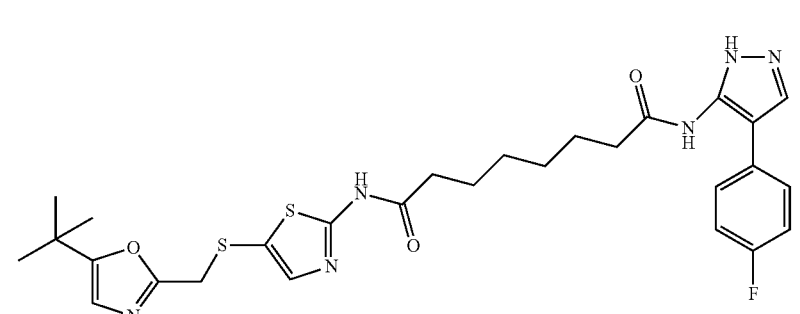 |

TABLE A-continued
| Compound | Structure |
|---|---|
| 46 | 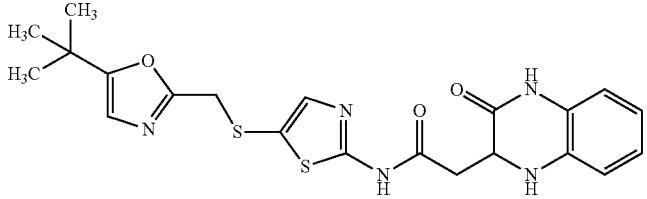 [SMILES: CC(C)(C)c1cnc(CSc2cnc(NC(=O)CC3Nc4ccccc4NC3=O)s2)o1] |
| 47 | 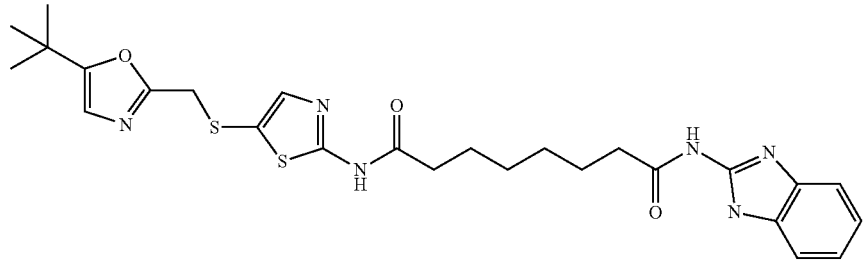 [SMILES: CC(C)(C)c1cnc(CSc2cnc(NC(=O)CCCCCCC(=O)Nc3nc4ccccc4[nH]3)s2)o1] |
| 48 | 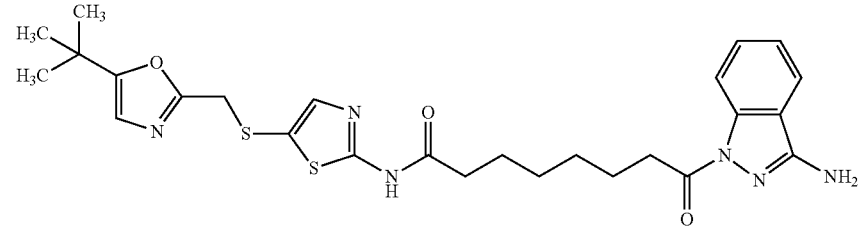 [SMILES: CC(C)(C)c1cnc(CSc2cnc(NC(=O)CCCCCCC(=O)n3nc(N)c4ccccc43)s2)o1] |
| 49 | 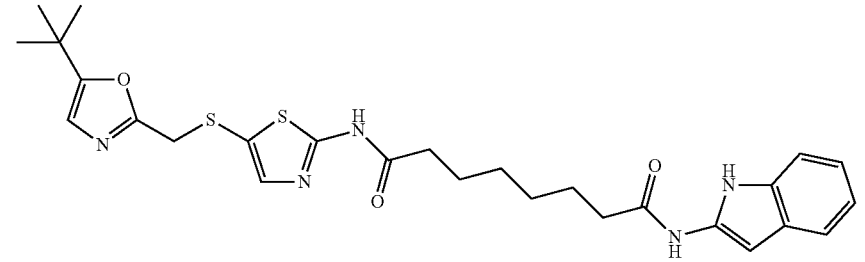 [SMILES: CC(C)(C)c1cnc(CSc2cnc(NC(=O)CCCCCCC(=O)Nc3cc4ccccc4[nH]3)s2)o1] |
| 50 | 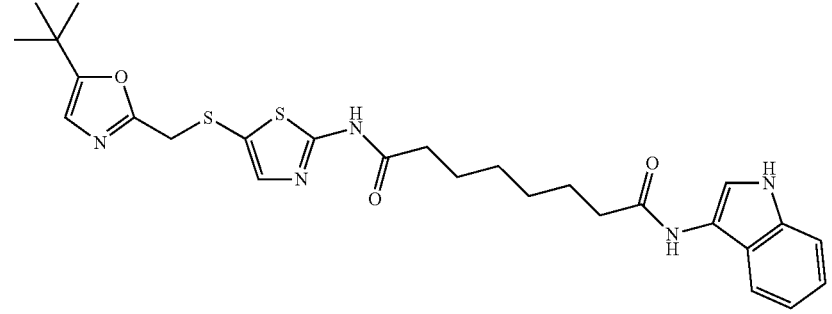 [SMILES: CC(C)(C)c1cnc(CSc2cnc(NC(=O)CCCCCCC(=O)Nc3c[nH]c4ccccc34)s2)o1] |

TABLE A-continued

| Compound | Structure |
|---|---|
| 51 | 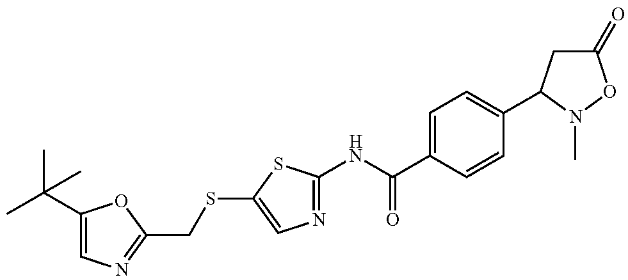 [SMILES: CN1OC(=O)CC1c1ccc(C(=O)Nc2ncc(SCc3ncc(C(C)(C)C)o3)s2)cc1] |
| 52 | 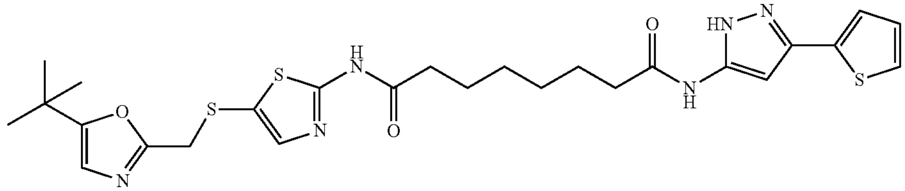 [SMILES: CC(C)(C)c1cnc(CSc2cnc(NC(=O)CCCCCCC(=O)Nc3cc(-c4cccs4)n[nH]3)s2)o1] |
| 53 | 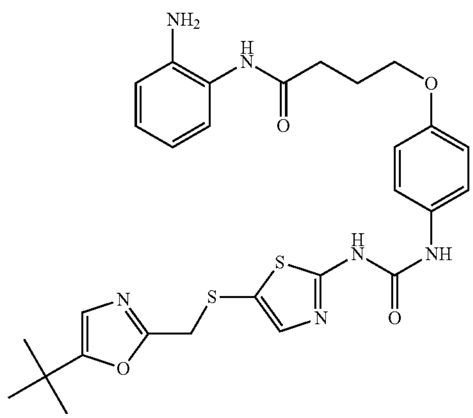 [SMILES: CC(C)(C)c1cnc(CSc2cnc(NC(=O)Nc3ccc(OCCCC(=O)Nc4ccccc4N)cc3)s2)o1] |
| 54 | 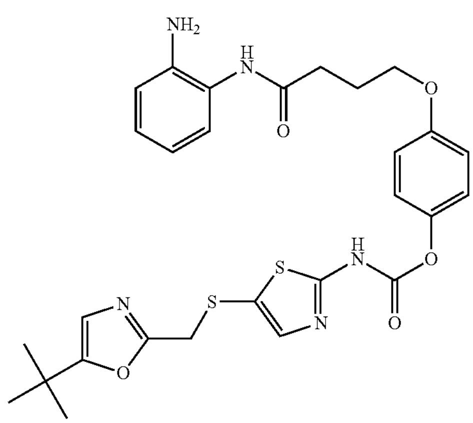 [SMILES: CC(C)(C)c1cnc(CSc2cnc(NC(=O)Oc3ccc(OCCCC(=O)Nc4ccccc4N)cc3)s2)o1] |

TABLE A-continued

| Compound | Structure |
|---|---|
| 55 | 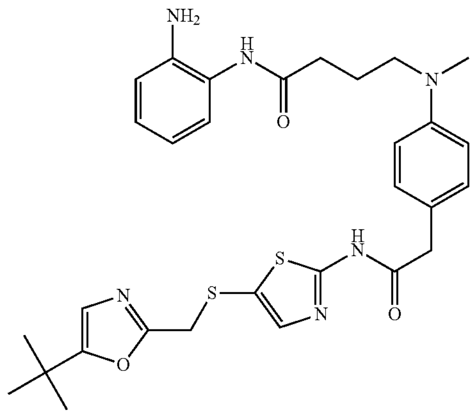 [SMILES: CN(CCCC(=O)Nc1ccccc1N)c1ccc(CC(=O)Nc2ncc(SCc3ncc(C(C)(C)C)o3)s2)cc1] |
| 56 | 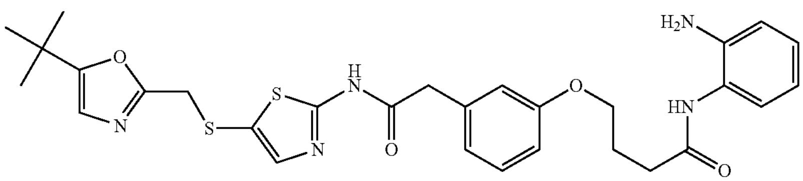 [SMILES: CC(C)(C)c1cnc(CSc2cnc(NC(=O)Cc3cccc(OCCCC(=O)Nc4ccccc4N)c3)s2)o1] |
| 57 | 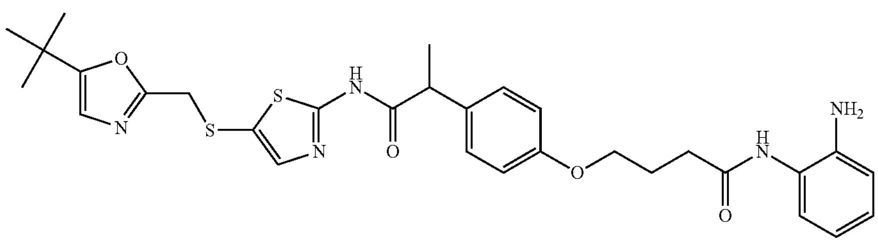 [SMILES: CC(C(=O)Nc1ncc(SCc2ncc(C(C)(C)C)o2)s1)c1ccc(OCCCC(=O)Nc2ccccc2N)cc1] |
| 58 | 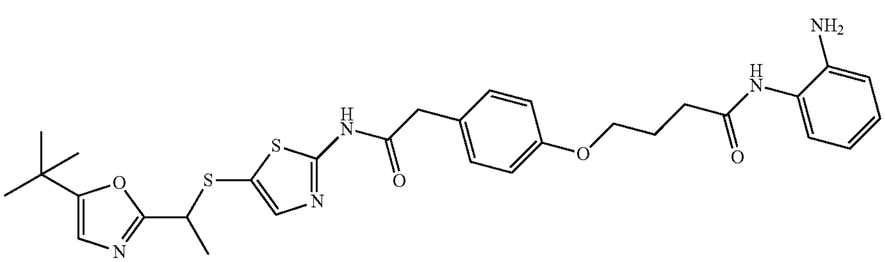 [SMILES: CC(Sc1cnc(NC(=O)Cc2ccc(OCCCC(=O)Nc3ccccc3N)cc2)s1)c1ncc(C(C)(C)C)o1] |
| 59 | 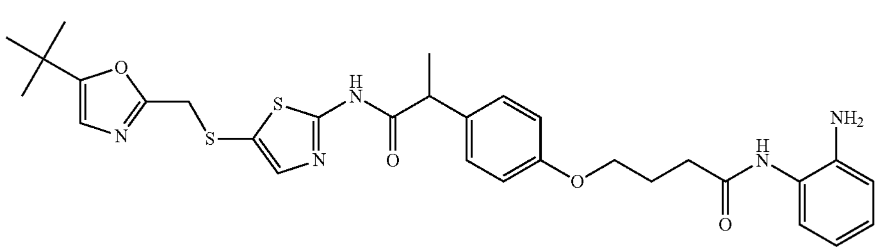 [SMILES: CC(C(=O)Nc1ncc(SCc2ncc(C(C)(C)C)o2)s1)c1ccc(OCCCC(=O)Nc2ccccc2N)cc1] |

TABLE A-continued

| Compound | Structure |
|---|---|
| 60 | 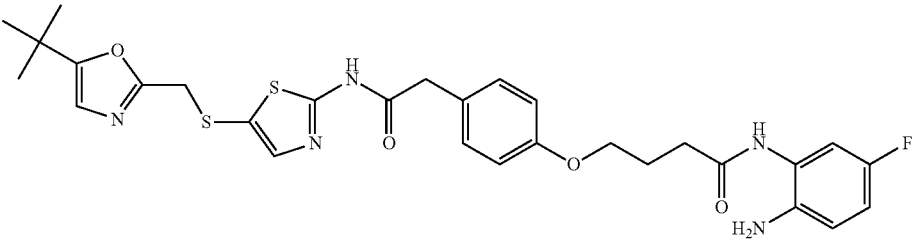 [SMILES: CC(C)(C)c1cnc(CSc2cnc(NC(=O)Cc3ccc(OCCCC(=O)Nc4cc(F)ccc4N)cc3)s2)o1] |
| 61 | 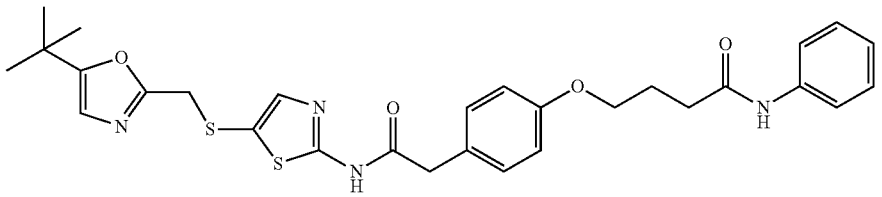 [SMILES: CC(C)(C)c1cnc(CSc2cnc(NC(=O)Cc3ccc(OCCCC(=O)Nc4ccccc4)cc3)s2)o1] |
| 62 | 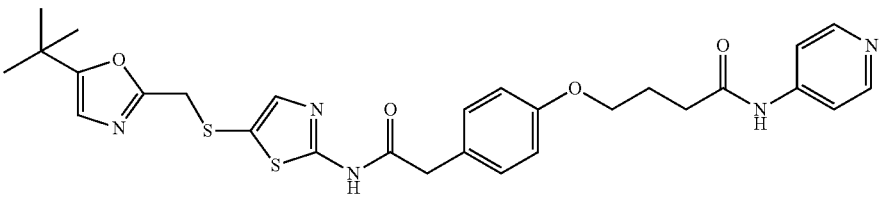 [SMILES: CC(C)(C)c1cnc(CSc2cnc(NC(=O)Cc3ccc(OCCCC(=O)Nc4ccncc4)cc3)s2)o1] |
| 63 | 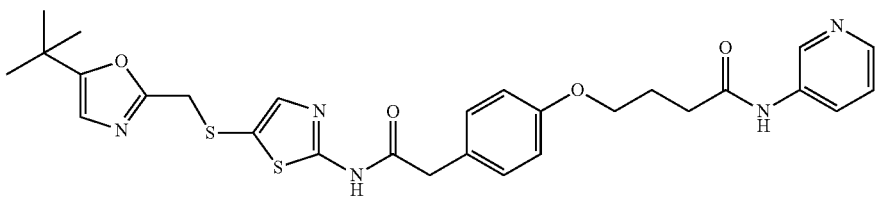 [SMILES: CC(C)(C)c1cnc(CSc2cnc(NC(=O)Cc3ccc(OCCCC(=O)Nc4cccnc4)cc3)s2)o1] |
| 64 | 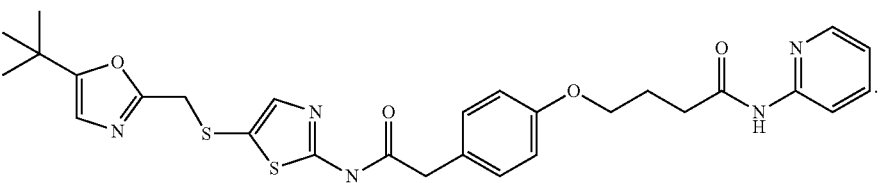 |

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Compounds of the invention, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the invention, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of the invention may also act as inhibitors of other protein kinases, e.g., protein kinase C, her2, raf 1, MEK1, MAP kinase, EGF receptor, PDGF receptor, IGF receptor, PI3 kinase, weel kinase, Src, Abl and thus be effective in the treatment of diseases associated with other protein kinases.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), and proteosomesi.

In a preferred embodiment, subject compounds may be combined with antineoplastic agents (e.g. small molecules, monoclonal antibodies, antisense RNA, and fusion proteins) that inhibit one or more biological targets such as Zolinzai, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomabi, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); antimicrotubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpes virus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welanderi) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII. Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group, when used as a linker, preferably contains between about 1 and about 24 atoms, more preferably between about 4 to about 24 atoms, more preferably between about 4-12 atoms, more typically between about 4 and about 8 atoms. An aliphatic group, when used as a substituent, preferably contains between about 1 and about 24 atoms, more preferably between about 1 to about 10 atoms, more preferably between about 1-8 atoms, more typically between about 1 and about 6 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

The term "substituted carbonyl" includes compounds and moieties which contain a carbon connected with a double bond to an oxygen atom, and tautomeric forms thereof. Examples of moieties that contain a substituted carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide).

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_8$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylherocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker B is between 1-24 atoms, preferably 4-24 atoms, preferably 4-18 atoms, more preferably 4-12 atoms, and most preferably about 4-10 atoms.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta 3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed.), "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- (α), beta- (B) and gamma- (γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds of formulae I-VI, or a pharmaceutically-acceptable salt thereof, may be prepared by any process known to be applicable to the preparation of chemically-related compounds. Suitable processes for making certain intermediates include, for example, those illustrated in U.S. Pat. No. 6,413,974. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic schemes that illustrate the methods by which the compounds of the invention may be prepared, which are intended as an illustration only and not limiting of the scope of the invention.

Scheme 1

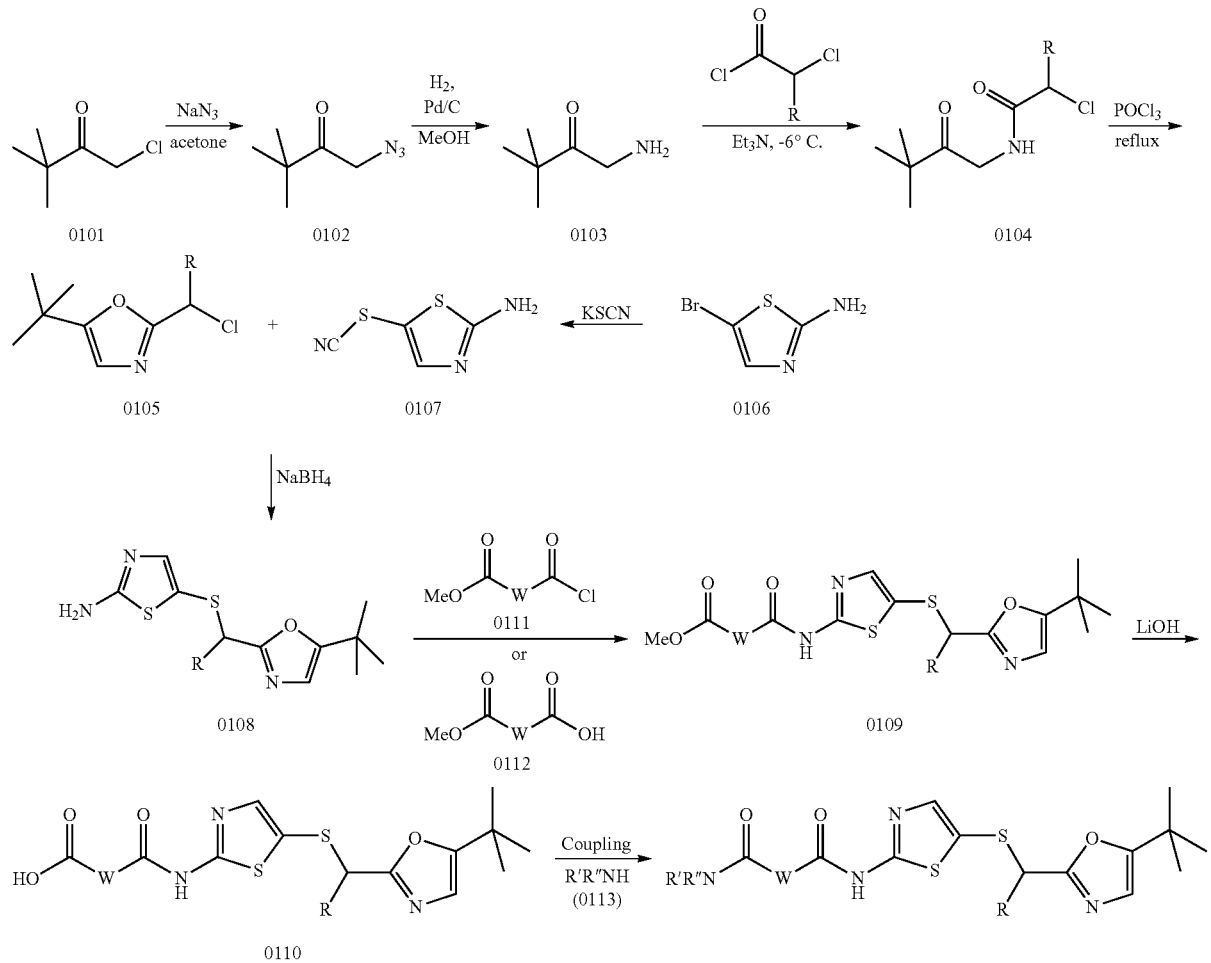

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of $N^1$-(5-((5-tert-butyloxazol-2-yl)methylthio)thiazol-2-yl)-$N^8$-methoxyoctanediamide (Compound 1)

Step 1a: α-Azidopinacolone (Compound 0102)

To a 1 L round-bottom flask fitted with a magnetic stirrer was added α-chlorpinacolone (0101, 33.5 g, 0.25 mol), acetone (400 ml) and sodium azide (21.2 g, 0.325 mol). The reaction mixture was stirred at 25° C. overnight and then filtered. The filtrate was concentrated in vacuo to provide the title compound 0102 (34.3 g, 100%) as an oil which was used to the next step without further purification. $^1$H NMR (CDCl$_3$): δ1.17 (s, 9H), 4.07 (s, 2H).

Step 1b: α-Aminopinacolone hydrochloride (Compound 0103)

To a 2 L round-bottom flask fitted with a magnetic stirrer were added compound 0102 (34.3 g, 245 mmol), methanol (1100 ml), concentrated HCl (24 ml) and 10% Pd/C (4.2 g, wet, ~40% water). The reaction mixture was stirred under hydrogen atmosphere overnight. The mixture was filtered through a pad of Celite and rinsed with methanol. The filtrate was concentrated under reduced pressure at a temperature below 40° C. The resulting wet solid was azeotroped with i-propanol (2×100 ml) and then anhydrous ether (100 ml) was added. The mixture was stirred for 5 min. The solid product was collected by filtration, washed with diethyl ether and dried in vacuo to give compound 0103 (28.0 g, 91%): $^1$H NMR (DMSO-d$^6$): δ 1.13 (s, 9H), 4.06 (s, 2H), 8.34 (s, 3H).

Step 1c: α-N-2(Chloroacetylamino)pinacolone (Compound 0104-1)

Triethylamine (35 ml, 250 mmol) was added to a cooled solution (−5° C.) of compound 0103 in CH$_2$Cl$_2$(350 ml). To the resulting mixture which had been cooled to −10° C. was added a solution of α-chloroacetyl chloride (8.8 ml, 110 mmol) in CH$_2$Cl$_2$ (20 ml) dropwise over 15 min period while keeping the reaction temperature below −5° C. The reaction mixture was stirred for 1 h and quenched with 1 N HCl (200 ml). The organic phase was separated and washed with 1 N HCl (200 ml) and water (50 ml). The organic layer was dried (Na$_2$SO$_4$), filtered and evaporated to afford compound 0104-1 (18.9 g, 98%) as a white solid: $^1$H NMR (CDCl$_3$): δ 1.21 (s, 9H), 4.09 (s, 2H), 4.30 (s, 2H), 7.35 (s, 1H).

Step 1d: 5-tert-Butyl-2-chloromethyloxazole (Compound 0105-1)

To a 100 ml round-bottom flask fitted with a magnetic stirrer were added compound 0104-1 (9.534 g, 49.9 mmol) and POCl$_3$ (30 ml). The reaction mixture was heated to 105° C. and stirred for 1 h. After being cooled to room temperature, the reaction mixture was poured carefully into ice. The mixture was extracted with ether for six times. The organic extracts were combined and mixed with saturated sodium bicarbonate to keep the pH at 7-8. The organic phase was separated and washed successively with saturated sodium bicarbonate, water and brine. The organic phase was then dried over MgSO4 and concentrated in vacuo to provide crude material which was distilled under reduced pressure to give the title compound 0105-1 (7.756 g, 70%) as a colorless oil: bp. 49° C./0.25 mmHg. $^1$H NMR (CDCl$_3$): δ 1.32 (s, 9H), 4.60 (s, 2H), 6.70 (s, 1H).

Step 1e: 5-Thiocyanatothiazol-2-amine (Compound 0107)

A mixture of 2-amino-5-bromothiazole hydrobromide (0106, 53.0 g, 0.204 mol) and potassium thiocyanate (78.5 g, 0.808 mol) in methanol (1.4 L) was stirred at room temperature for 20 h. Methanol was evaporated and water (180 ml) was added. The pH of the aqueous solution was adjusted to pH=12 with 10% NaOH and precipitate formed. The solid was collected by filtration to yield compound 0107 (14.0 g, 44%) as a brownish solid: LCMS: 157 [M+1]$^+$.

Step 1f: 5-((5-tert-Butyloxazol-2-yl)methylthio)thiazol-2-amine (compound 0108-1)

To a solution of compound 0107 (3.14 g, 20 mmol) in absolute EtOH (200 ml) was added NaBH$_4$(1.6 g, 40 mmol) portionwise at room temperature. The mixture was stirred for 1 h, and then acetone (100 ml) was slowly introduced. After 1 h, a solution of compound 0105-1 (3.5 g, 20 mmol) in EtOH (30 ml) was added. The resulting dark reaction mixture was heated to reflux for 1 h, and was then cooled and concentrated in vacuo. The residue was partitioned between EtOAc and brine. The organic phase was separated, dried (MgSO$_4$), and concentrated in vacuo to give a crude solid which was triturated with diethyl ether/hexane to provide compound 0108-1 (3.1 g, 57%) as a pale red-brown solid: LCMS: 270 [M+1]$^+$.

Step 1g: Methyl 8-(5-(1-(5-tert-butyloxazol-2-yl) methylthio)thiazol-2-ylamino)-8-oxooctanoate (Compound 0109-1)

To the solution of compound 0108-1 (283 mg, 0.35 mmol) and TEA (0.5 mL) in THF (20 mL) was added dropwise at 0° C. a solution of methyl 8-chloro-8-oxooctanoate (0.4 g, 0.7 mmol) in THF (10 mL). The reaction mixture was stirred at r.t. for 2 h. Solvent was removed under reduced pressure, and the residue was diluted in water and extracted with CH$_2$Cl$_2$ (3×50 mL). The organic layer was washed with water (3×50 mL), brine (1×50 mL), dried over anhydrous Na$_2$SO$_4$, and concentrated to get the product 0109-1 as brown oil (300 mg, 66%): LCMS: 454 [M+1]$^+$.

Step 1h: 8-(5-((5-tert-Butyloxazol-2-yl)methylthio) thiazol-2-ylamino)-8-oxooctanoic acid (Compound 0110-1)

To the solution of compound 0109-1 (6.23 g, 14.19 mmol) in methanol (100 mL) and water (50 mL) was added LiOH (5.92 g, 140.95 mmol). The mixture was stirred at 25° C. for 2 hours and was then concentrate. The residue was dissolved in water and adjusted to pH 4 with HCl (10%) to produce a precipitate. The solid was filtered and dried to get the compound 0110-1 (5.10 g, 85%) as a white solid: LCMS: 426 [M+1]+. $^1$H NMR (400 MHz. DMSO-$d_6$) δ 1.18 (s, 9H), 1.26 (m, 4H), 1.48 (m, 2H), 1.56 (m, 2H), 2.19 (t, J=7.2 Hz, 2H), 2.40 (t, J=7.2 Hz, 2H), 4.06 (s, 2H), 6.71 (s, 1H), 7.38 (s, 1H), 11.98 (s, 1H), 12.21 (s, 1H).

Step 1i: $N^1$-(5-((5-tert-Butyloxazol-2-yl)methylthio) thiazol-2-yl)-$N^8$-methoxyoctane-diamide (Compound 1)

The mixture of compound 0110-1 (200 mg, 0.47 mmol), EDCI.HCl (136 mg, 0.71 mmol), HOBt (99 mg, 0.71 mmol), NEt$_3$ (2 mL) and methoxylamine hydrochloride (79 mg, 0.94 mmol) in DMF (3 mL) was stirred for 16 hours at 30° C. The solvent was removed under reduced pressure and the residue was dissolved in CH$_2$Cl$_2$ (150 mL). The organic layer was washed with water (3×50 mL), brine (1×50 mL), dried and concentrated to get the crude product which was purified by prep.TLC (methanol in dichloromethane (5% v/v)) to obtain compound 1 (36 mg, 17%) as a white solid: LCMS: 455 [M+1]+. $^1$H-NMR (400 MHz. DMSO-$d_6$) δ 1.18 (s, 9H), 1.24 (m, 4H), 1.48 (m, 2H), 1.56 (m, 2H), 1.92 (t, J=7.2 Hz, 2H), 2.39 (t, J=7.2 Hz, 2H), 3.56 (s, 3H), 4.05 (s, 2H), 6.71 (s, 1H), 7.37 (s, 1H), 10.93 (s, 1H), 12.21 (s, 1H).

Example 2

Preparation of $N^1$-(benzyloxy)-$N^8$-(5-((5-tert-butyloxazol-2-yl)methylthio)thiazol-2-yl)octanediamide (Compound 2)

The title compound 2 (70 mg, 37%) as a white solid was synthesized from compound 0110-1 (150 mg, 0.35 mmol), EDCI.HCl (135 mg, 0.71 mmol), HOBt (95 mg, 0.71 mmol), DIPEA (228 mg, 1.77 mmol), O-benzyl hydroxylamine hydrochloride (113 mg, 0.71 mmol), and DMF (3 mL) using the procedure similar to that described for compound 1 (Example 1). LCMS: 531 [M+1]+; $^1$H-NMR (400 MHz. DMSO-$d_6$) δ 1.18 (s, 9H), 1.28 (m, 4H), 1.47 (m, 2H), 1.56 (m, 2H), 1.94 (t, J=7.2 Hz, 2H), 2.39 (t, J=7.2 Hz, 2H), 4.05 (s, 2H), 4.77 (s, 2H), 6.71 (s, 1H), 7.38 (m, 6H), 10.93 (s, 1H), 12.21 (s, 1H).

Example 3

Preparation of $N^1$-(5-((5-tert-butyloxazol-2-yl)methylthio)thiazol-2-yl)-$N^8$-(tetrahydro-2H-pyran-2-yloxy)octanediamide (Compound 3)

The title compound 3 (71 mg, 38%) as a white solid was synthesized from compound 0110-1 (150 mg, 0.35 mmol), EDCI.HCl (135 mg, 0.71 mmol), HOBt (95 mg, 0.71 mmol), DIPEA (228 mg, 1.77 mmol), O-(tetrahydro-2H-pyran-2-yl) hydroxylamine hydrochloride (83 mg, 0.71 mmol), and DMF (3 mL) using the procedure similar to that described for compound 1 (Example 1). LCMS: 525 [M+1]+. $^1$H-NMR (400 MHz. DMSO-$d_6$) δ 1.18 (s, 9H), 1.24 (m, 4H), 1.49 (m, 6H), 1.64 (m, 4H), 1.97 (t, J=7.2 Hz, 2H), 2.40 (t, J=7.2 Hz, 2H), 3.49 (m, 1H), 3.91 (m, 1H), 4.05 (s, 2H), 4.79 (s, 1H), 6.72 (s, 1H), 7.38 (s, 1H), 10.90 (s, 1H), 12.22 (s, 1H).

Example 4

Preparation of $N^1$-(5-((5-tert-butyloxazol-2-yl)methylthio)thiazol-2-yl)-$N^8$-hydroxy-$N^8$-methyloctanediamide (Compound 4)

A solution of compound 0110-1 (150 mg, 0.35 mmol), TBTU (567 mg, 1.77 mmol), $N^1,N^2$-diisopropylethane-1,2-diamine (364 mg, 2.82 mmol) and N-methylhydroxylamine hydrochloride (147 mg, 1.77 mmol) in DMF (3 mL) was stirred at 50° C. for 16 hours. The solvent was removed under reduced pressure, and the residue was dissolved in water and extracted with CH$_2$Cl$_2$ (3×50 mL). The organic layer was washed with water (3×50 mL), brine (1×50 mL), dried over anhydrous NaSO$_4$, and concentrated to get the crude product which was purified by prep.-TLC [petroleum ether in Ethyl acetate (9% v/v)] to obtain compound 4 as a pale white solid (59 mg, 37%). LCMS: 455 [M+1]+. $^1$H-NMR (500 MHz. DMSO-$d_6$) δ 1.18 (s, 9H), 1.26 (m, 4H), 1.47 (m, 2H), 1.56 (m, 2H), 2.32 (t, J=7.0 Hz, 2H), 2.40 (t, J=7.0 Hz, 2H), 3.07 (s, 3H), 4.05 (s, 2H), 6.72 (s, 1H), 7.38 (s, 1H), 9.75 (s, 1H), 12.22 (s, 1H).

Example 5

Preparation of $N^1$-(5-((5-tert-butyloxazol-2-yl)methylthio)thiazol-2-yl)-$N^8$-hydroxy-$N^8$-isopropyloctanediamidei (Compound 5)

Step 5a: $N^1$-(5-((5-tert-butyloxazol-2-yl)methylthio) thiazol-2-yl)-$N^8$-hydroxy-$N^8$-isopropyloctanediamide (Compound 5)

The title compound 5 (30 mg, 18%) as a yellow solid was synthesized from compound 0110-1 (150 mg, 0.35 mmol), TBTU (680 mg, 2.12 mmol), $N^1,N^2$-diisopropylethane-1,2-diamine (728 mg, 5.65 mmol), N-isopropylhydroxylamine hydrochloride (394 mg, 3.53 mmol) and DMF (3 mL) using the procedure similar to that described for compound 4 (Example 4). LCMS: 483 [M+1]+; $^1$H-NMR (500 MHz. DMSO-$d_6$) δ 1.03 (d, J=6.5 Hz, 6H), 1.18 (s, 9H), 1.26 (m, 4H), 1.47 (m, 2H), 1.57 (m, 2H), 2.30 (t, J=7.5 Hz, 2H), 2.40 (t, J=7.5 Hz, 2H), 4.05 (s, 2H), 4.52 (s, 1H), 6.72 (s, 1H), 7.38 (s, 1H), 9.20 (s, 1H), 12.22 (s, 1H).

Example 6

Preparation of $N^1$-benzyl-$N^8$-(5-((5-tert-butyloxazol-2-yl)methylthio)-thiazol-2-yl)-$N^1$-hydroxyoctanediamide (Compound 6)

The title compound 6 (38 mg, 20%) as a yellow oil was synthesized from compound 0110-1 (150 mg, 0.35 mmol), TBTU (340 mg, 1.06 mmol), $N^1,N^2$-diisopropylethane-1,2-diamine (364 mg, 2.82 mmol), N-benzylhydroxylamine hydrochloride (282 mg, 1.77 mmol) and DMF (3 mL) using the procedure similar to that described for compound 4 (Example 4). LCMS: 531 [M+1]+. $^1$H-NMR (500 MHz. DMSO-$d_6$) δ 1.18 (s, 9H), 1.28 (m, 4H), 1.52 (m, 2H), 1.57 (m, 2H), 2.41 (m, 4H), 4.05 (s, 2H), 4.68 (s, 2H), 6.71 (s, 1H), 7.25 (m, 3H), 7.33 (m, 2H), 7.38 (s, 1H), 9.84 (s, 1H), 12.24 (s, 1H).

Example 7

Preparation of $N^1$-(5-((5-tert-butyloxazol-2-yl)methylthio)thiazol-2-yl)-$N^8$-(2-hydroxyethoxy)octanediamide (Compound 7)

$N^1$-(5-((5-tert-butyloxazol-2-yl)methylthio)thiazol-2-yl)-1V-(2-(vinyloxy)-ethoxy)-octanediamide (92 mg, 90%) as a white solid was synthesized from compound 0110-1 (85 mg, 0.20 mmol), TBTU (128 mg, 0.40 mmol), $N^1,N^2$-diisopropylethane-1,2-diamine (77 mg, 0.60 mmol), O-(2-vinyloxyethyl)-hydroxylamine (41 mg, 0.40 mmol) and DMF (1 mL)

using the procedure similar to that described for compound 4 (Example 4). LCMS: 511 [M+1]$^+$.

To the solution of above N$^1$-(5-((5-tert-butyloxazol-2-yl)methylthio)thiazol-2-yl)-N$^8$-(2-(vinyloxy)-ethoxy)-octanediamide (92 mg, 0.18 mmol) in methanol (3 mL) was added 1M HCl (2 mL). The mixture was stirred at room temperature for 30 minutes. The solvent was removed and the residue was dissolved in CH$_2$Cl$_2$ (100 mL). The organic layer was washed with saturated NaHCO$_3$, brine, dried and concentrated. The crude product was purified by prep.-TLC [methanol in ethyl acetate (2.5% v/v)] to give compound 7 (44 mg, 51%) as a light yellow solid. LCMS: 485 [M+1]$^+$; $^1$H-NMR (400 MHz. DMSO-d$_6$) δ 1.18 (s, 9H), 1.25 (m, 4H), 1.48 (m, 2H), 1.56 (m, 2H), 1.96 (t, J=7.2 Hz, 2H), 2.39 (t, J=7.2 Hz, 2H), 3.51 (t, J=4.8 Hz, 2H), 3.76 (t, J=4.8 Hz, 2H), 4.05 (s, 2H), 6.71 (s, 1H), 7.37 (s, 1H).

Example 8

Preparation of N$^1$-(5-((5-tert-butyloxazol-2-yl)methylthio)thiazol-2-yl)-N$^8$-(4-(2-hydroxyethyl)phenyl)octanediamide (Compound 8)

The title compound 8 (75 mg, 75%) as a pale white solid was synthesized from compound 0110-1 (85 mg, 0.20 mmol), TBTU (128 mg, 0.40 mmol), N$^1$,N$^2$-diisopropylethane-1,2-diamine (77 mg, 0.60 mmol), 2-(4-aminophenyl)ethanol (55 mg, 0.40 mmol), and DMF (1 mL) using the procedure similar to that described for compound 4 (Example 4). LCMS: 545 [M+1]$^+$. $^1$H-NMR (500 MHz. DMSO-d$_6$) δ 1.17 (s, 9H), 1.29 (m, 4H), 1.58 (m, 4H), 2.27 (t, J=7.5 Hz, 2H), 2.40 (t, J=7.5 Hz, 2H), 2.65 (t, J=7.0 Hz, 2H), 3.55 (t, J=7.0 Hz, 2H), 4.04 (s, 2H), 4.60 (s, 1H), 6.71 (s, 1H), 7.10 (d, J=8.5 Hz, 2H), 7.36 (s, 1H), 7.50 (d, J=8.5 Hz, 2H), 9.79 (s, 1H), 12.22 (s, 1H).

Example 9

Preparation of N$^1$-(5-((5-tert-butyloxazol-2-yl)methylthio)thiazol-2-yl)-N$^8$-phenyloctanediamide (Compound 9)

The title compound 9 (75 mg, 75%) as a white solid was synthesized from compound 0110-1 (85 mg, 0.20 mmol), TBTU (128 mg, 0.40 mmol), N$^1$,N$^2$-diisopropylethane-1,2-diamine (77 mg, 0.60 mmol), aniline (37 mg, 0.40 mmol), and DMF (1 mL) using the procedure similar to that described for compound 4 (Example 4). LCMS: 501 [M+1]$^+$. $^1$H-NMR (400 MHz. DMSO-d$_6$) δ 1.17 (s, 9H), 1.30 (m, 4H), 1.58 (m, 4H), 2.29 (t, J=7.2 Hz, 2H), 2.40 (t, J=7.2 Hz, 2H), 4.05 (s, 2H), 6.71 (s, 1H), 7.01 (m, 1H), 7.27 (m, 2H), 7.37 (s, 1H), 7.58 (m, 2H), 9.87 (s, 1H), 12.23 (s, 1H).

Example 10

Preparation of N$^1$-(5-((5-tert-butyloxazol-2-yl)methylthio)thiazol-2-yl)-N$^8$-(4-hydroxyphenyl)octanediamide (Compound 10)

The title compound 10 (44 mg, 43%) as a yellow solid was synthesized from compound 0110-1 (85 mg, 0.20 mmol), TBTU (128 mg, 0.40 mmol), N$^1$,N$^2$-diisopropylethane-1,2-diamine (77 mg, 0.60 mmol), 4-aminophenol (44 mg, 0.40 mmol) and DMF (1 mL) using the procedure similar to that described for compound 4 (Example 4). LCMS: 517 [M+1]$^+$. $^1$H-NMR (400 MHz. DMSO-d$_6$) δ 1.18 (s, 9H), 1.29 (m, 4H), 1.56 (m, 4H), 2.23 (t, J=7.2 Hz, 2H), 2.40 (t, J=7.2 Hz, 2H), 4.05 (s, 2H), 6.66 (d, J=8.8 Hz, 2H), 6.71 (s, 1H), 7.34 (d, J=8.8 Hz, 2H), 7.37 (s, 1H), 9.14 (s, 1H), 9.59 (s, 1H), 12.22 (s, 1H).

Example 11

Preparation of N1-(2-aminophenyl)-N3-(5-((5-tert-butyloxazol-2-yl)methylthio)thiazol-2-yl)malonamide (compound 13)

Step 11a: Methyl 3-(5-((5-tert-butyloxazol-2-yl)methylthio)thiazol-2-ylamino)-3-oxopropanoate (Compound 0109-13)

The title compound 0109-13 (400 mg, 100%) as a yellow oil was synthesized from 0108-1 (269 mg, 1 mmol), 3-methoxy-3-oxopropanoic acid (528 mg, 4 mmol), TBTU (1.28 g, 4 mmol), DIPEA (516 mg, 4 mmol) and DMF (5 mL) using the procedure similar to that described for compound 4 (Example 4). LCMS: 370 [M+1]$^+$.

Step 11b: 3-(5-((5-Tert-Butyloxazol-2-yl)methylthio)thiazol-2-ylamino)-3-oxopropanoic acid (Compound 0110-13)

To the solution of compound 0109-13 (400 mg,) in methanol (2 mL), THF (2 mL), and water (2 mL) was added LiOH (126 mg, 3 mmol). The resulting mixture was stirred at 25° C. for 1 h. The solvent was removed in vacuo and the residue was dissolved in water and adjusted to pH 4 with 10% HCl. The solid was filtered and dried to give the title compound 0110-13 (165 mg, 46%, two steps) as a white solid. LCMS: 356 [M+1]$^+$. $^1$H NMR (400 MHz, DMSO-d$_6$) δ 1.20 (s, 9H), 3.48 (s, 2H), 4.08 (s, 2H), 6.71 (s, 1H), 7.41 (s, 1H), 12.41 (s, 1H).

Step 11c: N1-(2-Aminophenyl)-N-3-(5-((5-tert-butyloxazol-2-yl)methylthio)thiazol-2-yl)malonamide (Compound 13)

The title compound 13 (58 mg, 28%) as a yellow solid was synthesized from compound 0110-13 (165 mg, 0.46 mmol), benzene-1,2-diamine (149 mg, 1.38 mmol), TBTU (289 mg, 0.92 mmol), DIPEA (178 mg, 1.38 mmol) and DMF (5 mL) using the procedure similar to that described for compound 4 (Example 4). mp 115-116° C. LCMS: 446 [M+1]$^+$. $^1$H-NMR (400 MHz, DMSO-d$_6$) δ 1.20 (s, 9H), 3.60 (s, 2H), 4.08 (s, 2H), 4.95 (s, 2H), 6.52 (m, 1H), 6.72 (m, 2H), 6.92 (m, 1H), 7.12 (m, 1H), 7.41 (s, 1H), 9.37 (s, 1H), 12.44 (s, 1H).

Example 12

Preparation of N1-(2-aminophenyl)-N4-(5-((5-tert-butyloxazol-2-yl)methylthio)thiazol-2-yl)succinamide (Compound 14)

Step 12a: Methyl 4-(5-((5-tert-butyloxazol-2-yl)methylthio)thiazol-2-ylamino)-4-oxobutanoate (Compound 0109-14)

The title compound 0109-14 (250 mg, 65%) as a yellow solid was synthesized from 0108-1 (269 mg, 1 mmol), 4-methoxy-4-oxobutanoic acid (264 mg, 2 mmol), TBTU (642 mg, 2 mmol), DIPEA (387 mg, 3 mmol) and DMF (5 mL) using the procedure similar to that described for compound 0109-13. LCMS: 384 [M+1]$^+$; $^1$H NMR (400 MHz, DMSO-d$_6$) δ 1.19 (s, 9H), 2.62 (t, J=6.8 Hz, 2H), 2.70 (t, J=6.8 Hz, 2H), 3.59 (s, 3H), 4.06 (s, 2H), 6.71 (s, 1H), 7.36 (s, 1H), 12.32 (s, 1H).

Step 12b: 4-(5-((5-tert-Butyloxazol-2-yl)methylthio) thiazol-2-ylamino)-4-oxobutanoic acid (Compound 0110-14)

The title compound 0110-14 (150 mg, 65%) as a white solid was synthesized from compound 0109-14 (240 mg, 0.63 mmol) using the procedure similar to that described for compound 0110-13 (Example 11). LCMS: 370 [M+1]$^+$. $^1$H NMR (400 MHz, DMSO-d$_6$) δ 1.19 (s, 9H), 2.54 (t, J=6.8 Hz, 2H), 2.64 (t, J=6.8 Hz, 2H), 4.05 (s, 2H), 6.71 (s, 1H), 7.37 (s, 1H), 12.22 (s, 1H), 12.30 (s, 1H).

Step 12c: N1-(2-aminophenyl)-N4-(5-((5-tert-butyloxazol-2-yl)methylthio)thiazol-2-yl)succinamide (Compound 14)

The title compound 14 (41 mg, 22%) as a yellow solid was synthesized from compound 0110-14 (150 mg, 0.41 mmol) using the procedure similar to that described for compound 4 (Example 4). mp 131-132° C. LCMS: 460 [M+1]$^+$. $^1$H-NMR (400 MHz, DMSO-d$_6$) δ 1.19 (s, 9H), 2.69 (t, J=6.8 Hz, 2H), 2.72 (t, J=6.8 Hz, 2H), 4.05 (s, 2H), 4.87 (s, 2H), 6.51 (m, 1H), 6.72 (m, 2H), 6.89 (m, 1H), 7.14 (m, 1H), 7.37 (s, 1H), 9.21 (s, 1H), 12.31 (s, 1H).

Example 13

Preparation of N1-(2-aminophenyl)-N5-(5-((5-tert-butyloxazol-2-yl)methylthio)thiazol-2-yl)glutaramide (Compound 15)

Step 13a: Methyl 5-(5-((5-tert-butyloxazol-2-yl)methylthio)thiazol-2-ylamino)-5-oxopentanoate (Compound 0109-15)

The title compound 0109-15 (500 mg, 77%) as a yellow solid was synthesized from 0108-1 (440 mg, 1.64 mmol), 5-methoxy-5-oxopentanoic acid (718 mg, 4.98 mmol), TBTU (1.05 g, 3.28 mmol), DIPEA (642 mg, 4.98 mmol) and DMF (5 mL) using the procedure similar to that described for compound 0109-13: LCMS: 398 [M+1]$^+$: $^1$H NMR (400 MHz, DMSO-d$_6$) δ 1.18 (s, 9H), 1.83 (m, 2H), 2.34 (t, J=6.8 Hz, 2H), 2.46 (t, J=6.8 Hz, 2H), 3.59 (s, 3H), 4.05 (s, 2H), 6.71 (s, 1H), 7.38 (s, 1H), 12.23 (s, 1H).

Step 13b: 5-(5-((5-tert-Butyloxazol-2-yl)methylthio) thiazol-2-ylamino)-5-oxopentanoic acid (Compound 0110-15)

The title compound 0110-15 (480 mg, 100%) as a white solid was synthesized from compound 0109-15 (500 mg, 1.26 mmol) using the procedure similar to that described for compound 0110-13 (example 11). LCMS: 384 [M+1]$^+$; $^1$H NMR (400 MHz, DMSO-d$_6$) δ 1.18 (s, 9H), 1.80 (m, 2H), 2.26 (t, J=6.8 Hz, 2H), 2.48 (t, J=6.8 Hz, 2H), 4.05 (s, 2H), 6.71 (s, 1H), 7.38 (s, 1H), 12.24 (s, 1H).

Step 13c: N1-(2-Aminophenyl)-N-5-(5-((5-tert-butyloxazol-2-yl)methylthio)thiazol-2-yl)glutaramide (Compound 15)

The title compound 15 (50 mg, 20%) as a yellow solid was synthesized from compound 0110-15 (200 mg, 0.52 mmol) using the procedure similar to that described for compound 4 (Example 4). m.p.: 119-120° C. LCMS: 474 [M+1]$^+$. $^1$H-NMR (400 MHz, DMSO-d$_6$) δ 1.19 (s, 9H), 1.90 (m, 2H), 2.36 (t, J=6.8 Hz, 2H), 2.49 (t, J=6.8 Hz, 2H), 4.06 (s, 2H), 6.52 (m, 1H), 6.72 (m, 2H), 6.89 (m, 1H), 7.14 (m, 1H), 7.38 (s, 1H), 9.13 (s, 1H), 12.29 (s, 1H).

Example 14

Preparation of N1-(2-aminophenyl)-N6-(5-((5-tert-butyloxazol-2-yl)methylthio)thiazol-2-yl)adipamide (Compound 16)

Step 14a: Methyl 6-(5-((5-tert-butyloxazol-2-yl)methylthio)thiazol-2-ylamino)-6-oxohexanoate (Compound 0109-16)

The title compound 0109-16 (300 mg, 73%) as a yellow solid was synthesized from 0108-1 (440 mg, 1.64 mmol), 6-methoxy-6-oxohexanoic acid (320 mg, 2 mmol), TBTU (1.05 g, 3.28 mmol), DIPEA (642 mg, 4.98 mmol) and DMF (5 mL) using the procedure similar to that described for compound 0109-13 (Example 11). LCMS: 412 [M+1]$^+$. $^1$H NMR (400 MHz, DMSO-d$_6$) δ 1.18 (s, 9H), 1.55 (m, 4H), 2.32 (m, 2H), 2.43 (m, 2H), 3.58 (s, 3H), 4.06 (s, 2H), 6.72 (s, 1H), 7.38 (s, 1H), 12.24 (s, 1H).

Step 14b: 6-(5-((5-tert-Butyloxazol-2-yl)methylthio) thiazol-2-ylamino)-6-oxohexanoic acid (Compound 0110-16)

The title compound 0110-16 (190 mg, 100%) as a white solid was synthesized from compound 0109-16 (200 mg, 0.49 mmol) using the procedure similar to that described for compound 0110-13 (example 11). LCMS: 398 [M+1]$^+$. $^1$H NMR (400 MHz, DMSO-d$_6$) δ 1.18 (s, 9H), 1.50 (m, 2H), 1.59 (m, 2H), 2.22 (m, 2H), 2.42 (m, 2H), 3.17 (s, 1H), 4.06 (s, 2H), 6.71 (s, 1H), 7.38 (s, 1H), 12.24 (s, 1H).

Step 14c: N1-(2-Aminophenyl)-N6-(5-((5-tert-butyloxazol-2-yl)methylthio)thiazol-2-yl)adipamide (Compound 16)

The title compound 16 (50 mg, 23%) as a yellow solid was synthesized from compound 0110-16 (180 mg, 0.52 mmol) using the procedure similar to that described for compound 4 (Example 4): m.p. 110-111° C. LCMS: 488 [M+1]$^+$. $^1$H-NMR (400 MHz, DMSO-d$_6$) δ 1.18 (s, 9H), 1.62 (m, 4H), 2.33 (m, 2H), 2.46 (m, 2H), 4.06 (s, 2H), 4.83 (s, 2H), 6.52 (m, 1H), 6.72 (m, 2H), 6.89 (m, 1H), 7.14 (m, 1H), 7.39 (s, 1H), 9.12 (s, 1H), 12.27 (s, 1H).

Example 15

Preparation of N1-(2-aminophenyl)-N7-(5-((5-tert-butyloxazol-2-yl)methylthio)thiazol-2-yl)heptanediamide (Compound 17)

Step 15a: 7-(5-((5-Tert-butyloxazol-2-yl)methylthio) thiazol-2-ylamino)-7-oxoheptanoic acid (compound 0109-17)

The title compound 0109-17 (90 mg, 21%) as a yellow solid was synthesized from compound 0108-1 (440 mg, 1.64 mmol) and 7-methoxy-7-oxoheptanoic acid (348 mg, 2 mmol) using the procedure similar to that described for compound 0109-13 (Example 11): LCMS: 426 [M+1]$^+$; $^1$H NMR (400 MHz, DMSO-$d_6$) δ 1.18 (s, 9H), 1.56 (m, 6H), 2.29 (m, 2H), 2.39 (m, 2H), 3.58 (s, 3H), 4.06 (s, 2H), 6.71 (s, 1H), 7.38 (s, 1H), 12.21 (s, 1H).

Step 15b: 7-(5-((5-Tert-butyloxazol-2-yl)methylthio) thiazol-2-ylamino)-7-oxoheptanoic acid (Compound 0110-17)

The title compound 0110-17 (80 mg, 100%) as a white solid was synthesized from compound 0109-17 (80 mg, 0.19 mmol) using the procedure similar to that described for compound 0110-13 (Example 11): LCMS: 412 [M+1]$^+$. $^1$H NMR (400 MHz, DMSO-$d_6$) δ 1.18 (s, 9H), 1.28 (m, 2H), 1.48 (m, 2H), 1.58 (m, 2H), 2.18 (m, 2H), 2.40 (m, 2H), 4.05 (s, 2H), 6.71 (s, 1H), 7.37 (s, 1H), 12.22 (s, 1H).

Step 15c: N1-(2-Aminophenyl)-N7-(5-((5-tert-butyloxazol-2-yl)methylthio)thiazol-2-yl)heptanediamide (Compound 17)

The title compound 17 (30 mg, 23%) as a yellow solid was synthesized from compound 0110-17 (80 mg, 0.19 mmol) using the procedure similar to that described for compound 4 (Example 4): mp 115-116° C. LCMS: 502 [M+1]$^+$. $^1$H-NMR (400 MHz, DMSO-$d_6$) δ 1.18 (s, 9H), 1.31 (m, 2H), 1.61 (m, 4H), 2.30 (m, 2H), 2.43 (m, 2H), 4.06 (s, 2H), 4.81 (s, 2H), 6.53 (m, 1H), 6.72 (m, 2H), 6.89 (m, 1H), 7.14 (m, 1H), 7.38 (s, 1H), 9.09 (s, 1H), 12.24 (s, 1H).

Example 16

Preparation of N$^1$-(2-aminophenyl)-N$^8$-(5-((5-tert-butyloxazol-2-yl)methylthio)thiazol-2-yl)octanediamide (Compound 18)

The title compound 18 (59 mg, 57%) as a yellow solid was synthesized from compound 0110-1 (85 mg, 0.20 mmol), TBTU (128 mg, 0.40 mmol), N$^1$,N$^2$-diisopropylethane-1,2-diamine (77 mg, 0.60 mmol), benzene-1,2-diamine (43 mg, 0.40 mmol) and DMF (1 mL) using the procedure similar to that described for compound 4 (Example 4): LCMS: 516 [M+1]$^+$. $^1$H-NMR (500 MHz, DMSO-$d_6$) δ 1.18 (s, 9H), 1.31 (m, 4H), 1.59 (m, 4H), 2.30 (t, J=7.5 Hz, 2H), 2.41 (t, J=7.5 Hz, 2H), 4.05 (s, 2H), 4.81 (s, 2H), 6.53 (m, 1H), 6.70 (m, 2H), 6.89 (m, 1H), 7.14 (m, 1H), 7.37 (s, 1H), 9.10 (s, 1H), 12.21 (s, 1H).

Example 17

Preparation of N$^1$-(2-acetamidophenyl)-N$^8$-(5-((5-tert-butyloxazol-2-yl)methylthio)thiazol-2-yl)octanediamide (Compound 19)

N-(2-aminophenyl)acetamide (59 mg, 57%) as a yellow solid was synthesized from 1,2-diaminobenzene (216 mg, 2.00 mmol), EDCI (764 mg, 4.00 mmol), HOBt (540 mg, 4.00 mmol), DMAP (488 mg, 4.00 mmol), acetic acid (120 mg, 2.00 mmol) and DMF (1 mL) using the procedure similar to that described for compound 1 (Example 1): LCMS: 531 [M+1]$^+$. $^1$H-NMR (400 MHz. DMSO-$d_6$) δ 2.03 (s, 3H), 4.85 (s, 2H), 6.52 (m, 1H), 6.70 (m, 1H), 6.89 (m, 1H), 7.15 (m, 1H), 9.11 (s, 1H).

The title compound 19 (60 mg, 54%) as a white solid was synthesized from compound 0110-1 (85 mg, 0.20 mmol), TBTU (128 mg, 0.40 mmol), N$^1$,N$^2$-diisopropylethane-1,2-diamine (77 mg, 0.60 mmol), N-(2-aminophenyl)acetamide (60 mg, 0.40 mmol) and DMF (1 mL) using the procedure similar to that described for compound 4 (Example 4): LCMS: 558 [M+1]$^+$. $^1$H-NMR (400 MHz. DMSO-$d_6$) δ 1.18 (s, 9H), 1.31 (m, 4H), 1.59 (m, 4H), 2.06 (s, 3H), 2.34 (t, J=7.2 Hz, 2H), 2.40 (t, J=7.2 Hz, 2H), 4.04 (s, 2H), 6.71 (s, 1H), 7.12 (m, 2H), 7.36 (s, 1H), 7.52 (m, 2H), 9.39 (s, 1H), 9.43 (s, 1H), 12.25 (s, 1H).

Example 18

N$^1$-(2-aminophenyl)-N$^8$-(5-(1-(5-tert-butyloxazol-2-yl)ethylthio)thiazol-2-yl)octanediamide (Compound 20)

Step 18a: 2-Chloro-N-(3,3-dimethyl-2-oxobutyl) acetamide (Compound 0104-20)

The title compound 0104-20 (12.1 g, 92%) as a colorless oil was synthesized from 0103 (10.40 g, 90.30 mmol) using the procedure similar to that described for compound 0104-1 (Example 1): $^1$H NMR (400 MHz, CDCl$_3$): δ 1.15 (s, 9H), 1.68 (d, J=6.8 Hz, 3H), 4.22 (d, J=4.4 Hz, 2H), 4.38 (q, J=7.2 Hz, 1H).

Step 18b: 5-tert-Butyl-2-(1-chloroethyl)oxazole (Compound 0105-20)

The title compound 0105-20 (9.01 g, 76%) as a colorless oil was synthesized from 0104-20 (12.10 g, 63.13 mmol) and POCl$_3$ (24 mL) using the procedure similar to that described for compound 0105-1 (Example 1): LCMS: 253 [M+1]$^+$. $^1$H NMR (400 MHz, DMSO-$d_6$): δ 1.25 (s, 9H), 1.81 (d, J=6.8 Hz, 3H), 5.41 (q, J=6.8 Hz, 1H), 6.85 (s, 1H).

Step 18c: 5-(1-(5-tert-Butyloxazol-2-yl)ethylthio) thiazol-2-amine (Compound 0108-20)

The title compound 0108-20 (2.56 g, 50%) as a brown solid was synthesized from 0107 (3.00 g, 19.08 mmol), 0105-20 (4.00 g, 21.39 mmol) using the procedure similar to that described for compound 0108-1 (Example 1): LCMS: 253 [M+1]$^+$. $^1$H NMR (400 MHz, DMSO-$d_6$): δ 1.23 (s, 9H), 1.52 (d, J=6.8 Hz, 3H), 4.24 (q, J=7.2 Hz, 1H), 6.69 (s, 1H), 6.80 (s, 1H), 7.28 (s, 2H).

Step 18d: Methyl 8-(5-(1-(5-tert-butyloxazol-2-yl) ethylthio)thiazol-2-ylamino)-8-oxooctanoate (Compound 0109-20)

The title compound 0109-20 (300 mg, 66%) as a brown oil was synthesized from compound 0108-20 (283 mg, 0.35 mmol), TEA (0.5 mL), THF (30 mL), and methyl 8-chloro-8-oxooctanoate (0.4 g, 0.7 mmol) using the procedure similar to that described for compound 0109-1 (example 1): LCMS: 454 [M+1]$^+$.

Step 18e: 8-(5-(1-(5-tert-Butyloxazol-2-yl)ethylthio) thiazol-2-ylamino)-8-oxooctanoic acid (Compound 0110-20)

The title compound 0110-20 (0.25 g, 86% yield) as a pale yellow solid was synthesized from compound 0109-20 (0.3 g, 0.67 mmol), LiOH (0.25 g, 6.7 mmol), THF (10.0 mL), and H₂O (5 mL) using the procedure similar to that described for compound 0110-1 (Example 1): LCMS: 440 [M+1].

Step 18f: $N^1$-(2-Aminophenyl)-$N^8$-(5-(1-(5-tert-butyloxazol-2-yl)ethylthio)thiazol-2-yl)octanediamide (Compound 20)

The title compound 20 (25 mg, 10%) as a pale white solid was synthesized from compound 0110-20 (200 mg, 0.45 mmol), TBTU (293 mg, 0.90 mmol), DIPEA (176 mg, 1.35 mmol) and DMF (3 mL) using the procedure similar to that described for compound 4 (Example 4): m.p. 76-78° C., LCMS: 530 [M+1]⁺. ¹H-NMR (400 MHz. DMSO-d₆) δ 1.18 (s, 9H), 1.31 (m, 4H), 1.58 (m, 7H), 2.30 (t, J=7.6 Hz, 2H), 2.40 (t, J=7.6 Hz, 2H), 4.38 (m, 1H), 4.81 (s, 1H), 6.51 (m, 1H), 6.70 (m, 2H), 6.87 (m, 2H), 7.15 (m, 1H), 7.31 (s, 1H), 9.11 (s, 1H), 12.21 (s, 1H).

Example 19

Preparation of $N^1$-(4-aminophenyl)-$N^8$-(5-((5-tert-butyloxazol-2-yl)methylthio)thiazol-2-yl)octanediamide (Compound 21)

The title compound 21 (90 mg, 44%) as a white solid was synthesized from compound 0110-1 (85 mg, 0.20 mmol), benzene-1,4-diamine (43 mg, 0.4 mmol), DIPEA (77 mg, 0.6 mmol), TBTU (128 mg, 0.4 mmol), and DMF (1 mL) using the procedure similar to that described for compound 4 (Example 4): m.p. 103-107° C., LCMS: 516 [M+1]⁺. ¹H-NMR (400 MHz. DMSO-d₆) δ 1.18 (s, 9H), 1.29 (m, 4H), 1.56 (m, 4H), 2.20 (t, J=7.2 Hz, 2H), 2.40 (t, J=7.2 Hz, 2H), 4.05 (s, 2H), 4.81 (br s, 2H), 6.47 (m, 2H), 6.71 (s, 1H), 7.19 (m, 2H), 7.38 (s, 1H), 9.41 (s, 1H), 12.21 (br s, 1H).

Example 20

Preparation of $N^1$-(3-aminophenyl)-$N^8$-(5-((5-tert-butyloxazol-2-yl)methylthio)thiazol-2-yl)octanediamide (Compound 22)

The title compound 22 (90 mg, 44%) as a white solid was synthesized from compound 0110-1 (170 mg, 0.40 mmol), benzene-1,3-diamine (145 mg, 0.80 mmol), DIPEA (155 mg, 1.2 mmol), TBTU (257 mg, 0.8 mmol), and DMF (2 mL) using the procedure similar to that described for compound 4 (Example 4): LCMS: 516 [M+1]⁺. ¹H-NMR (400 MHz. DMSO-d₆) δ 1.18 (s, 9H), 1.29 (m, 4H), 1.57 (m, 4H), 2.24 (t, J=7.2 Hz, 2H), 2.40 (t, J=7.2 Hz, 2H), 4.05 (s, 2H), 6.22 (m, 1H), 6.66 (m, 1H), 6.71 (s, 1H), 6.88 (t, J=8.0 Hz, 1H), 6.93 (m, 1H), 7.37 (s, 1H), 9.53 (s, 1H), 12.22 (br s, 1H).

Example 21

Preparation of $N^1$-(2-amino-4-fluorophenyl)-$N^8$-(5-((5-tert-butyloxa-zol-2-yl)methylthio)thiazol-2-yl)octanediamide (Compound 23)

The title compound 23 (96 mg, 45%) as a pale white solid was synthesized from compound 0110-1 (170 mg, 0.40 mmol), 4-fluorobenzene-1,2-diamine (101 mg, 0.80 mmol), DIPEA (155 mg, 1.2 mmol), TBTU (257 mg, 0.8 mmol), and DMF (1 mL) using the procedure similar to that described for compound 4 (Example 4): m.p. 94-98° C., LCMS: 534 [M+1]⁺. ¹H-NMR (400 MHz. DMSO-d₆) δ 1.18 (s, 9H), 1.31 (m, 4H), 1.58 (m, 4H), 2.29 (t, J=7.6 Hz, 2H), 2.41 (t, J=7.6 Hz, 2H), 4.05 (s, 2H), 5.13 (s, 2H), 6.29 (m, 1H), 6.48 (dd, J=11.2 Hz, 2.8 Hz, 1H), 6.71 (s, 1H), 7.08 (m, 1H), 7.34 (s, 1H), 9.02 (s, 1H), 12.22 (br s, 1H).

Example 22

Preparation of $N^1$-(2-amino-5-(trifluoromethyl)phenyl)-$N^8$-(5-((5-tert-butyloxazol-2-yl)methylthio)thiazol-2-yl)octanediamide (Compound 24) and $N^1$-(2-amino-4-(trifluoromethyl)phenyl)-$N^8$-(5-((5-tert-butyloxazol-2-yl)methylthio)thiazol-2-yl)octanediamide (Compound 25)

The two separable compound 24 (83 mg, 36%) and compound 25 (25 mg, 11%), both as white solids, were synthesized from compound 0110-1 (170 mg, 0.40 mmol), 4-(trifluoromethyl)benzene-1,2-diamine (141 mg, 0.80 mmol), DIPEA (155 mg, 1.2 mmol), TBTU (257 mg, 0.8 mmol) and DMF (2 mL) using the procedure similar to that described for compound 4 (Example 4).

Compound 24: m.p. 77-82° C., LCMS: 583 [M+1]⁺, ¹H-NMR (400 MHz. DMSO-d₆) δ 1.18 (s, 9H), 1.32 (m, 4H), 1.59 (m, 4H), 2.34 (t, J=7.2 Hz, 2H), 2.41 (t, J=7.2 Hz, 2H), 4.05 (s, 2H), 6.71 (s, 1H), 6.81 (m, 1H), 7.19 (m, 1H), 7.37 (s, 1H), 7.61 (m, 1H), 9.11 (s, 1H), 12.21 (br s, 1H).

Compound 25: m.p. 114-116° C., LCMS: 583 [M+1]⁺. ¹H-NMR (400 MHz. DMSO-d₆) δ 1.18 (s, 9H), 1.31 (m, 4H), 1.59 (m, 4H), 2.35 (t, J=7.2 Hz, 2H), 2.41 (t, J=7.2 Hz, 2H), 4.05 (s, 2H), 5.33 (br s, 2H), 6.71 (s, 1H), 6.83 (dd, J=8.0 Hz, 1.6 Hz, 1H), 7.02 (d, J=1.6 Hz, 1H), 7.38 (s, 1H), 7.49 (d, J=8.0 Hz, 1H), 9.19 (s, 1H), 12.22 (s, 1H).

Example 23

Preparation of $N^1$-(2-amino-4-methylphenyl)-$N^8$-(5-((5-tert-butyloxazol-2-yl)methylthio)thiazol-2-yl)octanediamide (Compound 26)

The title compound 26 (48 mg, 23%) as a white solid was synthesized from compound 0110-1 (170 mg, 0.40 mmol), 4-methylbenzene-1,2-diamine (98 mg, 0.80 mmol), DIPEA (155 mg, 1.2 mmol), TBTU (257 mg, 0.8 mmol), and DMF (1 mL) using the procedure similar to that described for compound 4 (Example 4): m.p. 94-98° C., LCMS: 530 [M+1]⁺. ¹H-NMR (400 MHz. DMSO-d₆) δ 1.18 (s, 9H), 1.31 (m, 4H), 1.58 (m, 4H), 2.15 (s, 3H), 2.28 (t, J=7.2 Hz, 2H), 2.41 (t, J=7.2 Hz, 2H), 4.05 (s, 2H), 6.35 (m, 1H), 6.52 (s, 1H), 6.71 (s, 1H), 6.99 (m, 1H), 7.38 (s, 1H), 9.02 (s, 1H), 12.22 (s, 1H).

Example 24

Synthesis of 1-(2-Aminophenyl)-3-(5-((5-tert-butyloxazol-2-yl)methyl-thio)thiazol-2-yl)urea (Compound 27)

To a solution of 0108-1 (0.18 g, 0.67 mmol) in dichloromethane (5 mL) was added triethylamine (0.17 g, 1.68 mmol) and 4-nitrophenyl carbonochloridate (0.17 g, 0.82 mmol) at 0° C. and stirred at for 2 h. To the reaction mixture was added benzene-1,2-diamine. The reaction mixture was stirred at room temperature overnight. The solvent was evaporated under reduced pressure and the residue was purified by prep. HPLC to afford the product 27 (51 mg, 19%) as a white solid: m.p. 87-90° C., LCMS: 404 [M+1]⁺. ¹H NMR (400 MHz, DMSO-d₆): δ 1.22 (s, 9H), 4.04 (s, 2H), 6.63 (s, 1H), 6.72 (s, 1H), 6.78 (s, 1H), 6.93 (s, 1H), 7.29 (s, 2H), 8.06 (s, 1H), 10.72 (s, 1H).

Example 25

Preparation of N¹-(5-((5-tert-butyloxazol-2-yl)methylthio)thiazol-2-yl)-N⁸-(pyridin-2-yl)octanediamide (Compound 28)

The title compound 28 (92 mg, 46%) was synthesized from compound 0110-1 (170 mg, 0.40 mmol) and pyridin-2-amine (46 mg, 0.48 mmol) using the procedure similar to that described for compound 4 (Example 4): m.p. 97-98° C., LCMS: 502 [M+1]⁺; ¹HNMR (400 MHz, DMSO-d₆): δ 1.17 (s, 9H), 1.29 (s, 4H), 1.57 (s, 4H), 2.39 (m, 4H), 4.05 (s, 2H), 6.71 (s, 1H), 7.07 (m, 1H), 7.37 (s, 1H), 7.75 (t, J=9.2 Hz, 1H), 8.08 (d, J=8.4 Hz, 1H), 8.28 (d, J=4.0 Hz, 1H), 10.40 (s, 1H), 12.21 (s, 1H).

Example 26

Preparation of N¹-(5-((5-tert-butyloxazol-2-yl)methylthio)thiazol-2-yl)-N⁸-(pyridin-3-yl)octanediamide (Compound 29)

The title compound 29 (50 mg, 50%) was synthesized from compound 0110-1 (85 mg, 0.20 mmol) and pyridin-3-amine (23 mg, 0.24 mmol) using the procedure similar to that described for compound 4 (Example 4): m.p. 172-174° C., LCMS: 502 [M+1]⁺; ¹HNMR (400 MHz, DMSO-d₆) δ 1.17 (s, 9H), 1.30 (br s, 4H), 1.58 (br s, 4H), 2.33 (t, J=7.2 Hz, 2H), 2.41 (t, J=6.8 Hz, 2H), 4.05 (s, 2H), 6.71 (s, 1H), 7.32 (m, 1H), 7.37 (s, 1H), 8.02 (d, J=8.0 Hz, 1H), 8.22 (s, 1H), 8.72 (s, 1H), 10.07 (s, 1H), 12.21 (s, 1H).

Example 27

Preparation of N¹-(5-((5-tert-butyloxazol-2-yl)methylthio)thiazol-2-yl)-N⁸-(pyridin-4-yl)octanediamide (Compound 30)

The title compound 30 (75 mg, 75%) was synthesized from compound 0110-1 (85 mg, 0.20 mmol) and pyridin-4-amine (23 mg, 0.24 mmol) using the procedure similar to that described for compound 4 (Example 4): m.p. 151-152° C., LCMS: 502 [M+1]⁺; ¹HNMR (400 MHz, DMSO-d₆): δ 1.17 (s, 9H), 1.29 (br s, 4H), 1.57 (m, 4H), 2.34 (t, J=7.2 Hz, 2H), 2.41 (t, J=7.2 Hz, 2H), 4.05 (s, 2H), 6.70 (s, 1H), 7.37 (s, 1H), 7.54 (d, J=6.0 Hz, 2H), 8.39 (d, J=6.4 Hz, 2H), 10.24 (s, 1H), 12.20 (s, 1H).

Example 28

Preparation of 4-(4-(2-(5-((5-tert-butyloxazol-2-yl)methylthio)thiazol-2-ylamino)-2-oxoethyl)phenoxy)-N-methoxybutanamide (Compound 31)

Step 28a: 2-(4-(4-Methoxy-4-oxobutoxy)phenyl)acetic acid (Compound 0112-31)

To a solution of sodium methoxide (2.10 g, 38.87 mmol) in methanol (30 mL) was added 4-hydroxyphenylacetic acid (3.00 g, 19.72 mmol). The resulting mixture was stirred at room temperature for 5 min followed by the addition of methyl 4-bromobutanoate (5.80 g, 29.74 mmol). The mixture was stirred at 50° C. overnight. The solvent was removed and the residue was dissolved in water and adjusted to pH 6 with 1M hydrochloric acid. The resulting solid was filtered to afford compound 0112-31 (1.50 g, 29%) as a white solid: LCMS: 253 [M+1]⁺; ¹H NMR (400 MHz, DMSO-d₆): δ 1.96 (m, 2H), 2.46 (t, J=6 Hz, 2H), 3.47 (s, 2H), 3.60 (s, 3H), 3.95 (t, J=5.2 Hz, 2H), 6.85 (d, J=6.8 Hz, 2H), 7.15 (d, J=6.8 Hz, 2H), 12.24 (s, 1H).

Step 28b: Methyl 4-(4-(2-(5-((5-tert-butyloxazol-2-yl)methylthio)thiazol-2-ylamino)-2-oxoethyl)phenoxy)butanoate (compound 0109-31)

The title compound 0109-31 (0.8 g, 50%) was synthesized from compound 0112-31 (0.8 g, 3.17 mmol), 0108-1 (0.85 g, 4.76 mmol), EDCI (0.91 g, 4.76 mmol), HOBt (0.64 g, 4.76 mmol), triethylamine (1.5 mL) and DMF (1.9 ml) using the procedure similar to that described for compound 1 (Example 1). LCMS: 504 [M+1]⁺. ¹H NMR (400 MHz, CDCl₃): δ 1.24 (s, 9H), 2.12 (m, 2H), 2.54 (t, J=7.2 Hz, 2H), 3.70 (s, 3H), 3.74 (s, 2H), 3.92 (s, 2H), 4.01 (t, J=6.0 Hz, 2H), 6.56 (s, 1H), 6.89 (d, J=8.8 Hz, 2H), 7.18 (d, J=8.8 Hz, 2H), 7.27 (s, 1H).

Step 28c: 4-(4-(2-(5-((5-Tert-Butyloxazol-2-yl)methylthio)thiazol-2-ylamino)-2-oxoethyl)phenoxy)butanoic acid (Compound 0110-31)

The title compound 0110-31 (0.78 g, 100%) was synthesized from compound 0109-34 (0.8 g, 1.5 mmol), LiOH (0.12 g, 2.86 mmol), THF (12 mL) and H₂O (4 mL) using the procedure similar to that described for compound 0110-1 (Example 1): LCMS: 490 [M+1]⁺. ¹H NMR (400 mHz, CDCl₃): δ 1.20 (s, 9H), 2.15 (t, J=6.4 Hz, 2H), 2.60 (t, J=6.4 Hz, 2H), 3.69 (s, 2H), 3.90 (s, 2H), 4.07 (t, J=6.0 Hz, 2H), 6.55 (s, 1H), 6.87 (d, J=8.4 Hz, 2H), 7.19 (s, 1H), 7.28 (d, J=8.8 Hz, 2H).

Step 28d: 4-(4-(2-(5-((5-tert-Butyloxazol-2-yl)methylthio)thiazol-2-ylamino)-2-oxo-ethyl)phenoxy)-N-methoxybutanamide (Compound 31)

The title compound 31 (44 mg, 32%) as a pale white solid was synthesized from 0110-31 (130 mg, 0.27 mmol), TBTU (170 mg, 0.53 mmol), O-methylhydroxylamine hydrochloride (132 mg, 1.58 mmol), and N¹,N²-diisopropylethane-1,2-diamine (600 mg, 4.66 mmol), and DMF (3 mL) using the procedure similar to that described for compound 4 (Example 4): LCMS: 519 [M+1]⁺. ¹H-NMR (400 MHz. DMSO-d₆) δ 1.15 (s, 9H), 1.91 (m, 2H), 2.11 (t, J=7.6 Hz, 2H), 3.56 (s, 3H), 3.64 (s, 2H), 3.93 (t, J=6.4 Hz, 2H), 4.03 (s, 2H), 6.69 (s, 1H), 6.86 (m, 2H), 7.20 (m, 2H), 7.37 (s, 1H), 11.01 (s, 1H).

Example 29

Preparation of 4-(4-(2-(5-((5-tert-butyloxazol-2-yl)methylthio)thiazol-2-ylamino)-2-oxoethyl)phenoxy)-N-hydroxy-N-methylbutanamide (Compound 32)

The title compound 31 (42 mg, 24%) as a white solid was synthesized from 0110-31 (163 mg, 0.33 mmol), TBTU (213 mg, 0.66 mmol), N-methylhydroxylamine hydrochloride (132 mg, 1.58 mmol), and N¹,N²-diisopropylethane-1,2-diamine (600 mg, 4.66 mmol), and DMF (3 mL) using the procedure similar to that described for compound 4 (Example 4): LCMS: 519 [M+1]⁺. ¹H-NMR (400 MHz. DMSO-d₆) δ 1.15 (s, 9H), 1.90 (m, 2H), 3.09 (s, 3H), 3.64 (s, 2H), 3.95 (t, J=6.4 Hz, 2H), 4.03 (s, 2H), 6.69 (s, 1H), 6.87 (m, 2H), 7.20 (m, 2H), 7.36 (m, 1H); ¹H-NMR (400 MHz. CDCl₃) δ 1.24 (s, 9H), 2.17 (m, 2H), 2.56 (m, 2H), 3.37 (s, 3H), 3.73 (s, 2H), 3.91 (s, 2H), 4.02 (t, J=5.6 Hz, 2H), 6.56 (s, 1H), 6.86 (m, 2H), 7.18 (s, 1H), 7.25 (m, 2H).

Example 30

Preparation of N-(2-aminophenyl)-4-(4-(2-(5-((5-tert-butyloxazol-2-yl)methylthio)thiazol-2-ylamino)-2-oxoethyl)phenoxy)butanamide (Compound 34)

The title compound 34 (610 mg, 66%) as a white solid was synthesized from compound 0110-31 (0.78 g, 1.60 mmol), EDCI (0.46 g, 2.4 mmol), HOBt (0.32 g, 2.4 mmol), triethylamine (1.4 mL), and benzene-1,2-diamine (0.26 g, 2.4 mmol) using the procedure similar to that described for compound 1 (Example 1): m.p. 143-144° C., LCMS: 580 [M+1]$^+$. $^1$H NMR (400 MHz, DMSO-d$_6$): δ 1.14 (s, 9H), 2.02 (m, 2H), 3.66 (s, 2H), 4.00 (t, J=6.4 Hz, 2H), 4.04 (s, 2H), 4.84 (s, 2H), 6.53 (t, J=7.2 Hz, 1H), 6.71 (d, J=8.0 Hz, 2H), 6.89 (t, J=8.8 Hz, 2H), 6.92 (s, 1H), 7.15 (d, J=7.6 Hz, 1H), 7.22 (d, J=8.4 Hz, 2H), 7.39 (s, 1H), 9.15 (s, 1H).

Example 31

Synthesis of N-(2-aminophenyl)-5-(4-(2-(5-((5-tert-butyloxazol-2-yl)methylthio)thiazol-2-ylamino)-2-oxoethyl)phenoxy)pentanamide (Compound 35)

Step 31a: 2-(4-(5-Methoxy-5-oxopentyloxy)phenyl) acetic acid (Compound 0112-35)

The title compound 0112-35 (1.68 g, 32%) as a white solid was synthesized from 4-hydroxyphenylacetic acid (3.00 g, 19.72 mmol), sodium methoxide (2.13 g, 39.44 mmol), methyl 5-bromopentanoate (6.18 g, 29.58 mmol) and methanol (30 mL) using the procedure similar to that described for compound 0112-31 (Example 28): LCMS: 267 [M+1]$^+$; $^1$H NMR (400 MHz, CDCl$_3$): δ 1.81 (m, 4H), 2.40 (t, J=7.2 Hz, 2H), 3.58 (s, 2H), 3.67 (s, 3H), 3.95 (t, J=5.6 Hz, 2H), 6.84 (d, J=8.4 Hz, 2H), 7.18 (d, J=8.4 Hz, 2H).

Step 31b: Methyl 5-(4-(2-(5-((5-tert-butyloxazol-2-yl)methylthio)thiazol-2-ylamino)-2-oxoethyl)phenoxy)pentanoate (Compound 0109-35)

The title compound 0109-35 (0.72 g, 44%) was synthesized from compound 0112-35 (0.84 g, 3.17 mmol), 0108-1 (0.85 g, 4.76 mmol), EDCI (0.91 g, 4.76 mmol), HOBt (0.64 g, 4.76 mmol), triethylamine (1.5 mL) and DMF (9 ml) using the procedure similar to that described for compound 1 (Example 1): LCMS: 518 [M+1]$^+$. $^1$H NMR (400 MHz, CDCl$_3$): δ 1.24 (s, 9H), 1.83 (m, 4H), 2.41 (t, J=6.8 Hz, 2H), 3.69 (s, 3H), 3.75 (s, 2H), 3.93 (s, 2H), 3.97 (t, J=5.2 Hz, 2H), 6.56 (s, 1H), 6.89 (d, J=8.8 Hz, 2H), 7.18 (d, J=8.8 Hz, 2H), 7.28 (s, 1H).

Step 31c: 5-(4-(2-(5-((5-tert-Butyloxazol-2-yl)methylthio)thiazol-2-ylamino)-2-oxoethyl)phenoxy)pentanoic acid (Compound 0110-35)

The title compound 0110-35 (0.35 g, 100%) was synthesized from compound 0109-35 (0.36 g, 0.71 mmol), LiOH (60 mg, 1.43 mmol), THF (6 mL), and H$_2$O (2 mL) using the procedure similar to that described for compound 0110-1 (Example 1): LCMS: 504 [M+1]$^+$. $^1$H NMR (400 MHz, CDCl$_3$): δ 1.24 (s, 9H), 1.80 (m, 4H), 2.37 (t, J=5.6 Hz, 2H), 3.75 (s, 2H), 3.92 (s, 2H), 4.08 (m, 2H), 6.58 (s, 1H), 6.92 (d, J=8.0 Hz, 2H), 7.20 (s, 1H), 7.28 (m, 2H).

Step 31d: N-(2-Aminophenyl)-5-(4-(2-(5-((5-tert-butyloxazol-2-yl)methylthio)thiazol-2-ylamino)-2-oxoethyl)phenoxy)pentanamide (Compound 35)

The title compound 35 (290 mg, 70%) as a white solid was synthesized from compound 0110-35 (0.35 g, 0.70 mmol), EDCI (0.20 g, 1.07 mmol), HOBt (0.14 g, 1.07 mmol), triethylamine (0.7 mL) and benzene-1,2-diamine (0.12 g, 1.07 mmol) using the procedure similar to that described for compound 1 (Example 1): m.p. 107-109° C., LCMS: 594 [M+1]$^+$. $^1$H NMR (400 MHz, DMSO-d$_6$): δ 1.14 (s, 9H), 1.75 (m, 4H), 2.38 (m, 2H), 3.66 (s, 2H), 3.98 (s, 2H), 4.04 (s, 2H), 4.83 (s, 2H), 6.53 (t, J=7.6 Hz, 1H), 6.71 (d, J=9.6 Hz, 2H), 6.88 (m, 3H), 7.15 (d, J=7.6 Hz, 2H), 7.21 (d, J=8.0 Hz, 2H), 7.39 (s, 1H), 7.39 (s, 1H), 9.16 (s, 1H), 12.47 (s, 1H).

Example 32

Synthesis of N-(2-aminophenyl)-6-(4-(2-(5-((5-tert-butyloxazol-2-yl)methylthio)thiazol-2-ylamino)-2-oxoethyl)phenoxy)hexanamide (compound 36)

Step 32a: 2-(4-(6-Methoxy-6-oxohexyloxy)phenyl) acetic acid (Compound 0112-36)

The title compound 0112-36 (1.66 g, 30%) as a white solid was synthesized from 4-hydroxyphenylacetic acid (3.00 g, 19.72 mmol), sodium methoxide (2.13 g, 39.44 mmol), methyl 6-bromohexanoate (6.60 g, 29.58 mmol), and methanol (30 mL) using the procedure similar to that described for compound 0112-31 (Example 28). LCMS: 281 [M+1]$^+$. $^1$H NMR (400 MHz, CDCl$_3$): δ 1.49 (m, 2H), 1.70 (m, 2H), 1.79 (m, 2H), 2.35 (t, J=7.6 Hz, 3H), 3.58 (s, 2H), 3.67 (s, 3H), 3.93 (t, J=6.4 Hz, 2H), 6.84 (d, J=8.4 Hz, 2H), 7.18 (d, J=8.8 Hz, 2H).

Step 32b: Methyl 6-(4-(2-(5-((5-tert-butyloxazol-2-yl)methylthio)thiazol-2-ylamino)-2-oxoethyl)phenoxy)hexanoate (Compound 0109-36)

The title compound 0109-36 (0.46 g, 54%) was synthesized from compound 0112-36 (0.45 g, 1.59 mmol), 0108-1 (0.43 g, 2.38 mmol), EDCI (0.46 g, 2.38 mmol), HOBt (0.32 g, 2.38 mmol), triethylamine (0.75 mL) and DMF (5 ml) using the procedure similar to that described for compound 1 (Example 1): LCMS: 532 [M+1]$^+$. $^1$H NMR (400 MHz, CDCl$_3$): δ 1.25 (s, 9H), 1.51 (m, 2H), 1.72 (m, 2H), 1.81 (m, 2H), 2.36 (t, J=7.6 Hz, 2H), 3.68 (s, 3H), 3.75 (s, 2H), 3.93 (s, 2H), 3.96 (t, J=6.0 Hz, 2H), 6.57 (s, 1H), 6.89 (d, J=8.4 Hz, 2H), 7.19 (d, J=8.4 Hz, 2H), 7.27 (s, 1H).

Step 32c: 6-(4-(2-(5-((5-tert-Butyloxazol-2-yl)methylthio)thiazol-2-ylamino)-2-oxoethyl)phenoxy)hexanoic acid (Compound 0110-36)

The title compound 0110-36 (0.23 g, 100%) was synthesized from compound 0109-36 (0.23 g, 0.43 mmol), LiOH (42 mg, 1 mmol), THF (4 mL) and H$_2$O (2 mL) using the procedure similar to that described for compound 0110-1 (Example 1): LCMS: 518 [M+1]$^+$; $^1$H NMR (400 Hz, CDCl$_3$): δ 1.24 (s, 9H), 1.50 (m, 2H), 1.67 (m, 2H), 1.82 (m, 2H), 2.35 (t, J=6.8 Hz, 2H), 3.74 (s, 2H), 3.92 (s, 2H), 4.04 (t, J=6.0 Hz, 2H), 6.58 (s, 1H), 6.88 (d, J=8.4 Hz, 2H), 7.21 (d, J=2.8 Hz, 2H), 7.24 (s, 2H).

Step 32d: N-(2-Aminophenyl)-6-(4-(2-(5-((5-tert-butyloxazol-2-yl)methylthio)thiazol-2-ylamino)-2-oxoethyl)phenoxy)hexanamide (Compound 36)

The title compound 36 (140 mg, 43%) as a white solid was synthesized from compound 0110-36 (0.28 g, 0.54 mmol), EDCI (0.16 g, 0.81 mmol), HOBt (0.11 g, 0.81 mmol), triethylamine (0.6 mL), benzene-1,2-diamine (0.09 g, 0.81 mmol) and DMF (5 ml) using the procedure similar to that described for compound 1 (Example 1): m.p. 126-128° C., LCMS: 608 [M+1]$^+$. $^1$H NMR (400 MHz, DMSO-d$_6$): δ 1.14 (s, 9H), 1.45 (m, 2H), 1.65 (m, 2H), 1.74 (m, 2H), 2.33 (t, J=7.6 Hz, 2H), 3.66 (s, 2H), 3.95 (t, J=6.4 Hz, 2H), 4.04 (s, 2H), 4.81 (s, 2H), 6.53 (t, J=7.2 Hz, 1H), 6.71 (d, J=8.8 Hz, 2H), 6.88 (m, 3H), 7.14 (d, J=7.6 Hz, 1H), 7.20 (d, J=8.8 Hz, 2H), 7.39 (s, 1H), 9.10 (s, 1H).

Example 33

Preparation of (E)-N-(5-((5-tert-butyloxazol-2-yl)methylthio)thiazol-2-yl)-4-(3-(methoxyamino)-3-oxoprop-1-enyl)benzamide (Compound 38)

Step 33a: (E)-Ethyl 3-(4-(chlorocarbonyl)phenyl)acrylate (Compound 0112-38)

To a solution of 4-carboxybenzaldehyde (1.33 g, 8.9 mmol) in THF (5 mL) was added ethyl (triphenylphosphoranylidene) acetate (2.97 g, 8.9 mmol) at ambient temperature under nitrogen. The reaction mixture was stirred for 1 h., concentrated in vacuo and partitioned between ethyl acetate and saturated aqueous NaHCO$_3$. The water layer was adjusted to pH 4 with 1 N HCl and extracted with ethyl acetate. The organic layer was washed with water and brine, dried over MgSO$_4$, and evaporated to give a residue which was treated with hot IPE to afford (E)-4-(3-ethoxy-3-oxoprop-1-enyl)benzoic acid (1.2 g, 65%): LCMS: 221 [M+1]$^+$. $^1$H NMR (400 Hz, DMSO-d$_6$) δ 1.26-1.30 (m, 3H), 4.19-4.36 (m, 2H), 6.77 (d, J=16.2 Hz, 1H), 7.64 (d, J=8.1 Hz, 1H), 7.85 (d, J=8.1 Hz, 2H), 7.96 (d, J=8.7 Hz, 2H), 13.18 (s, 1H).

To a solution of (E)-4-(3-ethoxy-3-oxoprop-1-enyl)benzoic acid (0.22 g, 1 mmol) in toluene (3 ml) was added SOCl$_2$ (0.2 ml), a mixed solution of DMF (1 drop) and toluene (2 ml) slowly at room temperature. The reaction mixture was stirred at 80° C. for 3 h. The mixture was concentrated to remove toluene to afford the crude product 0112-38 which was used to the next step reaction without further purification. LCMS (in CH$_3$OH): 235 [M+1]$^+$.

Step 33b: (E)-Ethyl 3-(4-(5-((5-tert-butyloxazol-2-yl)methylthio)thiazol-2-ylcarbamoyl)-phenyl)acrylate (Compound 0109-38)

The title compound 0109-38 (0.1 g, 25%) was synthesized from 0108-1 (0.27 g, 1 mmol), 0112-38 (0.22 g, 1 mol) using the procedure similar to that described for compound 0109-1 (Example 1). LCMS: 472 [M+1]$^+$. $^1$H NMR (400 Hz, DMSO-d$_6$) δ 1.17-1.27 (m, 12H), 4.08 (s, 2H), 4.17-4.22 (m, 2H), 6.70-6.79 (m, 2H), 7.49 (d, J=1.8 Hz, 1H), 7.69 (d, J=15.9 Hz, 1H), 7.87 (d, J=7.5 Hz, 2H), 8.07 (d, J=5.1 Hz, 2H), 12.84 (s, 1H).

Step 33c: (E)-3-(4-(5-((5-tert-Butyloxazol-2-yl)methylthio)thiazol-2-ylcarbamoyl)-phenyl)acrylic acid (Compound 0110-38)

The title compound 0110-38 (600 mg, 64%) as a pale yellow solid was synthesized from 0109-38 (1.0 g, 2.1 mmol), LiOH (0.9 g, 21 mmol), THF (20.0 mL), and H$_2$O (4 mL) using the procedure similar to that described for compound 0110-1 (Example 1). LCMS: 444 [M+1]$^+$.

Step 33d: (E)-N-(5-((5-tert-Butyloxazol-2-yl)methylthio)thiazol-2-yl)-4-(3-(methoxy-amino)-3-oxoprop-1-enyl)benzamide (Compound 38)

The title compound 38 (45 mg, 28%) as an off white solid was synthesized from 0110-38 (150 mg, 0.34 mmol), MeONH$_2$HCl (0.28 g, 3.4 mmol), TBTU (1.08 g, 3.4 mmol), DIPEA (0.43 g, 3.4 mmol) and DMF (2 mL) using the procedure similar to that described for compound 1 (example 1): LCMS: 473 [M+1]$^+$. $^1$H NMR (400 Hz, DMSO-d$_6$) δ 1.20 (s, 9H), 3.68 (s, 3H), 4.10 (s, 2H), 6.55 (d, J=11.7 Hz, 1H), 7.50 (s, 1H), 7.57 (d, J=11.7 Hz, 1H), 7.75 (d, J=5.7 Hz, 2H), 8.10 (d, J=6.3 Hz, 2H), 11.39 (s, 1H), 12.84 (s, 1H).

Example 34

Preparation of (E)-N-(5-((5-tert-butyloxazol-2-yl)methylthio)thiazol-2-yl)-4-(3-(hydroxy(methyl)amino)-3-oxoprop-1-enyl)benzamide (Compound 39) and N-(5-((5-tert-butyloxazol-2-yl)methylthio)thiazol-2-yl)-4-(2-methyl-5-oxoisoxazolidin-3-yl)benzamide (Compound 51)

Two separable compounds, compound 39 and compound 51 were synthesized from 0110-38 (300 mg, 0.68 mmol), MeNHOH.HCl (0.56 g, 6.8 mmol), TBTU (2.16 g, 6.8 mmol), DIPEA (0.86 g, 6.8 mmol), and DMF (4 mL) using the procedure similar to that described for compound 4 (Example 4).

Compound 39 (21 mg, 14% yield): an off white solid; LCMS: 473 [M+1]$^+$. $^1$H NMR (400 Hz, DMSO-d$_6$) δ 1.20 (s, 9H), 3.23 (s, 3H), 4.10 (s, 2H), 6.73 (s, 1H), 7.37 (d, J=12.3 Hz, 1H), 7.50 (s, 1H), 7.56 (d, J=11.7 Hz, 1H), 7.82 (d, J=6.0 Hz, 2H), 8.09 (d, J=6.3 Hz, 2H), 10.18 (s, 1H), 12.84 (s, 1H).

Compound 51 (24 mg, 15% yield): an off white solid; LCMS: 473 [M+1]$^+$. $^1$H NMR (400 Hz, DMSO-d$_6$) δ 1.20 (s, 9H), 2.77 (s, 3H), 4.14-3.21 (m, 2H), 4.10 (s, 2H), 4.45 (m, 1H), 6.72 (s, 1H), 7.49 (s, 1H), 7.63 (d, J=6.3 Hz, 2H), 8.09 (d, J=6.0 Hz, 2H), 12.81 (s, 1H).

Example 35

Preparation of 8-(1H-benzo[d][1,2,3]triazol-1-yl)-N-(5-((5-tert-butyloxazol-2-yl)methylthio)thiazol-2-yl)-8-oxooctanamide (Compound 40)

The title compound 40 (38 mg, 20%) as a pale white solid was synthesized from compound 0110-1 (150 mg, 0.35 mmol) and 1H-benzo[d][1,2,3]triazole (210 mg, 1.77 mmol) using the procedure similar to that described for compound 4 (Example 4): LCMS: 527 [M+1]$^+$; $^1$H-NMR (400 MHz. DMSO-d$_6$) δ 1.16 (s, 9H), 1.40 (m, 4H), 1.63 (m, 2H), 1.79 (m, 2H), 2.42 (t, J=7.3 Hz, 2H), 3.41 (t, J=7.3 Hz, 2H), 4.05 (s, 2H), 6.71 (s, 1H), 7.38 (s, 1H), 7.60 (m, 1H), 7.78 (m, 1H), 8.25 (m, 2H), 12.24 (s, 1H).

Example 36

Preparation of N$^1$-(5-((5-tert-butyloxazol-2-yl)methylthio)thiazol-2-yl)-N$^8$-(1H-pyrazol-4-yl)octanediamide (Compound 42)

Step 36a: 1H-Pyrazol-4-amine (Compound 0113-42)

Pyrazole (2.04 g, 30 mmol) was added in portions to concentrated sulfuric acid (15 mL) at below 40° C. followed by addition of concentrated nitric acid (2.08 g, 33 mmol) at −5° C. dropwise. After the reaction was completed, the mixture was poured onto ice and extracted with ethyl acetate. The separated organic layer was washed with saturated NaHCO3 solution, brine, dried and concentrated to give the compound 4-nitro-1H-pyrazole (3.09 g, 91%) as a light yellow solid. LC-MS: 114 [M+1]$^+$; $^1$H-NMR (400 MHz, DMSO-d$_6$) δ 8.59 (br s, 2H), 13.98 (br s, 1H).

A mixture of 4-nitro-1H-pyrazole (1.13 g, 10 mmol), Pd/C (10%, 57 mg) in ethanol (20 mL) was hydrogenated at 20-30 psi on a parr apparatus overnight. The reaction mixture was filtered through celite, washed with ethanol (10 mL). The filtrate was concentrated to get desired compound 0113-42 (404 mg, 49%) as a brown solid. LC-MS: 84 [M+1]$^+$; $^1$H-NMR (400 MHz, DMSO-d$_6$) δ 3.77 (br s, 2H), 6.99 (s, 2H), 11.92 (s, 1H).

Step 36b: $N^1$-(5-((5-tert-butyloxazol-2-yl)methylthio)thiazol-2-yl)-$N^8$-(1H-pyrazol-4-yl)octanediamide (Compound 42)

The title compound 42 (50 mg, 20%) as a white solid was synthesized from compound 0110-1 (85 mg, 0.20 mmol), 1H-pyrazol-4-amine (43 mg, 0.4 mmol), DIPEA (77 mg, 0.6 mmol), TBTU (128 mg, 0.4 mmol), and DMF (1 mL) using the procedure similar to that described for compound 4 (Example 4): m.p. 107-114° C., LCMS: 491 [M+1]$^+$. $^1$H-NMR (400 MHz. DMSO-d$_6$) δ 1.17 (s, 9H), 1.28 (m, 4H), 1.56 (m, 4H), 2.21 (t, J=7.2 Hz, 2H), 2.40 (t, J=7.2 Hz, 2H), 4.05 (s, 2H), 6.72 (s, 1H), 7.38 (s, 1H), 7.63 (m, 2H), 9.85 (s, 1H), 12.16 (s, 1H), 12.50 (s, 1H).

Example 37

Preparation of $N^1$-(5-((5-tert-butyloxazol-2-yl)methylthio)thiazol-2-yl)-$N^8$-(3-(thiophen-2-yl)-1H-pyrazol-5-yl)octanediamide (Compound 43)

The title compound 43 (78 mg, 57%) was synthesized from compound 0110-1 (100 mg, 0.24 mmol) and 3-(thiophen-2-yl)-1H-pyrazol-5-amine (47 mg, 0.28 mmol) using the procedure similar to that described for compound 4 (Example 4): m.p. 181-182° C., LCMS: 573 [M+1]$^+$; $^1$HNMR (400 MHz, DMSO-d$_6$): δ 1.17 (s, 9H), 1.30 (br s, 4H), 1.62 (m, 4H), 2.42 (t, J=7.6 Hz, 2H), 3.00 (t, J=7.6 Hz, 2H), 4.05 (s, 2H), 5.71 (s, 1H), 6.71 (s, 1H), 6.75 (s, 2H), 7.10 (m, 1H), 7.38 (s, 1H), 7.49 (m, 1H), 7.54 (m, 1H), 12.24 (s, 1H).

Example 38

Preparation of 8-(5-amino-4-(4-fluorophenyl)-1H-pyrazol-1-yl)-N-(5-((5-tert-butyloxazol-2-yl)methylthio)thiazol-2-yl)-8-oxooctanamide (Compound 44)

The target compound 44 (150 mg, 55%) as a pale white solid was synthesized from compound 0110-1 (150 mg, 0.35 mmol), TBTU (224 mg, 0.70 mmol), $N^1$,$N^2$-diisopropylethane-1,2-diamine (0.5 mL), 4-(4-fluorophenyl)-1H-pyrazol-5-amine (100 mg, 0.56 mmol) and DMF (3 mL) using the procedure similar to that described for compound 4 (Example 4): m.p. 170-172° C., LCMS: 585 [M+1]$^+$. $^1$H-NMR (400 MHz. DMSO-d$_6$) δ 1.17 (s, 9H), 1.32 (m, 4H), 1.63 (m, 4H), 2.42 (t, J=7.3 Hz, 2H), 2.91 (t, J=7.3 Hz, 2H), 4.05 (s, 2H), 5.60 (s, 2H), 6.71 (s, 1H), 7.24 (m, 1H), 7.38 (s, 1H), 7.61 (m, 2H), 8.335 (s, 1H), 12.24 (s, 1H).

Example 39

Preparation of N-(5-((5-tert-butyloxazol-2-yl)methylthio)thiazol-2-yl)-2-(3-oxo-1,2,3,4-tetrahydroquinoxalin-2-yl)acetamide (Compound 46)

Step 39a: (Z)-4-(5-((5-tert-Butyloxazol-2-yl)methylthio)thiazol-2-ylamino)-4-oxobut-2-enoic acid (Compound 0110-46)

The title compound 0110-46 (150 mg, 41%) as a yellow solid was synthesized from compound 0108-1 (269 mg, 1 mmol), maleic acid (264 mg, 2 mmol), TBTU (642 mg, 2 mmol), DIPEA (387 mg, 3 mmol), and DMF (5 mL) using the procedure similar to that described for compound 0109-13 (Example 11): LCMS: 368 [M+1]$^+$. $^1$H NMR (400 MHz, DMSO-d$_6$) δ 1.19 (s, 9H), 4.08 (s, 2H), 6.47 (dd, J=12 Hz, 2H), 7.42 (s, 1H), 12.65 (s, 1H).

Step 39b: N-(5-((5-tert-Butyloxazol-2-yl)methylthio)thiazol-2-yl)-2-(3-oxo-1,2,3,4-tetrahydroquinoxalin-2-yl)acetamide (Compound 46)

The title compound 46 (30 mg, 16%) as a yellow solid was synthesized from compound 0110-46 (150 mg, 0.41 mmol), benzene-1,2-diamine (130 mg, 1.2 mmol), TBTU (257 mg, 0.8 mmol), DIPEA (155 mg, 1.2 mmol), and DMF (5 mL) using the procedure similar to that described for compound 4 (Example 4): mp 260-261° C. LCMS: 458 [M+1]$^+$; $^1$H-NMR (400 MHz, DMSO-d$_6$) δ 1.19 (s, 9H), 2.71 (m, 1H), 2.96 (m, 1H), 4.06 (s, 2H), 4.22 (m, 1H), 6.06 (s, 1H), 6.62 (m, 1H), 6.72 (m, 2H), 6.76 (m, 2H), 7.37 (s, 1H), 10.34 (s, 1H), 12.29 (s, 1H).

Example 40

Preparation of N-(2-aminophenyl)-4-(3-(2-(5-((5-tert-butyloxazol-2-yl)methylthio)thiazol-2-ylamino)-2-oxoethyl)phenoxy)butanamide (Compound 56)

Step 40a: 2-(3-(4-Methoxy-4-oxobutoxy)phenyl)acetic acid (Compound 0112-56)

The title compound 0112-56 (1.50 g, 30%) as a white solid was synthesized from 3-hydroxyphenylacetic acid (3.00 g, 19.72 mmol), sodium methoxide (2.13 g, 39.44 mmol), ethyl 4-bromobutanoate (5.77 g, 29.58 mmol), and methanol (30 mL) using the procedure similar to that described for compound 0112-31 (Example 28). LCMS: 275 [M+23]$^+$. $^1$H NMR (400 MHz, CDCl$_3$): δ 2.10 (m, 2H), 2.53 (t, J=7.2 Hz, 2H), 3.61 (s, 2H), 3.69 (s, 3H), 3.99 (t, J=6.0 Hz, 2H), 6.80 (d, J=7.2 Hz, 1H), 6.86 (d, J=7.6 Hz, 2H), 7.23 (t, J=8.4 Hz, 1H).

Step 40b: Methyl 4-(3-(2-(5-((5-tert-butyloxazol-2-yl)methylthio)thiazol-2-ylamino)-2-oxoethyl)phenoxy)butanoate (Compound 0109-56)

The title compound 0109-56 (0.27 g, 50%) was synthesized from 0108-1 (0.26 g, 0.95 mmol), 0112-56 (0.2 g, 0.79 mmol) using the procedure similar to that described for compound 0109-1 (Example 1). LCMS: 504 [M+1]$^+$. $^1$H NMR (400 MHz, DMSO-d$_6$): δ 1.13 (s, 9H), 1.96 (m, 2H), 2.46 (t, J=7.2 Hz, 2H), 3.59 (s, 3H), 3.69 (s, 2H), 3.95 (t, J=6.4 Hz, 2H), 4.04 (s, 2H), 6.81 (d, J=8.4 Hz, 2H), 6.85 (d, J=7.2 Hz, 2H), 7.21 (t, J=8.0 Hz, 1H), 7.39 (s, 1H), 12.48 (s, 1H).

Step 40c: 4-(3-(2-(5-((5-Tert-butyloxazol-2-yl)methylthio)thiazol-2-ylamino)-2-oxoethyl)phenoxy)butanoic acid (Compound 0110-56)

The title compound 0110-56 (0.23 g, 88%) was synthesized from 0109-56 (0.27 g, 0.54 mmol), LiOH (26 mg, 1.07 mmol), THF (4 mL), and H$_2$O (2 mL) using the procedure similar to that described for compound 0110-1 (Example 1). LCMS: 490 [M+1]$^+$. $^1$H NMR (400 MHz, DMSO-d$_6$): δ 1.13 (s, 9H), 1.93 (m, 2H), 2.38 (t, J=7.2 Hz, 2H), 3.70 (s, 2H), 3.96 (t, J=6.8 Hz, 2H), 4.04 (s, 2H), 6.70 (s, 1H), 6.83 (d, J=8.4 Hz, 1H), 6.87 (d, J=5.6 Hz, 2H), 7.22 (t, J=8.0 Hz, 1H), 7.40 (s, 1H), 12.15 (s, 1H), 12.49 (s, 1H).

Step 40d: N-(2-aminophenyl)-4-(3-(2-(5-((5-tert-butyloxazol-2-yl)methylthio)thiazol-2-ylamino)-2-oxoethyl)phenoxy)butanamide (Compound 56)

The title compound 56 (97 mg, 41%) as a white solid was synthesized from compound 0110-56 (300 mg, 0.61 mmol), benzene-1,2-diamine (100 mg, 0.92 mmol), EDCI.HCl (176 mg, 0.92 mmol), HOBt (125 mg, 0.92 mmol), triethylamine (0.8 mL), and DMF (5 mL) using the procedure similar to that described for compound 4 (Example 4). m.p. 85-87° C., LCMS: 580 [M+1]$^+$. $^1$H NMR (400 MHz, DMSO-d$_6$): δ 1.14 (s, 9H), 2.03 (m, 2H), 3.71 (s, 2H), 4.01 (t, J=6.0 Hz, 2H), 4.05 (s, 2H), 4.84 (s, 2H), 6.53 (t, J=7.6 Hz, 1H), 6.71 (d, J=7.6 Hz, 2H), 6.90-6.84 (m, 4H), 7.15 (d, J=7.2 Hz, 1H), 7.23 (t, J=8.0 Hz, 1H), 7.40 (s, 1H), 9.16 (s, 1H), 12.50 (s, 1H).

Example 41

Preparation of N-(2-aminophenyl)-4-(4-(1-(5-((5-tert-butyloxazol-2-yl)methylthio)thiazol-2-ylamino)-1-oxopropan-2-yl)phenoxy)butanamide (Compound 57)

Step 41a: 2-(4-(4-Methoxy-4-oxobutoxy)phenyl)propanoic acid (Compound 0112-57)

The title compound 0112-57 (1.20 g, 25%) as a white solid was synthesized from 2-(4-hydroxyphenyl)-propionic acid (3.00 g, 18.05 mmol), sodium methoxide (1.46 g, 27.08 mmol), ethyl 4-bromobutanoate (5.28 g, 27.08 mmol), and methanol (30 mL) using the procedure similar to that described for compound 0112-31 (Example 28). LCMS: 289 [M+23]$^+$.

Step 41b: Methyl 4-(4-(1-(5-((5-tert-butyloxazol-2-yl)methylthio)thiazol-2-ylamino)-1-oxopropan-2-yl)phenoxy)butanoate (Compound 0109-57)

The title compound 0109-57 (0.22 g, 56%) was synthesized from 0108-1 (0.24 g, 0.90 mmol), 0112-57 (0.2 g, 0.75 mmol) using the procedure similar to that described for compound 0109-1 (Example 1). LCMS: 518 [M+1]$^+$. $^1$H NMR (400 MHz, DMSO-d$_6$): δ 1.10 (s, 9H), 1.37 (d, J=7.2 Hz, 3H), 1.94 (t, J=6.4 Hz, 2H), 2.44 (t, J=7.2 Hz, 2H), 3.58 (s, 3H), 3.87 (q, J=7.2 Hz, 1H), 3.94 (t, J=6.4 Hz, 2H), 4.03 (s, 2H), 6.69 (s, 1H), 6.86 (d, J=8.4 Hz, 2H), 7.24 (d, J=8.8 Hz, 2H), 7.37 (s, 1H), 12.38 (s, 1H).

Step 41c: 4-(4-(1-(5-((5-Tert-butyloxazol-2-yl)methylthio)thiazol-2-ylamino)-1-oxopropan-2-yl)phenoxy)butanoic acid (Compound 0110-57)

The title compound 0110-57 (0.20 g, 92%) was synthesized from 0109-57 (0.22 g, 0.42 mmol), LiOH (20 mg, 0.85 mmol), THF (4 mL), and H$_2$O (2 mL) using the procedure similar to that described for compound 0110-1 (Example 1). LCMS: 504 [M+1]$^+$. $^1$H NMR (400 MHz, DMSO-d$_6$): δ 1.10 (s, 9H), 1.37 (d, J=7.2 Hz, 3H), 1.90 (s, 2H), 2.35 (t, J=7.2 Hz, 2H), 3.87 (q, J=8.0 Hz, 1H), 3.93 (t, J=6.8 Hz, 2H), 4.03 (s, 2H), 6.69 (s, 1H), 6.87 (d, J=8.8 Hz, 1H), 7.23 (d, J=8.4 Hz, 2H), 7.37 (s, 1H), 12.39 (s, 1H).

Step 41d: N-(2-aminophenyl)-4-(4-(1-(5-((5-tert-butyloxazol-2-yl)methylthio)thiazol-2-ylamino)-1-oxopropan-2-yl)phenoxy)butanamide (Compound 57)

The title compound 57 (97 mg, 41%) as a off-white solid was synthesized from compound 0110-57 (200 mg, 0.40 mmol), benzene-1,2-diamine (65 mg, 0.60 mmol), EDCI.HCl (115 mg, 0.60 mmol), HOBt (87 mg, 0.60 mmol), triethylamine (0.5 mL), and DMF (3 mL) using the procedure similar to that described for compound 4 (Example 4). m.p. 80-82° C., LCMS: 594 [M+1]$^+$. $^1$H NMR (400 MHz, DMSO-d$_6$): δ 1.11 (s, 9H), 1.38 (d, J=6.8 Hz, 3H), 2.00 (m, 2H), 2.47 (t, J=7.6 Hz, 2H), 3.88 (q, J=8.0 Hz, 1H), 3.99 (t, J=6.0 Hz, 2H), 4.03 (s, 2H), 4.82 (s, 2H), 6.51 (t, J=8.0 Hz, 1H), 6.70 (d, J=7.2 Hz, 2H), 6.87 (d, J=7.2 Hz, 1H), 6.90 (d, J=8.4 Hz, 2H), 7.14 (d, J=8.0 Hz, 1H), 7.25 (d, J=8.8 Hz, 2H), 7.37 (s, 1H), 9.14 (s, 1H), 12.38 (s, 1H).

Example 42

Preparation of N-(2-amino-4-fluorophenyl)-4-(4-(2-(5-((5-tert-butyloxazol-2-yl)methylthio)thiazol-2-ylamino)-2-oxoethyl)phenoxy)butanamide (Compound 59)

Step 42a: N-(2-amino-4-fluorophenyl)-4-(4-(2-(5-((5-tert-butyloxazol-2-yl)methylthio)thiazol-2-ylamino)-2-oxoethyl)phenoxy)butanamide (Compound 59)

The title compound 59 (36 mg, 32%) as a white solid was synthesized from compound 0110-31 (197 mg, 0.40 mmol), 4-fluorobenzene-1,2-diamine (101 mg, 0.80 mmol), TBTU (257 mg, 0.80 mmol), DIPEA (206 mg, 1.60 mmol), and DMF (2 mL) using the procedure similar to that described for compound 4 (Example 4). LCMS: 598 [M+1]$^+$. $^1$H-NMR (400 MHz. DMSO-d$_6$) δ 1.14 (s, 9H), 2.01 (m, 2H), 2.47 (m, 2H), 3.66 (s, 2H), 3.99 (t, J=6.4 Hz, 2H), 4.04 (s, 2H), 5.17 (s, 2H), 6.29 (m, 1H), 6.47 (m, 1H), 6.70 (s, 1H), 6.90 (d, J=8.8 Hz, 2H), 7.08 (m, 1H), 7.21 (d, J=8.8 Hz, 2H), 7.40 (s, 1H), 9.08 (s, 1H), 12.47 (s, 1H).

Example 43

Preparation of N-(2-amino-5-fluorophenyl)-4-(4-(2-(5-((5-tert-butyloxazol-2-yl)methylthio)thiazol-2-ylamino)-2-oxoethyl)phenoxy)butanamide (Compound 60)

Step 43a: Tert-butyl 2-amino-4-fluorophenylcarbamate (Compound 0113-60)

A solution of 4-fluorobenzene-1,2-diamine (0.252 g, 2.0 mmol), (Boc)$_2$O (0.436 g, 2.0 mmol) in dry THF (6 mL) was stirring at room temperature for 6 h. The reaction mixture was concentrated in vacuo, extracted with ethyl acetate. The organic phase was washed with saturated NaHCO$_3$, dried over anhydrous Na$_2$SO$_4$, evaporated to afford crude product as oil. The product was further purified by flash column chromatography on silica gel (ethyl acetate in petroleum ether, 20% v/v) to afford pure product 0113-60 (0.2 g, 44%) as a yellow solid. LCMS: 171 [M-56+1]$^+$, $^1$H-NMR (400 MHz. DMSO-d$_6$) δ 1.51 (s, 9H), 5.20 (s, 2H), 6.35 (m, 1H), 6.52 (dd, J=11.2, 2.8 Hz, 1H), 7.17 (m, 1H), 8.32 (s, 1H).

Step 43b: N-(2-amino-5-fluorophenyl)-4-(4-(2-(5-((5-tert-butyloxazol-2-yl)methylthio)thiazol-2-ylamino)-2-oxoethyl)phenoxy)butanamide (Compound 60)

A solution of 0110-31 (200 mg, 0.4 mmol), TBTU (200 mg, 0.6 mmol), N$^1$,N$^2$-diisopropylethane-1,2-diamine (364 mg, 2.82 mmol), and tert-butyl 2-amino-4-fluorophenylcarbamate (0113-60) (90 mg, 0.4 mmol) in DMF (4 mL) and THF (2 mL) was stirred at r.t. for 3 hours. Then DMF and THF were removed under reduced pressure and the residue was dispensed in water and filtered to get the crude product. The crude compound was further purified by flash column chromatography on silica gel (ethyl acetate in petroleum ether, 50% v/v) to afford pure product tert-butyl 2-(4-(4-(2-(5-((5-tert-butyloxazol-2-yl)methylthio)thiazol-2-ylamino)-2-oxoethyl)phenoxy)butanamido)-4-fluorophenylcarbamate (150 mg, 54%) as a pale yellow solid. LCMS: 698 [M+1]$^+$.

The above synthesized compound (150 mg, 0.21 mmol) was dissolved in THF (2 mL) and TFA (2 mL) was added. The mixture was stirred at 40° C. for 3 hours. The solvent was removed under reduced pressure. To the residue was added water and extracted with CH$_2$Cl$_2$ (3×50 mL). The organic layers were washed with water (3×30 mL), brine (30 mL), dried over anhydrous Na$_2$SO$_4$, concentrated to get the crude product. The crude product was purified by prep. HPLC to obtain compound 60 (50 mg, 38%) as a pale yellow solid. m.p. 140-142° C. LCMS: 598 [M+1]$^+$. $^1$H-NMR (400 MHz. DMSO-d$_6$) δ 1.13 (s, 9H), 2.01 (m, 2H), 2.47 (m, 2H), 3.65 (s, 2H), 3.99 (m, 2H), 4.03 (s, 2H), 4.78 (s, 2H), 6.70 (m, 3H), 6.89 (m, 2H), 7.21 (m, 2H), 7.38 (s, 1H), 9.15 (s, 1H), 12.44 (s, 1H).

Example 44

Preparation of 4-(4-(2-(5-((5-tert-butyloxazol-2-yl)methylthio)thiazol-2-ylamino)-2-oxoethyl)phenoxy)-N-phenylbutanamide (Compound 61)

Step 44a: 4-(4-(2-(5-((5-tert-Butyloxazol-2-yl)methylthio)thiazol-2-ylamino)-2-oxoethyl)phenoxy)-N-phenylbutanamide (Compound 61)

The title compound 61 (109 mg, 64%) as a white solid was synthesized from compound 0110-31 (147 mg, 0.30 mmol), aniline (56 mg, 0.60 mmol), TBTU (193 mg, 0.60 mmol), DIPEA (155 mg, 0.60 mmol), and DMF (2 mL) using the procedure similar to that described for compound 4 (Example 4). LCMS: 565 [M+1]$^+$. $^1$H-NMR (400 MHz. DMSO-d$_6$) δ 1.13 (s, 9H), 2.01 (m, 2H), 2.47 (m, 2H), 3.65 (s, 2H), 3.98 (t, J=6.4 Hz, 2H), 4.03 (s, 2H), 6.68 (s, 1H), 6.88 (d, J=8.4 Hz, 2H), 7.01 (m, 1H), 7.20 (d, J=8.4 Hz, 2H), 7.27 (m, 2H), 7.39 (s, 1H), 7.58 (s, 2H), 9.94 (s, 1H), 12.45 (s, 1H).

Example 45

Preparation of 4-(4-(2-(5-((5-tert-butyloxazol-2-yl)methylthio)thiazol-2-ylamino)-2-oxoethyl)phenoxy)-N-(pyridin-4-yl)butanamide (Compound 62)

Step 45a: 4-(4-(2-(5-((5-tert-Butyloxazol-2-yl)methylthio)thiazol-2-ylamino)-2-oxoethyl)phenoxy)-N-(pyridin-4-yl)butanamide (Compound 62)

The title compound 62 (80 mg, 71%) as a white solid was synthesized from compound 0110-31 (98 mg, 0.20 mmol), 4-aminopyridine (23 mg, 0.24 mmol), TBTU (128 mg, 0.40 mmol), DIPEA (103 mg, 0.8 mmol), and DMF (1 mL) using the procedure similar to that described for compound 4 (Example 4). LCMS: 566 [M+1]$^+$. $^1$H-NMR (400 MHz. DMSO-d$_6$) δ 1.13 (s, 3H), 2.02 (m, 2H), 2.55 (m, 2H), 3.65 (s, 2H), 3.99 (t, J=6.4 Hz, 2H), 4.03 (s, 2H), 6.68 (s, 1H), 6.87 (d, J=8.4 Hz, 2H), 7.20 (d, J=8.4 Hz, 2H), 7.39 (s, 1H), 7.63 (m, 2H), 8.44 (m, 2H), 10.51 (s, 1H), 12.46 (s, 1H).

Example 46

Preparation of 4-(4-(2-(5-((5-tert-butyloxazol-2-yl)methylthio)thiazol-2-ylamino)-2-oxoethyl)phenoxy)-N-(pyridin-3-yl)butanamide (Compound 63)

Step 46a: 4-(4-(2-(5-((5-tert-butyloxazol-2-yl)methylthio)thiazol-2-ylamino)-2-oxoethyl)phenoxy)-N-(pyridin-3-yl)butanamide (Compound 63)

The title compound 63 (36 mg, 32%) as a white solid was synthesized from compound 0110-31 (98 mg, 0.20 mmol), 3-aminopyridine (23 mg, 0.24 mmol), TBTU (128 mg, 0.40 mmol), DIPEA (103 mg, 0.8 mmol), and DMF (1 mL) using the procedure similar to that described for compound 4 (Example 4). LCMS: 566 [M+1]$^+$. $^1$H-NMR (400 MHz. DMSO-d$_6$) δ 1.10 (s, 9H), 2.00 (m, 2H), 2.49 (m, 2H), 3.63 (s, 2H), 3.97 (t, J=6.4 Hz, 2H), 4.01 (s, 2H), 6.66 (s, 1H), 6.86 (d, J=8.4 Hz, 2H), 7.18 (d, J=8.4 Hz, 2H), 7.30 (m, 1H), 7.36 (s, 1H), 8.01 (m, 1H), 8.25 (m, 1H), 8.70 (m, 1H), 10.15 (s, 1H), 12.43 (s, 1H).

Example 47

Preparation of 4-(4-(2-(5-((5-tert-butyloxazol-2-yl)methylthio)thiazol-2-ylamino)-2-oxoethyl)phenoxy)-N-(pyridin-2-yl)butanamide (Compound 64)

Step 47a: 4-(4-(2-(5-((5-tert-butyloxazol-2-yl)methylthio)thiazol-2-ylamino)-2-oxoethyl)phenoxy)butanoyl chloride (Compound 0111-64)

To a solution of compound 0110-31 (245 mg, 0.50 mmol) in dichloremethane (2 mL) was added SOCl$_2$ (0.2 mL) at 0° C. The mixture was stirred at room temperature for 2 hours. The solvent was removed in vacuo to give crude product 0111-64 which was used in next step directly without further purification.

Step 47b: 4-(4-(2-(5-((5-tert-butyloxazol-2-yl)methylthio)thiazol-2-ylamino)-2-oxoethyl)phenoxy)-N-(pyridin-2-yl)butanamide (64)

To a solution of 2-aminopyridine (47 mg, 0.5 mmol) in dichloromethane (2 mL) was added a solution of 0111-64 in dichloromethane dropwise at room temperature and stirred at room temperature for 2 hours. The additional dichloromethane (5 ml) was added and the mixture was washed with water and brine, dried and concentrated. The residue was purified by prep. TLC. (petroleum ether in ethyl acetate, 30% v/v) to give compound 64 (79 mg, 28%) as a white solid. m.p. 126-129° C. LCMS: 565 [M+1]$^+$. $^1$H-NMR (400 MHz. DMSO-d$_6$) δ 1.12 (s, 9H), 2.00 (m, 2H), 2.55 (m, 2H), 3.64 (s, 2H), 3.97 (t, J=6.4 Hz, 2H), 4.03 (s, 2H), 6.68 (s, 1H), 6.87 (d, J=8.4 Hz, 2H), 7.06 (m, 1H), 7.19 (d, J=8.4 Hz, 2H), 7.38 (s, 1H), 7.74 (m, 1H), 8.08 (m, 1H), 8.27 (m, 1H), 10.49 (s, 1H), 12.45 (s, 1H).

Example 48

Preparation of N-(2-aminophenyl)-4-(4-(2-(5-(1-(5-tert-butyloxazol-2-yl)ethylthio)thiazol-2-ylamino)-2-oxoethyl)phenoxy)butanamide (Compound 58)

Step 48a: Methyl 4-(4-(2-(5-(1-(5-Tert-butyloxazol-2-yl)ethylthio)thiazol-2-ylamino)-2-oxoethyl)phenoxy)butanoate (Compound 0109-58)

The title compound 0109-58 (0.22 g, 56%) as an off-white solid was synthesized from 0108-20 (0.36 g, 1.26 mmol), 0112-31 (0.20 g, 0.84 mmol) using the procedure similar to that described for compound 0109-1 (Example 1). LCMS: 518 [M+1]$^+$. $^1$H NMR (400 MHz, DMSO-d$_6$): δ 1.14 (s, 9H), 1.53 (d, J=6.8 Hz, 3H), 1.95 (m, 2H), 2.46 (t, J=7.2 Hz, 2H), 3.60 (s, 3H), 3.65 (s, 2H), 3.95 (t, J=6.4 Hz, 2H), 4.39 (q, J=7.2 Hz, 2H), 6.67 (s, 1H), 6.87 (d, J=8.8 Hz, 2H), 7.20 (d, J=8.8 Hz, 2H), 7.34 (s, 1H), 12.45 (s, 1H).

Step 48b: 4-(4-(2-(5-(1-(5-Tert-butyloxazol-2-yl)ethylthio)thiazol-2-ylamino)-2-oxoethyl)phenoxy)butanoic acid (Compound 0110-48)

The title compound 0110-48 (0.20 g, 79%) as a yellow solid was synthesized from 0109-48 (0.258 g, 0.5 mmol), LiOH (0.25 g, 10 mmol), THF (10 mL), and H$_2$O (2 mL) using the procedure similar to that described for compound 0110-1 (Example 1). LCMS: 504 [M+1]. $^1$H NMR (400 MHz. DMSO-d$_6$) δ 1.13 (s, 9H), 1.53 (d, J=6.8 Hz, 3H), 1.91 (m, 2H), 2.36 (m, 2H), 3.65 (s, 2H), 3.94 (m, 2H), 4.38 (m, 1H), 6.66 (s, 1H), 6.87 (d, J=9.6 Hz, 2H), 7.20 (d, J=8.8 Hz, 2H), 7.34 (s, 1H), 12.18 (s, 1H), 12.46 (s, 1H).

Step 48c: N-(2-aminophenyl)-4-(4-(2-(5-(1-(5-tert-butyloxazol-2-yl)ethylthio)thiazol-2-ylamino)-2-oxoethyl)phenoxy)butanamide (Compound 48)

The title compound 48 (120 mg, 51%) as a off-white solid was synthesized from compound 0110-48 (200 mg, 0.4 mmol), benzene-1,2-diamine (70 mg, 0.4 mmol), TBTU (200 mg, 0.6 mmol), DIPEA (364 mg, 2.82), and DMF (4 mL) using the procedure similar to that described for compound 4 (Example 4). m.p. 126-128° C. LCMS: 594 [M+1]$^+$. $^1$H-NMR (400 MHz. DMSO-d$_6$) δ 1.13 (s, 9H), 1.52 (d, J=7.2 Hz, 3H), 2.0 (m, 2H), 2.47 (m, 2H), 3.65 (s, 2H), 3.99 (m, 2H), 4.37 (m, 1H), 4.82 (s, 2H), 6.51 (m, 1H), 6.67 (m, 2H), 6.88 (m, 3H), 7.14 (d, J=8.0 Hz, 1H), 7.20 (d, J=8.0 Hz, 2H), 7.33 (s, 1H), 9.13 (s, 1H), 12.44 (s, 1H).

Example 49

Preparation of N-(2-aminophenyl)-4-(4-(3-(5-((5-tert-butyloxazol-2-yl)methylthio)thiazol-2-yl)ureido)phenoxy)butanamide (Compound 53)

Step 49a: Ethyl 4-(4-(3-(5-((5-tert-butyloxazol-2-yl)methylthio)thiazol-2-yl)ureido)phenoxy)butanoate (Compound 0109-53)

To a solution of compound 0108 (0.5 g, 1.86 mmol) in dichloromethane (10 mL) was added Et$_3$N (0.47 g, 4.65 mmol) and 4-nitrophenyl chloroformate (0.45 g, 2.23 mmol) at 0° C. The mixture was stirred at 0° C. for 2 h followed by the addition of ethyl 4-(4-aminophenoxy)butanoate (0.50 g, 2.23 mmol). The reaction mixture was stirred at room temperature overnight. The solvent was removed under reduced pressure and the residue was purified by flash column chromatography on silica gel (methanol in dichloromethane (2% v/v) to afford compound 0109-53 (0.41 g, 43%) as a brown solid. LCMS: 519 [M+1]$^+$. $^1$H NMR (400 MHz, DMSO-d$_6$): δ 1.17 (t, J=7.6 Hz, 3H), 1.19 (s, 9H), 1.94 (m, 2H), 2.44 (t, J=7.2 Hz, 2H), 3.94 (t, J=6 Hz, 2H), 4.03 (s, 2H), 4.07 (d, J=7.2 Hz, 2H), 6.71 (s, 2H), 6.87 (d, J=9.6 Hz, 2H), 7.27 (s, 2H), 7.33 (d, J=8.8 Hz, 2H), 8.75 (s, 1H), 10.61 (s, 1H).

Step 49b: 4-(4-(3-(5-((5-Tert-butyloxazol-2-yl)methylthio)thiazol-2-yl)ureido)phenoxy)butanoic acid (Compound 0110-53)

The title compound 0110-53 (0.37 g, 95%) as a brown solid was synthesized from 0109-53 (0.41 g, 0.79 mmol), LiOH (38 mg, 1.58 mmol), THF (4 mL), and H$_2$O (2 mL) using the procedure similar to that described for compound 0110-1 (Example 1). LCMS: 491 [M+1]$^+$. $^1$H NMR (400 MHz, DMSO-d$_6$): δ 1.20 (s, 9H), 1.91 (m, 2H), 2.38 (t, J=7.2 Hz, 2H), 3.94 (t, J=6.4 Hz, 2H), 4.04 (s, 2H), 6.72 (s, 1H), 6.89 (d, J=9.2 Hz, 2H), 7.27 (s, 2H), 7.33 (d, J=9.2 Hz, 2H), 8.75 (s, 1H).

Step 49c: N-(2-aminophenyl)-4-(4-(3-(5-((5-tert-butyloxazol-2-yl)methylthio)thiazol-2-yl)ureido)phenoxy)butanamide (Compound 53)

The title compound 53 (85 mg, 19%) as a yellow solid was synthesized from compound 0110-53 (0.37 g, 0.75 mmol), benzene-1,2-diamine (122 mg, 1.13 mmol), TBTU (363 mg, 1.13 mmol), DIPEA (0.5 ml), and DMF (4 mL) using the procedure similar to that described for compound 4 (Example 4). m.p. 147-149° C. LCMS: 581 [M+1]$^+$. $^1$H NMR (400 MHz, DMSO-d$_6$): δ 1.19 (s, 9H), 2.01 (m, 2H), 2.47 (m, 2H), 3.98 (t, J=6.4 Hz, 2H), 4.03 (s, 2H), 4.84 (s, 2H), 6.52 (d, J=8.8 Hz, 1H), 6.70 (d, J=10.0 Hz, 2H), 6.87 (d, J=8.8 Hz, 1H), 6.91 (d, J=8.8 Hz, 2H), 7.15 (d, J=8.8 Hz, 1H), 7.27 (s, 2H), 7.34 (d, J=8.8 Hz, 2H), 8.73 (s, 1H), 9.15 (s, 1H), 10.59 (s, 1H).

Example 50

Preparation of: 4-(4-(2-Aminophenylamino)-4-oxobutoxy)phenyl 5-((5-tert-butyloxazol-2-yl)methylthio)thiazol-2-ylcarbamate (Compound 54)

Step 50a: Ethyl 4-(4-hydroxyphenoxy)butanoate (0112-54)

To a solution of 4-hydroxyphenol (3.3 g, 30 mmol) in ethanol (60 mL) was added K$_2$CO$_3$ (6.21 g, 45 mmol), Bu$_4$NI (1.11 g, 3 mmol), and ethyl 4-bromobutanoate (4.68 g, 24 mmol). The resulting mixture was stirred at 60° C. overnight and filtered. To the filtrate was added water, and extracted with ethyl acetate, washed with brine, dried over Na$_2$SO$_4$ and concentrated. The residue was purified by column chromatograph on silica gel (ethyl acetate in petroleum ether, 10% v/v) to afford title product 0112-54 (1.6 g, 30%) as a brown solid. LCMS: 247 [M+23]$^+$. $^1$H NMR (400 MHz, DMSO-d$_6$): δ 1.26 (t, J=7.2 Hz, 3H), 2.08 (m, 2H), 2.51 (t, J=7.2 Hz, 2H), 3.93 (t, J=6.0 Hz, 2H), 4.15 (q, J=7.2 Hz, 2H), 6.75 (s, 4H).

Step 50b: Ethyl 4-(4-(5-((5-tert-butyloxazol-2-yl)methylthio)thiazol-2-ylcarbamoyloxy)phenoxy)butanoate (Compound 0109-54)

To a solution of compound 0108-1 (0.5 g, 1.86 mmol) in dichloromethane (10 mL) was added Et$_3$N (0.47 g, 4.65 mmol) and 4-nitrophenyl carbonochloridate (0.45 g, 2.23 mmol) at 0° C. The mixture was stirred for 2 h at the same temperature followed by the addition of ethyl 4-(4-hydroxyphenoxy)butanoate (0.50 g, 2.23 mmol). The reaction mixture was stirred at room temperature overnight. The solvent was removed under reduced pressure and the residue was purified by column chromatograph on silica gel (methanol in dichloromethane, 1% v/v) to afford the product 0109-54 (0.45 g, 47%) as a brown solid. LCMS: 519 [M+1]$^+$. $^1$H NMR (400 MHz, DMSO-d$_6$): δ 1.15-1.18 (m, 12H), 1.96 (m, 2H), 2.45 (t, J=7.2 Hz, 2H), 3.98 (t, J=6.4 Hz, 2H), 4.03-4.09 (m, 4H), 6.70 (s, 1H), 6.95 (d, J=9.2 Hz, 2H), 7.13 (d, J=8.8 Hz, 2H), 7.35 (s, 2H), 12.41 (s, 1H).

Step 50c: 4-(4-(5-((5-Tert-butyloxazol-2-yl)methylthio)thiazol-2-ylcarbamoyloxy)phenoxy)butanoic acid (Compound 0110-54)

The title compound 0110-54 (0.40 g, 94%) as an off-white solid was synthesized from 0109-54 (0.45 g, 0.87 mmol), LiOH (83 mg, 3.46 mmol), THF (4 mL), and H$_2$O (2 mL) using the procedure similar to that described for compound 0110-1 (Example 1). LCMS: 492 [M+1]$^+$. $^1$H NMR (400 MHz, DMSO-d$_6$): δ 1.19 (s, 9H), 1.94 (m, 2H), 2.39 (t, J=7.2 Hz, 2H), 3.99 (t, J=6.4 Hz, 2H), 4.07 (s, 2H), 6.72 (s, 1H), 6.97 (d, J=9.2 Hz, 2H), 7.14 (d, J=9.2 Hz, 2H), 7.36 (s, 1H), 12.27 (br s, 2H).

Step 50d: 4-(4-(2-Aminophenylamino)-4-oxobutoxy)phenyl 545-tert-butyloxazol-2-yl)methylthio)thiazol-2-ylcarbamate (Compound 54)

The title compound 54 (124 mg, 26%) as a white solid was synthesized from compound 0110-54 (0.40 g, 0.81 mmol), benzene-1,2-diamine (132 mg, 1.22 mmol), TBTU (392 mg, 1.22 mmol), DIPEA (0.5 ml), and DMF (4 mL) using the procedure similar to that described for compound 4 (Example 4). m.p. 133-136° C. LCMS: 582 [M+1]$^+$. $^1$H NMR (400 MHz, DMSO-d$_6$): δ 1.19 (s, 9H), 2.04 (m, 2H), 2.53 (m, 2H), 4.04 (t, J=6.4 Hz, 2H), 4.07 (s, 2H), 4.85 (s, 2H), 6.53 (d, J=8.0 Hz, 1H), 6.71 (d, J=6.4 Hz, 2H), 6.98-7.00 (m, 3H), 7.15 (d, J=9.2 Hz, 1H), 7.36 (s, 1H), 9.17 (s, 1H), 12.43 (s, 1H).

Biological Assays

CDK2/cyclinA (Accession number for CDK2; EMBL M68520, for cyclin A; EMBL X51688): C-terminal 6His-tagged human full length cdk2 (MW=35 kDa), and N-terminal GST-tagged human full length cyclin A (MW=75 kDa) were expressed individually with baculovirus system in Sf21 insect cells. Recombinant cdk2 protein was purified with Ni2+/NTA agarose and then activated using CAK and repurified by Q Sepharose and Ni2+/NTA agarose. Recombinant cyclin A was purified using glutathione-agarose. They were then mixed in vitro to form protein complex. Recombinant protein complex was measured to be 67% in purity with SDS-PAGE and Coomassie blue staining. Specific activity of purified enzyme was measured to be 158 U/mg, where one unit of cdk2/cyclinA activity is defined as 1 nmol phosphate incorporated into 0.1 mg/ml histone H1 per minute at 30° C. with a final ATP concentration of 100 mM. Enzyme was stored at a concentration of 0.1 mg/ml in 50 mM Tris/HCl pH7.5, 150 mM NaCl, 0.1 mM EGTA, 0.03% Brij-35, 270 mM sucrose, 1 mM benzamidine, 0.2 mM PMSF, 0.1% 2-mercaptoethanol. Frozen solution.

Histon H1 (Substrate for CDK2): Histone H1 (Sigma cat#H4524), was purified as a lysine rich fraction from calf thymus with 93% purity (MW=21.5 kDa). Purified protein was stored at a concentration of 20 mg/ml=930 μM in distilled water.

Assay Conditions:

CDK2/cyclinE (0.5 nmol) and 5 μM Histon H1 were mixed in the reaction buffer (20 mM HEPES (pH 7.5), 10 mM MgCl$_2$, 1 mM EGTA, 0.02% Brij 35, 0.02 mg/ml BSA, 0.1 mM Na$_3$VO$_4$, 2 mM DTT) with final concentration of 1 μM ATP and 1% DMSO. The reaction was incubated for 2 hours at room temperature and conversion rate of ATP is about 4.5%. An equal volume of 25% TCA was added to stop the reaction and precipitate the labeled peptides. Precipitated proteins were trapped onto glass fiber B filterplates and excess unlabeled p33 ATP was washed off. The plates were allowed to air-dry prior to the addition of 30 uL/well of Packard Microscint 20. The amount of incorporated isotope was measured using a Perkin Elmer TopCount plate reader. Different concentrations of compounds were added to reaction to assess the activity of compounds to inhibit PDGF-beta kinase. IC50 was calculated using Prism software with sigmoidal dose-response curve fitting.

The following TABLE B lists compounds representative of the invention and their activity in the CDK2 assay. In this assay, the following grading was used: I≥10 μM, 10 μM>II>1 μM, 1 μM>III>0.1 μM, and IV≤0.1 μM for IC$_{50}$.

TABLE B

| Compound | CDK1 IC50 | CDK2 IC$_{50}$ | CDK3 IC$_{50}$ | CDK4 IC$_{50}$ | CDK9 IC$_{50}$ |
|---|---|---|---|---|---|
| 1 | | IV | | | |
| 2 | | IV | | | |
| 3 | | IV | | | |
| 4 | | IV | | | |
| 5 | IV | IV | IV | III | IV |
| 6 | | IV | | | |
| 7 | | IV | | | |
| 8 | | IV | | | |
| 9 | | IV | | | |
| 10 | | IV | | | |
| 11 | | III | | | |
| 13 | | IV | | | |
| 15 | | IV | | | |
| 16 | | IV | | | |
| 17 | | IV | | | |
| 18 | IV | IV | IV | III | IV |
| 19 | | IV | | | |
| 20 | | IV | | | |
| 21 | | IV | | | |
| 22 | | IV | | | |
| 23 | | IV | | | |
| 24 | | IV | | | |
| 25 | | IV | | | |
| 26 | | IV | | | |
| 27 | | IV | | | |
| 28 | | IV | | | |
| 29 | | IV | | | |
| 30 | | IV | | | |
| 31 | | IV | | | |
| 32 | | IV | | | |
| 33 | | IV | | | |
| 34 | | IV | | | |
| 35 | | IV | | | |
| 36 | | IV | | | |
| 38 | | IV | | | |
| 39 | | II | | | |
| 40 | | IV | | | |
| 41 | | IV | | | |
| 42 | | IV | | | |
| 43 | | IV | | | |
| 44 | | IV | | | |
| 45 | | IV | | | |
| 46 | | IV | | | |
| 47 | | IV | | | |
| 48 | | IV | | | |
| 50 | | IV | | | |
| 51 | | IV | | | |
| 52 | | IV | | | |
| 54 | | IV | | | |

TABLE B-continued

| Compound | CDK1 IC50 | CDK2 IC$_{50}$ | CDK3 IC$_{50}$ | CDK4 IC$_{50}$ | CDK9 IC$_{50}$ |
|---|---|---|---|---|---|
| 56 | | IV | | | |
| 57 | | IV | | | |
| 58 | | IV | | | |
| 59 | | IV | | | |
| 60 | | IV | | | |
| 61 | | IV | | | |
| 62 | | IV | | | |
| 63 | | IV | | | |
| 64 | | IV | | | |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound of Formula I:

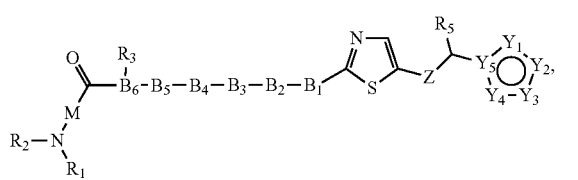

(I)

or a pharmaceutically acceptable salt, prodrug or solvate thereof, wherein $Y_1$-$Y_4$ are independently O, S, N, $NR_8$ or $CR_{21}$;

$R_{21}$ is independently selected from hydrogen, hydroxy, substituted hydroxy, amino, substituted amino, halogen, substituted or unsubstituted alkoxy, substituted or unsubstituted alkylamino, substituted or unsubstituted dialkylamino, substituted or unsubstituted thiol, $CF_3$, CN, $NO_2$, $N_3$, substituted carbonyl, sulfonyl, acyl, aliphatic, or substituted aliphatic;

$Y_5$ is C or N;

M is absent or O;

$B_1$ is $N(R_8)$;

$B_2$ is CO;

$B_3$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl; $B_4$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl;

$B_5$ is absent, O, S, SO, $SO_2$, $N(R_8)$, CO, $C_1$-$C_6$ alkyl, $C_2$-$C_6$ alkenyl, $C_2$-$C_6$ alkynyl, cycloalkyl, heterocyclic, aryl, or heteroaryl;

$B_6$ is absent, $C_1$-$C_6$ alkyl, $C_2$-$C_6$ alkenyl, $C_2$-$C_6$ alkynyl, cycloalkyl, heterocyclic, aryl, or heteroaryl; Z is O, S, S(O), $SO_2$, $SO_2NH$, $NR_8$, $C_1$-$C_6$ alkyl, $C_2$-$C_6$ alkenyl, $C_2$-$C_6$ alkynyl, C(O) or C(O)NH;

$R_8$ is hydrogen, acyl, aliphatic or substituted aliphatic;

$R_1$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heteroaryl, substituted or unsubstituted aryl, substituted or unsubstituted aryl-$C_1$-$C_6$-alkyl, or substituted or unsubstituted heteroaryl-$C_1$-$C_6$-alkyl, provided that $R_1$ is not substituted or unsubstituted 2-aminophenyl;

$R_2$ is hydrogen;

or $R_1$ and $R_2$, together with the nitrogen atom to which they are attached, form a substituted or unsubstituted heteroaryl group which is optionally fused with a cycloalkyl, aryl or heterocyclic group;

$R_3$ is absent, or $R_3$ and $R_2$, or $R_3$ and $R_1$, together with the intervening atoms, form a heterocyclic group which is optionally fused with a cycloalkyl, aryl or heterocyclic group; and $R_5$ is hydrogen, aliphatic or substituted aliphatic.

2. A compound represented by formula (II),

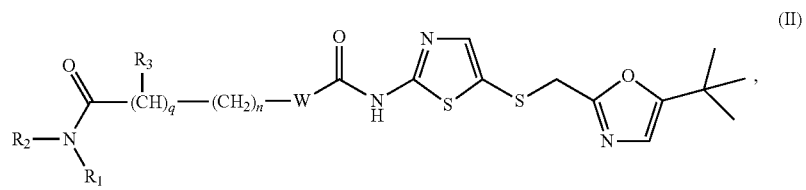

(II)

or a pharmaceutically acceptable salt, prodrug or solvate thereof;

wherein n is an integer from 0 to 8, q is 0 or 1, W is a direct bond, O or $N(R_8)$, $R_1$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heteroaryl, substituted or unsubstituted aryl, substituted or unsubstituted aryl-$C_1$-$C_6$-alkyl, or substituted or unsubstituted heteroaryl-$C_1$-$C_6$-alkyl, provided that $R_1$ is not substituted or unsubstituted 2-aminophenyl;

$R_2$ is hydrogen;

or $R_1$ and $R_2$, together with the nitrogen atom to which they are attached, form a substituted or unsubstituted heteroaryl group which is optionally fused with a cycloalkyl, aryl or heterocyclic group;

$R_3$ is absent, or $R_3$ and $R_2$, or $R_3$ and $R_1$, together with the intervening atoms, form a heterocyclic group which is optionally fused with a cycloalkyl, aryl or heterocyclic group; and $R_8$ is hydrogen, acyl, aliphatic or substituted aliphatic.

3. A compound represented by formula (III),

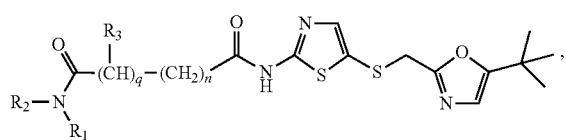
(III)

or a pharmaceutically acceptable salt, prodrug or solvate thereof;

wherein n is an integer from 0 to 6, q is 0 or 1, $R_1$ is substituted or unsubstituted $C_1$-$C_6$ alkyl, substituted or unsubstituted $C_2$-$C_6$ alkenyl, substituted or unsubstituted $C_2$-$C_6$ alkenyl, substituted or unsubstituted cycloalkyl, substituted or unsubstituted heteroaryl, substituted or unsubstituted aryl, substituted or unsubstituted aryl-$C_1$-$C_6$-alkyl, or substituted or unsubstituted heteroaryl-$C_1$-$C_6$-alkyl, provided that $R_1$ is not substituted or unsubstituted 2-aminophenyl;

$R_2$ is hydrogen;

or $R_1$ and $R_2$, together with the nitrogen atom to which they are attached, form a substituted or unsubstituted heteroaryl group which is optionally fused with a cycloalkyl, aryl or heterocyclic group; and $R_3$ is absent, or $R_3$ and $R_2$, or $R_3$ and $R_1$, together with the intervening atoms, form a heterocyclic group which is optionally fused with a cycloalkyl, aryl or heterocyclic group.

4. A compound represented by formula (IV):

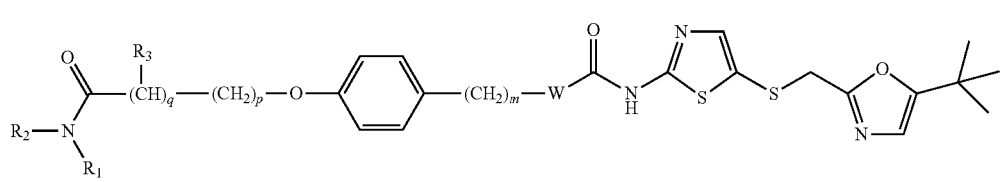
(IV)

or a pharmaceutically acceptable salt, prodrug or solvate thereof;

wherein m and p are each independently an integer from 0 to 6, q is 0 or 1, W is a direct bond, O or $N(R_8)$, $R_1$ is substituted or unsubstituted $C_1$-$C_6$ alkyl, substituted or unsubstituted $C_2$-$C_6$ alkenyl, substituted or unsubstituted $C_2$-$C_6$ alkenyl, substituted or unsubstituted cycloalkyl, substituted or unsubstituted heteroaryl, substituted or unsubstituted aryl, substituted or unsubstituted aryl-$C_1$-$C_6$-alkyl, or substituted or unsubstituted heteroaryl-$C_1$-$C_6$-alkyl, provided that $R_1$ is not substituted or unsubstituted 2-aminophenyl;

$R_2$ is hydrogen;

or $R_1$ and $R_2$, together with the nitrogen atom to which they are attached, form a substituted or unsubstituted heteroaryl group which is optionally fused with a cycloalkyl, aryl or heterocyclic group;

$R_3$ is absent, or $R_3$ and $R_2$, or $R_3$ and $R_1$, together with the intervening atoms, form a heterocyclic group which is optionally fused with a cycloalkyl, aryl or heterocyclic group; and $R_8$ is hydrogen, acyl, aliphatic or substituted aliphatic.

5. A compound represented by formula (V):

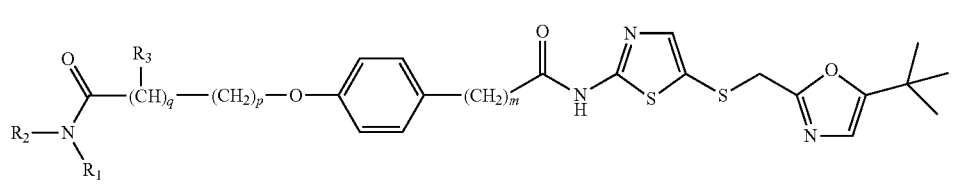
(V)

or pharmaceutically acceptable salt, prodrug or solvate thereof;

wherein m and p are each independently an integer from 0 to 6, q is 0 or 1, $R_1$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heteroaryl, substituted or unsubstituted aryl, substituted or unsubstituted aryl-$C_1$-$C_6$-alkyl, or substituted or unsubstituted heteroaryl-$C_1$-$C_6$-alkyl, provided that $R_1$ is not substituted or unsubstituted 2-aminophenyl;

$R_2$ is hydrogen;

or $R_1$ and $R_2$, together with the nitrogen atom to which they are attached, form a substituted or unsubstituted heteroaryl group which is optionally fused with a cycloalkyl, aryl or heterocyclic group; and $R_3$ is absent, or $R_3$ and $R_2$, or $R_3$ and $R_1$, together with the intervening atoms, form a heterocyclic group which is optionally fused with a cycloalkyl, aryl or heterocyclic group.

6. A compound represented by formula (VI):

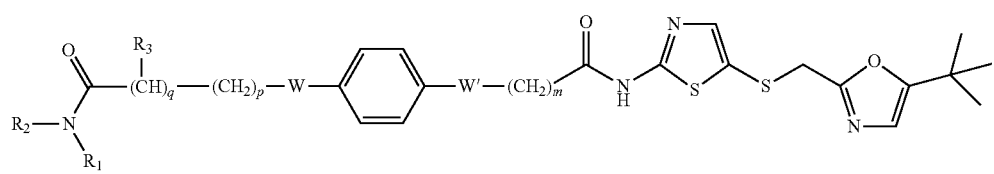

(VI)

or a pharmaceutically acceptable salt, prodrug or solvate thereof;

wherein m and p are each independently an integer from 0 to 6, q is 0 or 1, W and W' are each independently a direct bond, O or N($R_8$), $R_1$ is substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted cycloalkyl, substituted or unsubstituted heteroaryl, substituted or unsubstituted aryl, substituted or unsubstituted aryl-$C_1$-$C_6$-alkyl, or substituted or unsubstituted heteroaryl-$C_1$-$C_6$-alkyl, provided that $R_1$ is not substituted or unsubstituted 2-aminophenyl;

$R_2$ is hydrogen;

or $R_1$ and $R_2$, together with the nitrogen atom to which they are attached, form a substituted or unsubstituted heteroaryl group which is optionally fused with a cycloalkyl, aryl or heterocyclic group;

$R_3$ is absent, or $R_3$ and $R_2$, or $R_3$ and $R_1$, together with the intervening atoms, form a heterocyclic group which is optionally fused with a cycloalkyl, aryl or heterocyclic group; and $R_8$ is hydrogen, acyl, aliphatic or substituted aliphatic.

7. The compound of claim 1, wherein $R_1$ is substituted or unsubstituted aryl or substituted or unsubstituted heteroaryl.

8. The compound of claim 5, wherein $R_1$ is substituted or unsubstituted phenyl, substituted or unsubstituted pyridyl, substituted or unsubstituted pyrazolyl, substituted or unsubstituted imidazolyl, substituted or unsubstituted benzimimdazolyl, substituted or unsubstituted pyrrolyl, substituted or unsubstituted benzopyrrolyl or substituted or unsubstituted benzopyrazolyl.

9. The compound of claim 6, wherein $R_1$ is:

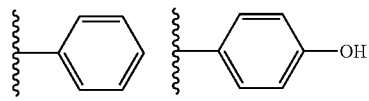

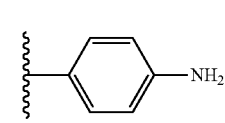

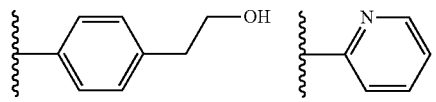

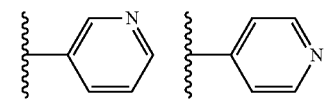

-continued

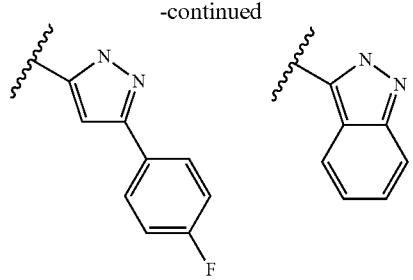

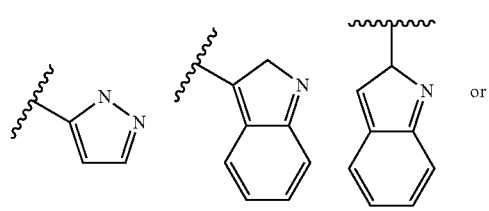

or

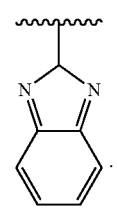

10. The compound of claim 1, wherein $R_1$ and $R_2$, together with the nitrogen atom to which they are attached, form a heteroaryl group.

11. The compound of claim 10, wherein the heteroaryl group is substituted or unsubstituted pyrazolyl, substituted or unsubstituted benzopyrazolyl, substituted or unsubstituted benzotriazolyl.

12. The compound of claim 10, wherein the heteroaryl group is:

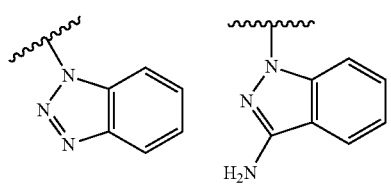

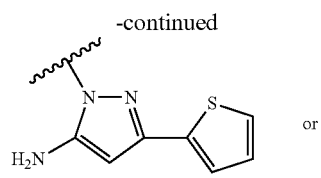

or

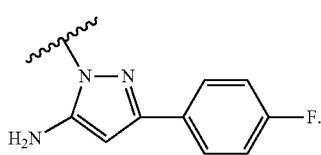

13. A compound selected from the compounds set forth in Table A or the geometric isomers, enantiomers, diastereomers, racemates, pharmaceutically acceptable salts, prodrugs and solvates thereof:

TABLE A

| Compound | Structure |
|---|---|
| 8 | 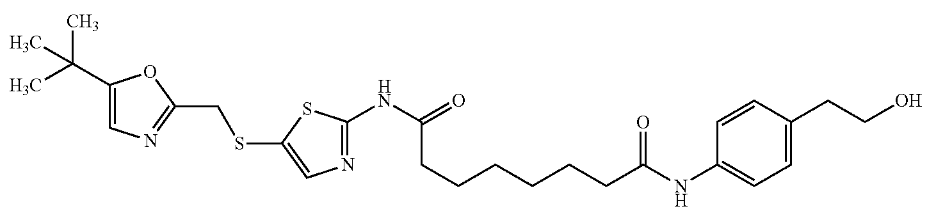 [SMILES: CC(C)(C)c1cnc(CSc2cnc(NC(=O)CCCCCCC(=O)Nc3ccc(CCO)cc3)s2)o1] |
| 9 | 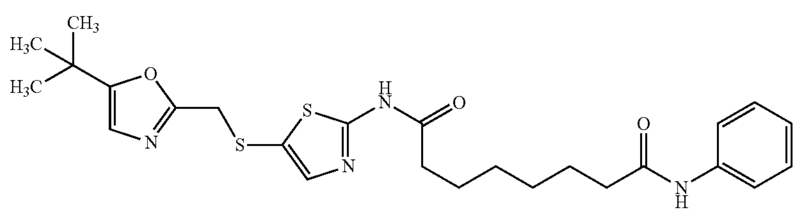 [SMILES: CC(C)(C)c1cnc(CSc2cnc(NC(=O)CCCCCCC(=O)Nc3ccccc3)s2)o1] |
| 10 | 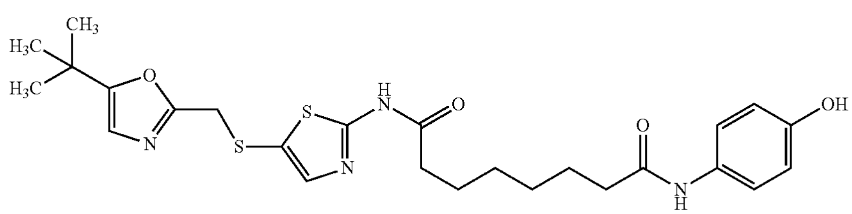 [SMILES: CC(C)(C)c1cnc(CSc2cnc(NC(=O)CCCCCCC(=O)Nc3ccc(O)cc3)s2)o1] |
| 11 | 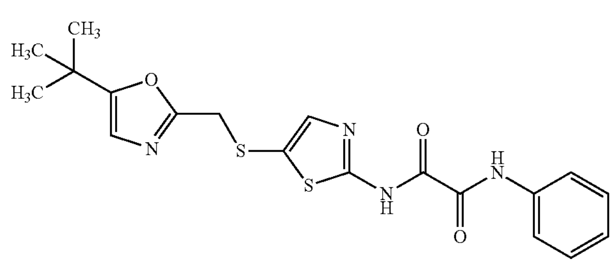 [SMILES: CC(C)(C)c1cnc(CSc2cnc(NC(=O)C(=O)Nc3ccccc3)s2)o1] |

TABLE A-continued

| Compound | Structure |
|---|---|
| 19 | 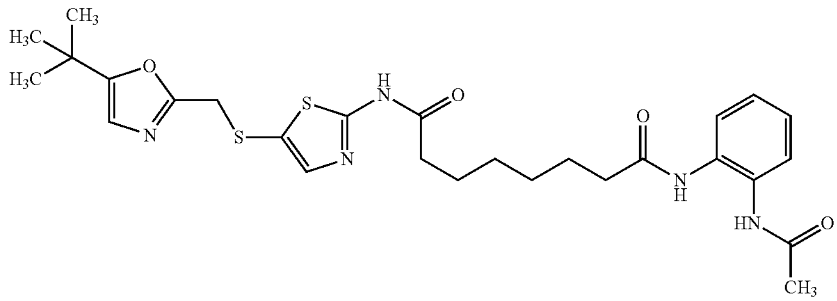 [SMILES: CC(=O)Nc1ccccc1NC(=O)CCCCCCC(=O)Nc1ncc(SCc2ncc(C(C)(C)C)o2)s1] |
| 28 | 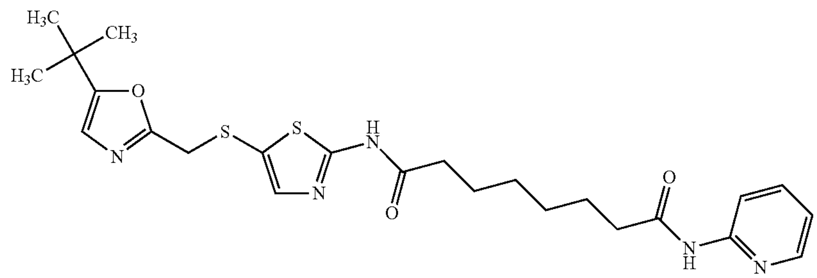 [SMILES: CC(C)(C)c1cnc(CSc2cnc(NC(=O)CCCCCCC(=O)Nc3ccccn3)s2)o1] |
| 29 | 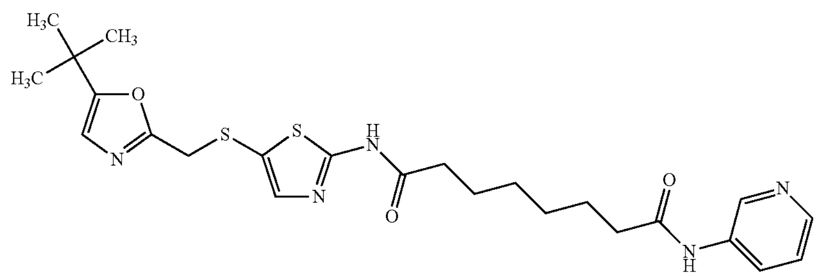 [SMILES: CC(C)(C)c1cnc(CSc2cnc(NC(=O)CCCCCCC(=O)Nc3cccnc3)s2)o1] |
| 30 | 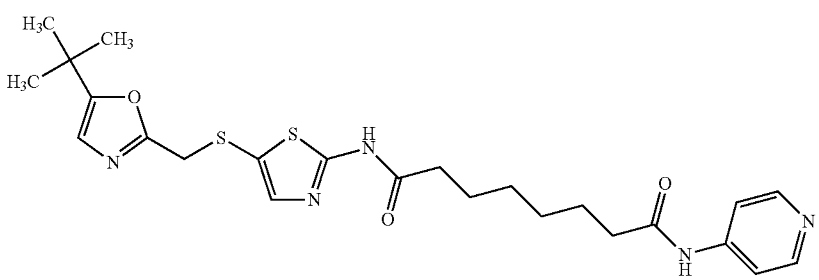 [SMILES: CC(C)(C)c1cnc(CSc2cnc(NC(=O)CCCCCCC(=O)Nc3ccncc3)s2)o1] |
| 40 | 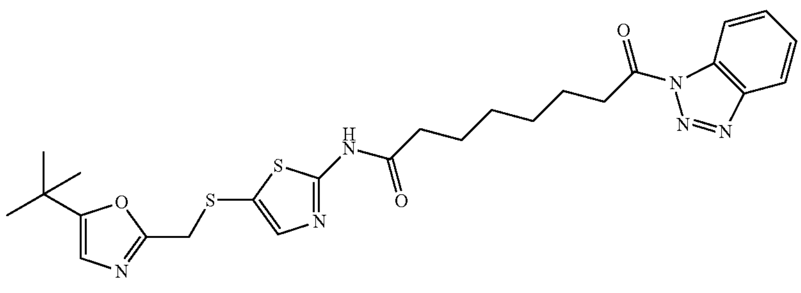 [SMILES: CC(C)(C)c1cnc(CSc2cnc(NC(=O)CCCCCCC(=O)n3nnc4ccccc43)s2)o1] |

TABLE A-continued

| Compound | Structure |
|---|---|
| 41 | 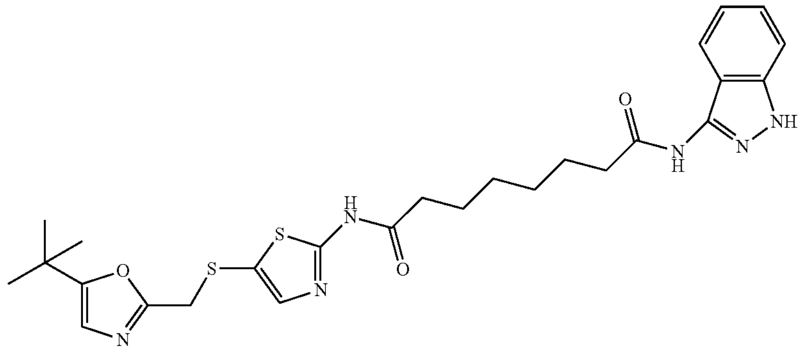 [SMILES: CC(C)(C)c1cnc(CSc2cnc(NC(=O)CCCCCCC(=O)Nc3n[nH]c4ccccc34)s2)o1] |
| 42 | 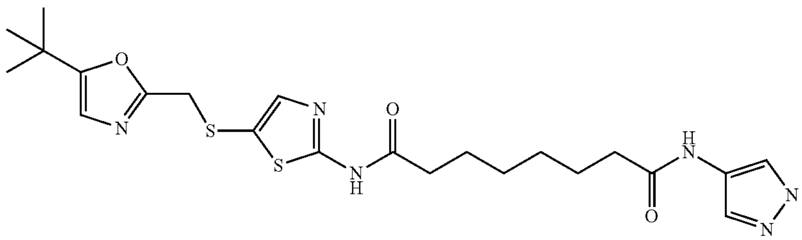 [SMILES: CC(C)(C)c1cnc(CSc2cnc(NC(=O)CCCCCCC(=O)Nc3cn[nH]c3)s2)o1] |
| 43 | 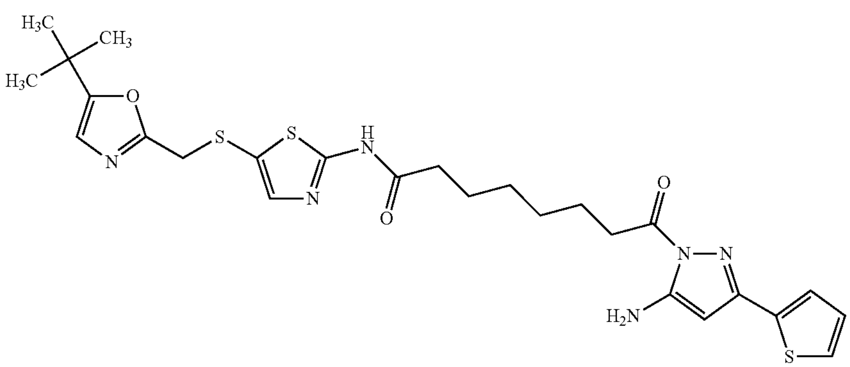 [SMILES: CC(C)(C)c1cnc(CSc2cnc(NC(=O)CCCCCCC(=O)n3nc(-c4cccs4)cc3N)s2)o1] |
| 44 | 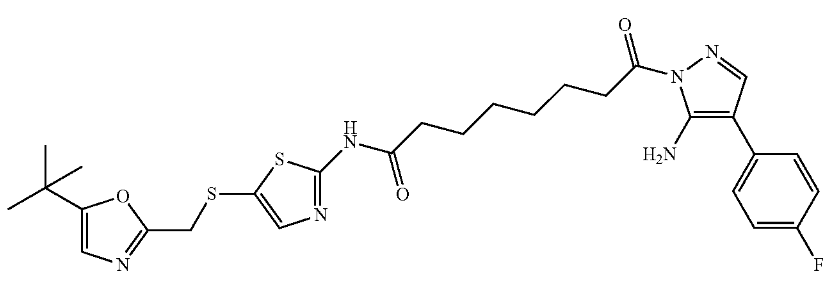 [SMILES: CC(C)(C)c1cnc(CSc2cnc(NC(=O)CCCCCCC(=O)n3ncc(-c4ccc(F)cc4)c3N)s2)o1] |
| 45 | 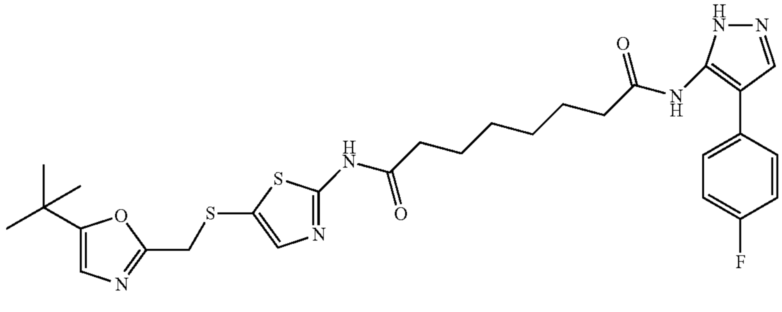 [SMILES: CC(C)(C)c1cnc(CSc2cnc(NC(=O)CCCCCCC(=O)Nc3[nH]ncc3-c3ccc(F)cc3)s2)o1] |

TABLE A-continued
| Compound | Structure |
|---|---|
| 46 | 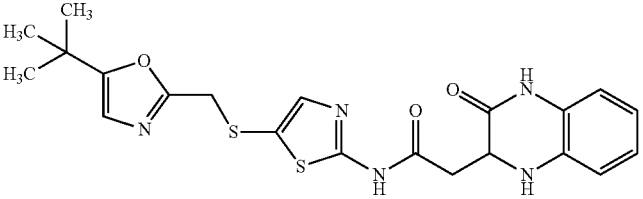 [SMILES: CC(C)(C)c1cnc(CSc2cnc(NC(=O)CC3Nc4ccccc4NC3=O)s2)o1] |
| 47 | 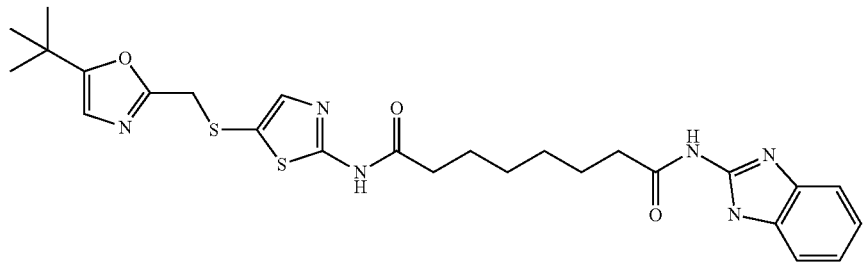 [SMILES: CC(C)(C)c1cnc(CSc2cnc(NC(=O)CCCCCCC(=O)Nc3nc4ccccc4[nH]3)s2)o1] |
| 48 | 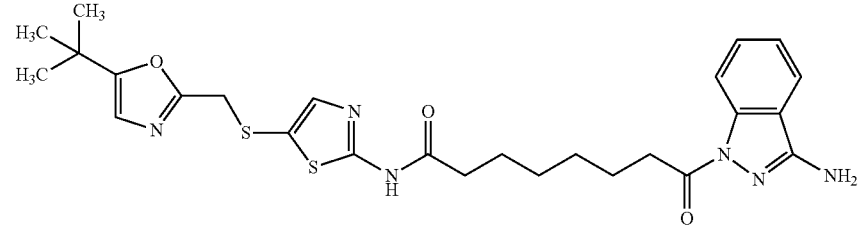 [SMILES: CC(C)(C)c1cnc(CSc2cnc(NC(=O)CCCCCCC(=O)n3nc(N)c4ccccc43)s2)o1] |
| 49 | 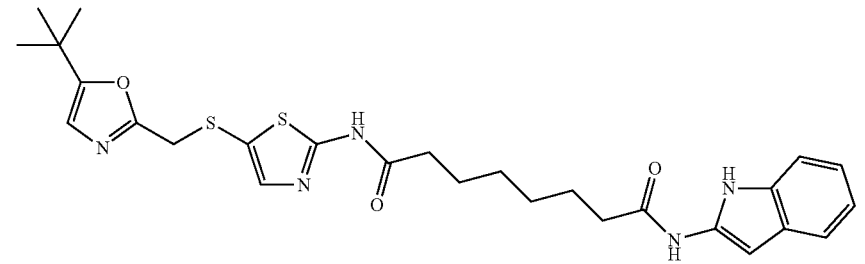 [SMILES: CC(C)(C)c1cnc(CSc2cnc(NC(=O)CCCCCCC(=O)Nc3cc4ccccc4[nH]3)s2)o1] |
| 50 | 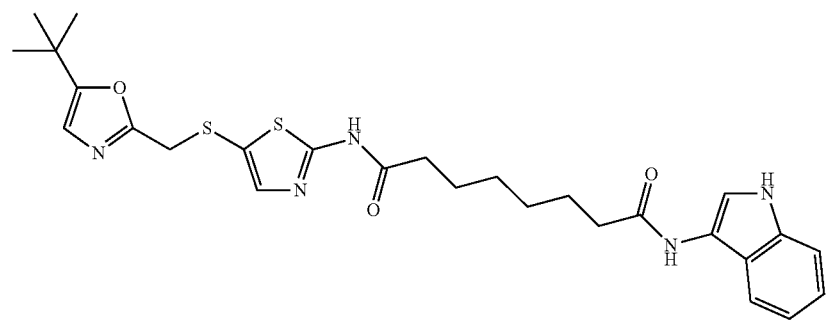 [SMILES: CC(C)(C)c1cnc(CSc2cnc(NC(=O)CCCCCCC(=O)Nc3c[nH]c4ccccc34)s2)o1] |

TABLE A-continued

| Compound | Structure |
|---|---|
| 51 | 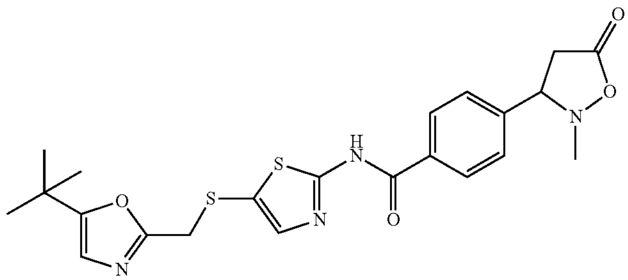 [SMILES: CN1OC(=O)CC1c1ccc(C(=O)Nc2ncc(SCc3ncc(C(C)(C)C)o3)s2)cc1] |
| 52 | 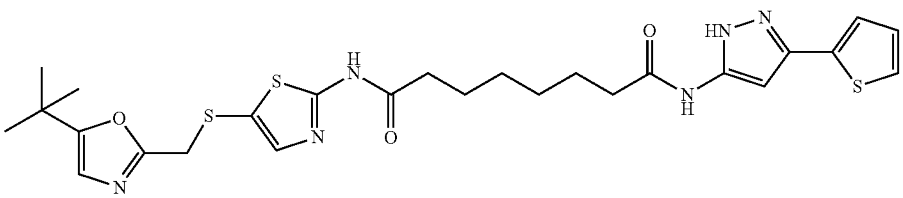 [SMILES: CC(C)(C)c1cnc(CSc2cnc(NC(=O)CCCCCCC(=O)Nc3cc(-c4cccs4)n[nH]3)s2)o1] |
| 61 | 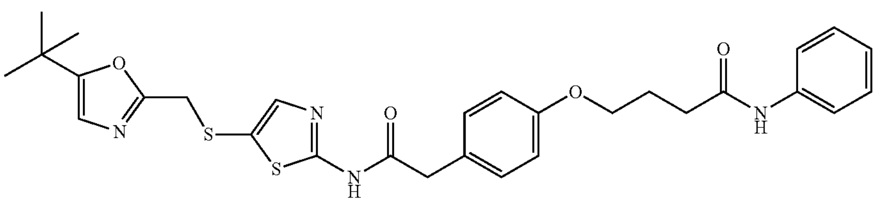 [SMILES: CC(C)(C)c1cnc(CSc2cnc(NC(=O)Cc3ccc(OCCCC(=O)Nc4ccccc4)cc3)s2)o1] |
| 62 | 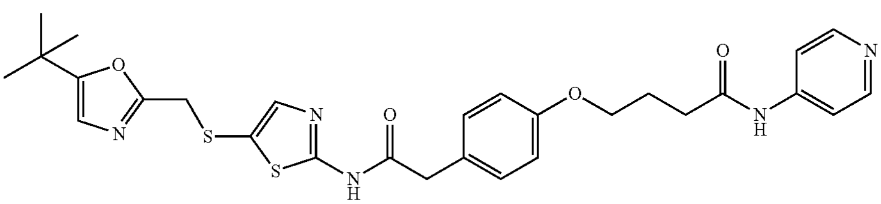 [SMILES: CC(C)(C)c1cnc(CSc2cnc(NC(=O)Cc3ccc(OCCCC(=O)Nc4ccncc4)cc3)s2)o1] |
| 63 | 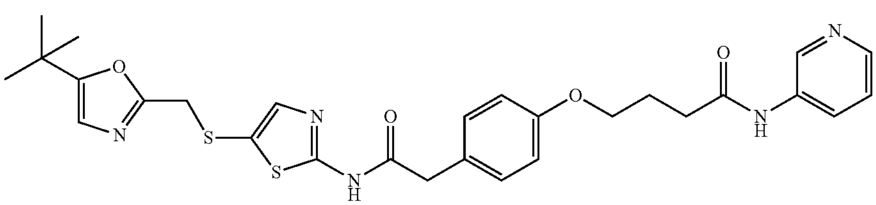 [SMILES: CC(C)(C)c1cnc(CSc2cnc(NC(=O)Cc3ccc(OCCCC(=O)Nc4cccnc4)cc3)s2)o1] |
| 64 | 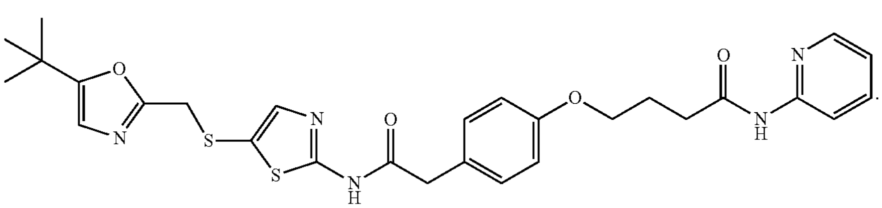 [SMILES: CC(C)(C)c1cnc(CSc2cnc(NC(=O)Cc3ccc(OCCCC(=O)Nc4ccccn4)cc3)s2)o1] |

14. A pharmaceutical composition comprising a compound of claim 1 and a pharmaceutically acceptable carrier.

15. A method of treating a cell proliferative disorder by inhibiting cyclin dependent kinase activity in a subject in need thereof, the method comprising administering to the subject a therapeutically effective amount of the pharmaceutical composition of claim 14.

16. The method of claim 15, wherein said cell proliferative disorder is selected from the group consisting of papilloma, blastoglioma, Kaposi's sarcoma, melanoma, non-small cell lung cancer, ovarian cancer, prostate cancer, colon cancer, squamous cell carcinoma, astrocytoma, head cancer, neck cancer, bladder cancer, breast cancer, lung cancer, colorectal cancer, thyroid cancer, pancreatic cancer, renal cell carcinoma, gastric cancer, hepatocellular carcinoma, neuroblastoma, leukemia, lymphoma, vulcar cancer, Hodgkin's disease and Burkitt's disease.

17. A method for treating a viral infection selected from human immunodeficiency virus (HIV), human papilloma virus, herpesvirus, poxvirus, Epstein-Barr virus, Sindbis virus or adenovirus comprising administering to a subject in need thereof a therapeutically effective amount of a pharmaceutical composition of claim 14.

\* \* \* \* \*

UNITED STATES PATENT AND TRADEMARK OFFICE
CERTIFICATE OF CORRECTION

PATENT NO. : 8,691,820 B2  Page 1 of 1
APPLICATION NO. : 13/167208
DATED : April 8, 2014
INVENTOR(S) : Changgeng Qian et al.

It is certified that error appears in the above-identified patent and that said Letters Patent is hereby corrected as shown below:

In the Claims

Column 88, Claim 9, line 10:

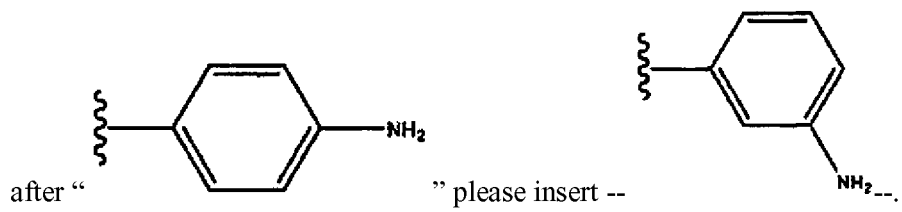

Signed and Sealed this
First Day of July, 2014

Michelle K. Lee
*Deputy Director of the United States Patent and Trademark Office*